United States Patent
Peralta-Yahya et al.

(10) Patent No.: US 12,319,948 B2
(45) Date of Patent: Jun. 3, 2025

(54) PTERIN-DEPENDENT BIOCATALYSTS AND USES THEREOF

(71) Applicant: Georgia Tech Research Corporation, Atlanta, GA (US)

(72) Inventors: Pamela Peralta-Yahya, Atlanta, GA (US); Amy M. Ehrenworth, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 791 days.

(21) Appl. No.: 17/381,553

(22) Filed: Jul. 21, 2021

(65) Prior Publication Data
US 2022/0090154 A1    Mar. 24, 2022

Related U.S. Application Data

(62) Division of application No. 15/541,114, filed as application No. PCT/US2015/068228 on Dec. 31, 2015, now Pat. No. 11,085,060.

(60) Provisional application No. 62/130,257, filed on Mar. 9, 2015, provisional application No. 62/099,309, filed on Jan. 2, 2015.

(51) Int. Cl.
| | |
|---|---|
| C12P 17/18 | (2006.01) |
| C12N 9/02 | (2006.01) |
| C12N 9/04 | (2006.01) |
| C12N 9/78 | (2006.01) |
| C12N 9/88 | (2006.01) |
| C12N 15/52 | (2006.01) |
| C12P 7/00 | (2006.01) |
| C12P 7/22 | (2006.01) |
| C12P 13/00 | (2006.01) |
| C12P 13/22 | (2006.01) |
| C12P 17/10 | (2006.01) |
| C12P 17/12 | (2006.01) |
| C12P 17/16 | (2006.01) |
| C12P 19/60 | (2006.01) |

(52) U.S. Cl.
CPC .......... *C12P 17/182* (2013.01); *C12N 9/0006* (2013.01); *C12N 9/0036* (2013.01); *C12N 9/78* (2013.01); *C12N 9/88* (2013.01); *C12N 15/52* (2013.01); *C12P 7/00* (2013.01); *C12P 7/22* (2013.01); *C12P 13/001* (2013.01); *C12P 13/225* (2013.01); *C12P 13/227* (2013.01); *C12P 17/10* (2013.01); *C12P 17/12* (2013.01); *C12P 17/16* (2013.01); *C12P 17/18* (2013.01); *C12P 19/60* (2013.01); *C12Y 101/01153* (2013.01); *C12Y 106/99* (2013.01); *C12Y 305/04016* (2013.01); *C12Y 401/01028* (2013.01); *C12Y 402/01096* (2013.01); *C12Y 402/03012* (2013.01)

(58) Field of Classification Search
CPC .... C12N 15/52; C12N 9/0006; C12N 9/0036; C12N 9/78; C12P 13/227; C12P 17/12; C12P 17/182; C12P 7/22; C12P 19/60; C12P 17/16; C12P 17/18; C12Y 101/01153; C12Y 305/04016; C12Y 401/01028; C12Y 402/01096; C12Y 402/03012
See application file for complete search history.

(56) References Cited

U.S. PATENT DOCUMENTS

2006/0008869 A1    1/2006 Yabuta et al.

FOREIGN PATENT DOCUMENTS

| WO | 2000042200 A1 | 7/2000 |
| WO | 2013127915 A1 | 9/2013 |

OTHER PUBLICATIONS

Pavon et al. Demonstration of a Peroxide Shunt in the Tetrahydropterin-Dependent Aromatic Amino Acid Monooxygenases. J Am Chem Soc. 2009;131(13):4582-4583.*
Maller et al. Aromatic L-Amino Acid Decarboxylase Deficiency: Clinical Features, Diagnosis, and Treatment of a Second Family. J Child Neurol. 1997;12(6):349-354.*
International Search Report PCT/US2015/068228 mailed Apr. 15, 2015.
Farre et al. "Engineering Complex Metabolic Pathways in Plants." Annual Review of Plant Biology, Feb. 26, 2014 (Feb. 26, 2014), vol. 65, pp. 187-223.
Thony et al. "Tetrahydrobiopterin biosynthesis, regeneration and functions." Biochemical Journal, Apr. 1, 2000 (Apr. 1, 2000), vol. 347, pp. 1-16.
Ehrenworth et al. "Prterin-dependant mono-oxidation for the microbial synthesis of a modified monoterpene indole alkaloid," ACS Synthetic Biology, Dec. 18, 2015 (Jul. 27, 2015), vol. 4, pp. 1295-1307.
Naponelli et al. "Phylogenomic and Functional Analysis of Pterin-4a-Carbinolamine Dehydratase Family (COG2154) Proteins in Plants and Microorganisms," Plant Physiology, Apr. 30, 2008 (Apr. 30, 2006), vol. 146, pp. 1515-1527.
Allen, R. S., Millgate, A. G., Chitty, J. A., Thisleton, J., Miller, J. A. C., Fist, A. J., Gerlach, W. L., and Larkin, P. J. RNAi-mediated replacement of morphine with the nonnarcotic alkaloid reticuline in opium poppy. (Dec. 2004) pp. 1559-1566. Nat. Biotechnol. vol. 22. No. 12.

(Continued)

*Primary Examiner* — Lynn Y Fan
(74) *Attorney, Agent, or Firm* — Thomas| Horstemeyer, LLP

(57) ABSTRACT

Provided herein are biocatalysts and systems thereof for pterin-dependent enzymes and pathways and methods of making and using the same.

14 Claims, 48 Drawing Sheets
Specification includes a Sequence Listing.

(56) References Cited

OTHER PUBLICATIONS

Anzellotti, D. and Ibrahim, R. K. Novel Flavonol 2-Oxoglutarate Dependent Dioxygenase: Affinity Purification, Characterization, and Kinetic Properties. (Oct. 2000) pp. 161-172, Archives of Biochem. Biophys. vol. 382, No. 2. Academic Press.
Arnold K., Bordoll L., Kopp J. & Schwede T. The Swiss-Model Workspace: A web-based environment for protein structure homology modelling. (2006). pp. 195-201. Bioinformatics vol. 22, No. 2. Oxford University Press.
Barnes, H. J., Arlotto, M. P., and Waterman, M. R. (1991) Expression and Enzymatic-Activity of Recombinant Cytochrome-P450 17-Alpha-Hydroxylase in *Escherichia-coli*. Proc. (Jul. 1991). pp. 5597-5601. Natl. Acad. Sci. U.S.A. vol. 88.
Battersby A.R., Burnett, A. R., and Parsons, P. G. Alkaloid Biosynthesis Part XV. Partial Synthesis and Isolation of Vincoside and Isovincoside—Biosynthesis of 3 Major Classes of Indole Alkaloids from Vincoside. (Jan. 1969). pp. 1193-1200. The Chemical Society. Downloaded by Georgia Institute of Technology on Oct. 5, 2018.
Belanger-Quintana, A., Burlina, A., Harding, C. O., and Muntau, A. C. Up to date knowledge on different treatment strategies for phenylketonuria. (2011) Mol. Genet. Metab. 104, S19-S25. Elsevier Inc.
Bernhardt, P., Usera, A. R., and O'Connor, S. E. Biocatalytic asymmetric formation of tetrahydro-beta-carbolines. (Aug. 2010). Tetrahedron Lett. 51, 4400-4402. Elsevier Ltd.
Bernhardt, P., Yerkes, N., and O'Connor, S. E. Bypassing stereoselectivity in the early steps of alkaloid biosynthesis. (Oct. 2009) Org. Biomol. Chem. 7, 4166-4168.
Birdsall, T. C. 5-Hydroxytryptophan: a clinically-effective serotonin precursor. (1998) pp. 271-280. Alt. Med. Rev. : A Journal of Clinical Therapeutic vol. 3, No. 4.
Blau, N., and Niederwieser, A. The application of 8-aminoguanosine triphosphate, a new inhibitor of GTP cyclohydrolase I, to the purification of the enzyme from human liver. (1986) Biochim. Biophys. Acta 880, 26-31. Elsevier Science Publishers B.V. (Biomedical Division).
Brown, S., Clastre, M., Courdavault, V., and O'Connor, S. E. De novo production of the plant-derived alkaloid strictosidine in yeast. (Mar. 2015). pp. 3205-3210. Proc. Natl. Acad. Sci. U.S.A. vol. 112, No. 11. PNAS Direct Submission.
Burgisser, D. M., Thony, B., Redweik, U., Hess, D., Heizmann, C. W., Huber, R., and Nar, H. 6-Pyruvoyl Tetrahydropterin Synthase, an Enzyme with a Novel Type of Active-Site Involving Both Zinc-Binding and an Intersubunit Catalytic Triad Motif ~ Site-Directed Mutagenesis of the Proposed Active-Center, Characterization of the Metal-Binding Site and Modeling of Substrate-Binding. (1995) pp. 358-369. J. Mol. Biol. 253.
Campestrini, Sandro, et al. "A Mechanistic Study on Alcohol Oxidations with Oxygen Catalysed by TPAP-Doped Ormosils in Supercritical Carbon Dioxide." Advanced Synthesis & Catalysis 347.6 (Mar. 2005): 825-832.
Carkaci-Salli, N., Flanagan, J. M., Martz, M. K., Salli, U., Walther, D. J., Bader, M., and Vrana, K. E. (2006) Functional domains of human tryptophan hydroxylase 2 (hTPH2). J. Biol. Chem. 281, 28105-28112.
Crnňáková, Marta, et al. "Potential antimutagenic activity of berberine, a constituent of Mahonia aquifolium." BMC complementary and alternative medicine 2.1 (Feb. 2002): 2.
Chang, M. C. Y., Eachus, R. A., Trieu, W., Ro, D. K., and Keasling, J. D. (May 2007) Engineering *Escherichia coli* for production of functionalized terpenoids using plant P450s. Nat. Chem. Biol. vol. 3, pp. 274-277.
Chemler, Joseph A., and Mattheos AG Koffas. "Metabolic engineering for plant natural product biosynthesis in microbes." Current opinion in biotechnology 19.6 (2008): 597-605.
Connolly, B. S., and Lang, A. E. (2014) Pharmacological Treatment of Parkinson Disease A Review. JAMA, J. Am. Med. Assoc. 311, 1670-1683.

Cordavault, V., Papon, N., Clastre, M., Giglioli-Guivarc'h, N., St-Pierre, B. & Burlat, V. A look inside an alkaloid multisite plant: Catharanthus logistics. Curr. Opin. Plant Biol. 19, 43-50, (Apr. 2014).
Da Silva, N. A., and Srikrishnan, S. (Jan. 2012) Introduction and expression of genes for metabolic engineering applications in *Saccharomyces cerevisiae*. Fems Yeast Res. 12, pp. 197-214. Blackwell Publishing Ltd.
Davis, M. D., Kaufman, S., and Milstien, S. (1988) The auto-oxidation of tetrahydrobiopterin. Eur. J. Biochem. 173, 345-351.
DeLoache, W. C., Russ, Z. N., Narcross, L., Gonzales, A. M., Martin, V. J., and Dueber, J. E. (Jul. 2015) An enzyme-coupled biosensor enables (S)-reticuline production in yeast from glucose. Nat. Chem. Biol. vol. 11. Nature America, Inc.
Dittrich, H. Kutcham, T.M. (Nov. 1991) Molecular clonin, expression, and induction of berberine bridge enzyme, and enzyme essential to the formation of benzyophenanthridine alkaloids in the response of plants to pathogenic attack. Proc. Natl. Acad. Sci. U.S.A. 88, 9969-9973.
Dowers, T.S. et al. (2004) An Analysis of the Regioselectivity of Aromatic Hydroxylation and N-Oxygenation by Cytochrome P450 Enzymes. Drug Metabolism and Disposition vol. 32, No. 3, pp. 328-332, The American Society for Pharmacology and Experimental Therapeutics.
Ensley, B. et al. (1983) Expression of Naphthalene Oxidation Genes in *Escherichia coli* Results in the Biosynthesis of Indigo. Science 222, 167-169. Downloaded from www.sciencemag.org on Aug. 25, 2009.
Fitzpatrick, P. F. (1999) Tetrahydropterin-dependent amino acid hydroxylases. Annu. Rev. Biochem. 68, 355-381.
Fossati, E., Ekins, A., Narcross, L., Zhu, Y., Falgueyret, J. P., Beaudoin, G. A. W., Facchini, P. J., and Martin, V. J. J. (Feb. 2014) Reconstitution of a 10-gene pathway for synthesis of the plant alkaloid dihydrosanguinarine in *Saccharomyces cerevisiae*. Nat. Commun. 5:3283.
Fossati, E., Narcross, L., Ekins, A., Falgueyret, J. P., and Martin, V. J. J. (Apr. 2015) Synthesis of Morphinan Alkaloids in *Saccharomyces cerevisiae*. PloS one 10.
Frick, S., Kramell, R., and Kutchan, T. M. (2007) Metabolic engineering with a morphine biosynthetic P450 in opium poppy surpasses breeding. Metab. Eng. 9, 169-176. Elsevier Inc.
Friedrich, A., Brase, S., and O'Connor, S. E. (2009) Synthesis of 4-, 5-, 6-, and 7-azidotryptamines. Tetrahedron Lett. 50, 75-76.
Geerlings, A., Redondo, F. J., Contin, A., Memelink, J., van der Heijden, R., and Verpoorte, R. (Jun. 2001) Biotransformation of tryptamine and secologanin into plant terpenoid indole alkaloids by transgenic yeast. Appl. Microbiol. Biotechnol. 56, 420-424.
Gibson, D.G., Young, L., Chuang, R-Y., Venter, J.C., Hutchison III, C.A. & Smith, H.O. Enzymatic assembly of DNA molecules up to several hundred kilobases. Nat. Methods 6, 343 -345 (May 2009).
Glenn, W. S., Nims, E., and O'Connor, S. E. (2011) Reengineering a Tryptophan Halogenase to Preferentially Chlorinate a Direct Alkaloid Precursor. Journal of the American Chemical Society 133, 19346-19349.
Glenn, W. S., Runguphan, W., and O'Connor, S. E. (2013) Recent progress in the metabolic engineering of alkaloids in plant systems. Curr. Opin. Biotechnol. 24, 354-365.
Glick, B. R. (1995) Metabolic Load and Heterologous Gene-Expression. Biotechnol. Adv. vol. 13, pp. 247-261. Elsevier Science Ltd.
Gold, N. D., Gowen, C. M., Lussier, F. X., Cautha, S. C., Mahadevan, R. & Martin, V. J. (2015) Metabolic engineering of a tyrosine-overproducing yeast platform using targeted metabolomics. Microb Cell Fact 14, 73.
Hagel, J. M., and Facchini, P. J. (Jan. 2013) Benzylisoquinoline Alkaloid Metabolism: A Century of Discovery and a Brave New World. Plant Cell Physiol. 54, 647-672. Nature America Inc.
Hagel, J.M. & Facchini, P.J. Dioxygenases catalyze the O-demethylation steps of morphine biosynthesis in opium poppy. Nat. Chem. Biol. 6, 273-275 (Mar. 2010). Nature America Inc.
Harvey, A. L. (Oct. 2008) Natural products in drug discovery. Drug Discovery Today vol. 13, 894-901.

(56) References Cited

OTHER PUBLICATIONS

Hasler, T., and Curtius, H. C. (1989) Purification and characterization of 6-pyruvoyl tetrahydropterin synthase from salmon liver. Eur. J. Biochem. / FEBS 180, 205-211.
Hawkins, K. M., and Smolke, C. D. (Sep. 2008) Production of benzylisoquinoline alkaloids in *Saccharomyces cerevisiae*. Nat. Chem. Biol. 4, 564-573. Nature Publishing Group.
Hernandez-Romero, D., Sanchez-Amat, A., and Solano, F. (2006) A tyrosinase with an abnormally high tyrosine hydroxylase/dopa oxidase ratio—Role of the seventh histidine and accessibility to the active site. Febs J. 273, 257-270.
Hofer, R., Boachon, B., Renault, H., Gavira, C., Miesch, L., Iglesias, J., Ginglinger, J. F., Allouche, L., Miesch, M., Grec, S., Larbat, R. & Werck, D. Dual function of the CYP76 family from *Arabidopsis thaliana* in the metabolism of monoterpenols and phenylurea herbicides. (Nov. 2014) Plant Physiol. American Society of Plant Biologists.
Hong, K. K., and Nielsen, J. (Mar. 2012) Metabolic engineering of *Saccharomyces cerevisiae*: a key cell factory platform for future biorefineries. Cell Mol. Life Sci. 69, 2671-2690.
Jones, K. L., Kim, S. W., and Keasling, J. D. (Oct. 2000) Low-Copy Plasmids can Perform as Well as or Better Than High-Copy Plasmids for Metabolic Engineering of Bacteria. Metab. Eng. 2, 328-338.
Kanehisa, M. Goto, S. KEGG:Kyoto encyclopedia of genes and genomes Nucleic Acids Res. vol. 28, 27-30 (2000). Oxford University Press.
Kiefer F., Arnold K., Künzli M., Bordoll L. & Schwede T. The Swiss-Model Repository and associated resources. Nucleic Acids Res. 37, D387-D392 (2009).
Kim, J.S., Nakagawa, A., Yamazaki, Y., Matsumura, E., Koyanagi, T., Minami, H., Katayama, T., Sato, F. & Kumagai, H. Improvement of Reticuline Productivity from Dopamine by Using Engineered *Escherichia coli*. Bioscl. Biotechnol. Biochem. 77, 2166-2168 (Oct. 2013).
Kleinert, M. and Barth, T. (2008) Towards a Lignincellulosic Biorefinery: Direct One-Step Conversion of Lignin to Hydrogen-Enriched Biofuel. Energy & Fuels 22, 1371-1379. American Chemical Society.
Kuboyama, T., Yokoshima, S., Tokuyama, H., and Fukuyama, T. (Aug. 2004) Stereocontrolled total synthesis of (+)-vincristine. Proc. Natl. Acad. Scl. U. S. A. 101, 11966-11970.
Land, E. J., Ramsden, C. A., and Riley, P. A. (2003) Tyrosinase autoactivation and the chemistry of ortho-quinone amines. Accounts Chem. Res. 36, 300-308.
Leiros, H. K. S., Pey, A. L., Innselset, M., Moe, E., Leiros, I., Steen, I. H., and Martinez, A. (2007) Structure of phenylalanine hydroxylase from Colwellia psychrerythraea 34H, a monomeric cold active enzyme with local flexibility around the active site and high overall stability. J. Biol. Chem. 282, 21973-21986.
Leonard, E., Runguphan, W., O'Connor, S., and Prather, K. J. (2009) Opportunities in metabolic engineering to facilitate scalable alkaloid production. Nat. Chem. Biol. 5, 292-300,.
Lin, Y. H., Sun, X. X., Yuan, Q. P., and Yan, Y. J. (2014) Engineering Bacterial Phenylalanine 4-Hydroxylase for Microbial Synthesis of Human Neurotransmitter Precursor 5-Hydroxytryptophan. ACS Synth. Biol. 3, 497-505.
Lücke,B., et. al. (2004) Oxidation and Ammoxidation of Aromatics. Adv. Synth. Catal. 346, 1407-1424.
Luetke-Eversloh, T., Santos, C. N. S., and Stephanopoulos, G. (2007) Perspectives of biotechnological production of L-tyrosine and its applications. Appl. Microbiol. Biotechnol. 77, 751-762.
Luttik, M. A. H., Vuralhan, Z., Suir, E., Braus, G. H., Pronk, J. T. & Daran, J. M. (2008) Alleviation of feedback inhibition in *Saccharomyces cerevisiae* aromatic amino acid biosynthesis: Quantification of metabolic impact. Metab Eng 10, 141-153.
Mancini, R., Saracino, F., Buscemi, G., Fischer, M., Schramek, N., Bracher, A., Bacher, A., Gutlich, M., and Carbone, M. L. A. (1999) Complementation of the fol2 deletion in *Saccharomyces cerevisiae* by human and *Escherichia coli* genes encoding GTP cyclohydrolase I. Biochem. Biophys. Res. Commun. 255, 521-527.

Maresh, J. J., Giddings, L. A., Friedrich, A., Loris, E. A., Panjikar, S., Trout, B. L., Stockigt, J., Peters, B., and O'Connor, S. E. (2008) Strictosidine synthase: mechanism of a Pictet-Spengler catalyzing enzyme. J. Am. Chem. Soc. 130, 710-723.
McCoy, E., Galan, M. C., and O'Connor, S. E. (2006) Substrate specificity of strictosidine synthase. Bioorg. Med. Chem. Lett. 16, 2475-2478.
Miettinen, K., Dong, L. M., Navrot, N., Schneider, T., Burlat, V., Pollier, J., Woittiez, L., van der Krol, S., Lugan, R., llc, T., Verpoorte, R., Oksman-Caldentey, K. M., Martinola, E., Bouwmeester, H., Goossens, A., Memelink, J., and Werck-Reichhart, D. (2014) The seco-iridoid pathway from Catharanthus roseus. Nat. Commun. 5:3606.
Miki, Y., and Asano, Y. (2014) Biosynthetic pathway for the cyanide-free production of phenylacetonitrile in *Escherichia coli* by utilizing plant cytochrome P450 79A2 and bacterial aldoxime dehydratase. Appl.Environ. Microbiol. 80, 6828-6836.
Minami, H. (2013) Fermentative Production of Plant Benzylisoquinoline Alkaloids in Microbes. Biosci. Biotech. Bioch. 77, 1617-1622.
Minami, H., Kim, J. S., Ikezawa, N., Takemura, T., Katayama, T., Kumagai, H., and Sato, F. (2008) Microbial production of plant benzylisoquinoline alkaloids. Proc. Natl. Acad. Sci. U. S. A. 105, 7393-7398.
Mukherjee, K., Bhattacharyya, S. & Peralta-Yahya, P. GPCR-Based Chemical Biosensors for Medium-Chain Fatty Acids. ACS Synth. Biol., (2015).
Murata, J., Roepke, J., Gordon, H., and De Luca, V. (2008) The leaf epidermome of Catharanthus roseus reveals its biochemical specialization. Plant Cell 20, 524-542.
Nakagawa, A., Matsuzaki, C., Matsumura, E., Koyanagi, T., Katayama, T., Yamamoto, K., Sato, F., Kumagai, H., and Minami, H. (2014) (R, S)-Tetrahydropapaveroline production by stepwise fermentation using engineered *Escherichia coli*. Sci Rep 4.
Nakagawa, A., Minami, H., Kim, J. S., Koyanagi, T., Katayama, T., Sato, F., and Kumagai, H. (2011) A bacterial platform for fermentative production of plant alkaloids. Nat. Commun. 2:326 doi: 10.1038/ncomms1327.
O'Connor, S. E., and Maresh, J. J. (2006) Chemistry and biology of monoterpene indole alkaloid biosynthesis. Nat. Prod. Rep. 23, 532-547.
Park, S., Kang, K., Lee, S.W., Ahn, M.J., Bae, J.M. & Back, K. Production of serotonin by dual expression of tryptophan decarboxylase and tryptamine 5-hydroxylase in *Escherichia coli*. Appl. Microbiol. Biotechnol. 89, 1387-1394 (2011).
Peitsch, M. C. Protein modeling by E-mail Nature Biotechnol. 13, 658-660 (1995).
Peralta-Yahya, P. P., Zhang, F. Z., del Cardayre, S. B., and Keasling, J. D. (2012) Microbial engineering for the production of advanced biofuels. Nature 488, 320-328.
Peralta-Yahya, P., Carter, B.T., Lin, H., Tao, H. & Cornish, V.W High-Throughput Selection for Cellulase Catalysts Using Chemical Complementation J. Am. Chem. Soc. 130 (51), 17446-17452 (2008).
Ploom, T., Thony, B., Yim, J., Lee, S., Nar, H., Leimbacher, W., Richardson, J., Huber, R., and Auerbach, G. (1999) Crystallographic and kinetic investigations on the mechanism of 6-pyruvoyl tetrahydropterin synthase. J. Mol. Biol. 286, 851-860.
Ragauskas, A.J. et al. (2014) Lignin Valorization: Improving Lignin Processing in the Blorefinery Science 344, 1246843 DOI: 10.1126/science.1246843.
Ro, D.-K., et al, (2006) Production of the antimalarial drug precursor artemisinic acid in engineered yeast Nature 440, 940-943.
Runguphan, W., and O'Connor, S. E. (2009) Metabolic reprogramming of periwinkle plant culture. Nat. Chem. Biol. 5, 151-153.
Runguphan, W., Qu, X. D., and O'connor, S. E. (2010) Integrating carbon-halogen bond formation into medicinal plant metabolism. Nature 468, 461-464.
Santos, C.N.S. & Stephanopoulos, G. Melanin-based high-throughput screen for L-tyrosine production in *Escherichia coli*. Appl. Environ. Microbiol. 74, 1190-1197 (2008).
Sarria, S., Wong, B., Martin, H. G., Keasling, J. D. & Peralta-Yahya, P. (2014) Microbial Synthesis of Pinene. ACS Synth. Biol., 3, 466-475.

(56) References Cited

OTHER PUBLICATIONS

Sato, F., Hashimoto, T., Hachiya, A., Tamura, K., Chol, K. B., Morishige, T., Fujimoto, H., and Yamada, Y. (2001) Metabolic engineering of plant alkaloid biosynthesis. Proc. Natl. Acad. Sci. U. S. A. 98, 367-372.

Satoh, Y., Tajima, K., Munekata, M., Keasling, J. D., and Lee, T. S. (2012) Engineering of L-tyrosine oxidation in *Escherichia coli* and microbial production of hydroxytyrosol. Metab. Eng. 14, 603-610.

Schafer, H., and Wink, M. (2009) Medicinally important secondary metabolites in recombinant microorganisms or plants: progress in alkaloid biosynthesis. Biotechnol. J. 4, 1684-1703.

Schoedon, G., Redweik, U., Frank, G., Cotton, R. G. H., and Blau, N. (1992) Allosteric Characteristics of Gtp Cyclohydrolase-I from *Escherichia-coli*. Eur. J. Biochem. 210, 561-568.

Siddiqui, M. S., Thodey, K., Trenchard, I., and Smolke, C. D. (2012) Advancing secondary metabolite biosynthesis in yeast with synthetic biology tools. Fems Yeast Res. 12, 144-170.

Silvestrini, A., Pasqua, G., Botta, B., Monacelli, B., van der Heijden, R., and Verpoorte, R. (2002) Effects of alkaloid precursor feeding on a Camptotheca acuminata cell line. Plant Physiol. Bioch. 40, 749-753.

Sun, X., Lin, Y., Yuan, Q., and Yan, Y. (2014) Precursor-Directed Biosynthesis of 5-Hydroxytryptophan Using Metabolically Engineered *E. coli*. ACS Synth. Biol. 4, 554-558.

Thodey, K., Galanie, S., and Smolke, C. D. (2014) A microbial biomanufacturing platform for natural and semisynthetic opioids. Nat. Chem. Biol. 10, 837-844.

Thony, B., Auerbach, G., and Blau, N. (2000) Tetrahydrobiopterin biosynthesis, regeneration and functions. Biochem. J. 347, 1-16.

Ullrich, R. and Hofrichter, M. (2007) Enzymatic hydroxylation of aromatic compounds. Cell. Mol. Life Sci. 64, 271-293.

Wang, H. C., Yang, B., Hao, G. F., Feng, Y., Chen, H. Q., Feng, L., Zhao, J. X., Zhang, H., Chen, Y. Q., Wang, L., and Chen, W. (2011) Biochemical characterization of the tetrahydrobiopterin synthesis pathway in the oleaginous fungus *Mortierella alpina*. Microbiology. 157, 3059-3070.

Werner, E.R., et al. (2011) Tetrahydrobiopterin: biochemistry and pathophysiology. Biochem. J. 438, 397-414.

Werner-Felmayer, G., Golderer, G., and Werner, E. R. (2002) Tetrahydrobiopterin biosynthesis, utilization and pharmacological effects. Curr. Drug Metab. 3, 159-173.

Winter, J. M., and Tang, Y. (2012) Synthetic biological approaches to natural product biosynthesis. Curr. Opin. Biotechnol. 23, 736-743.

Winzer, T., Gazda, V., He, Z., Kaminski, F., Kern, M., Larson, T.R., Li, Y., Meade, F., Teodor, R., Vaistij, F.E., Walker, C., Bowser, T.A. & Graham, I.A. A Papaver somniferum 10-Gene Cluster for Synthesis of the Anticancer Alkaloid Noscapine. Science 336, 1704-1708 (2012).

Yamamoto, K., Kataoka, E., Miyamoto, N., Furukawa, K., Ohsuye, K., and Yabuta, M. (2003) Genetic engineering of *Escherichia coli* for production of tetrahydrobiopterin. Metab. Eng. 5, 246-254.

Yang, L. Q., and Stockigt, J. (2010) Trends for diverse production strategies of plant medicinal alkaloids. Nat. Prod. Rep. 27, 1469-1479.

Yerkes, N., Wu, J. X., McCoy, E., Galan, M. C., Chen, S., and O'Connor, S. E. (2008) Substrate specificity and diastereoselectivity of strictosidine glucosidase, a key enzyme in monoterpene indole alkaloid biosynthesis. Bioorg. Med. Chem. Lett. 18, 3095-3098.

Yim, J. J., and Brown, G. M. (1976) Characteristics of Guanosine Triphosphate Cyclohydrolase-I Purified from *Escherichia-coli*. J. Biol. Chem. 251, 5087-5094.

Zakzeski, (2010) The Catalytic Valorization of Lignin for the Production of Renewable Chemicals J. Chem. Rev. 110, 3552-3599.

* cited by examiner

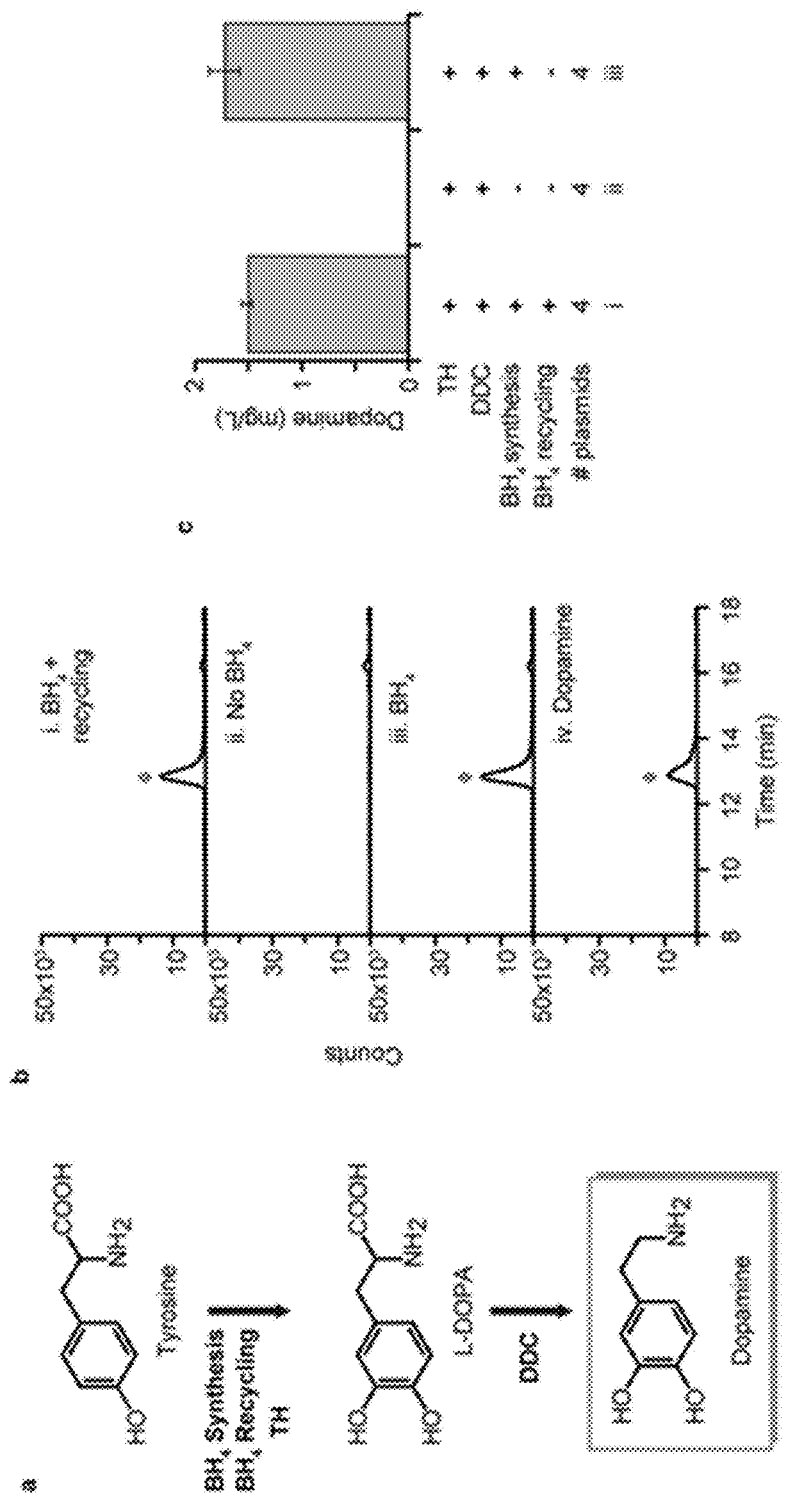

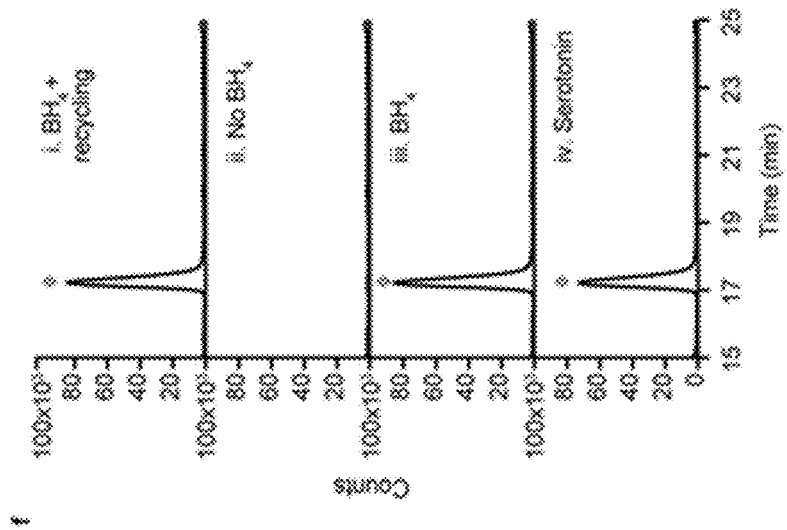
FIG. 9F
FIG. 9E
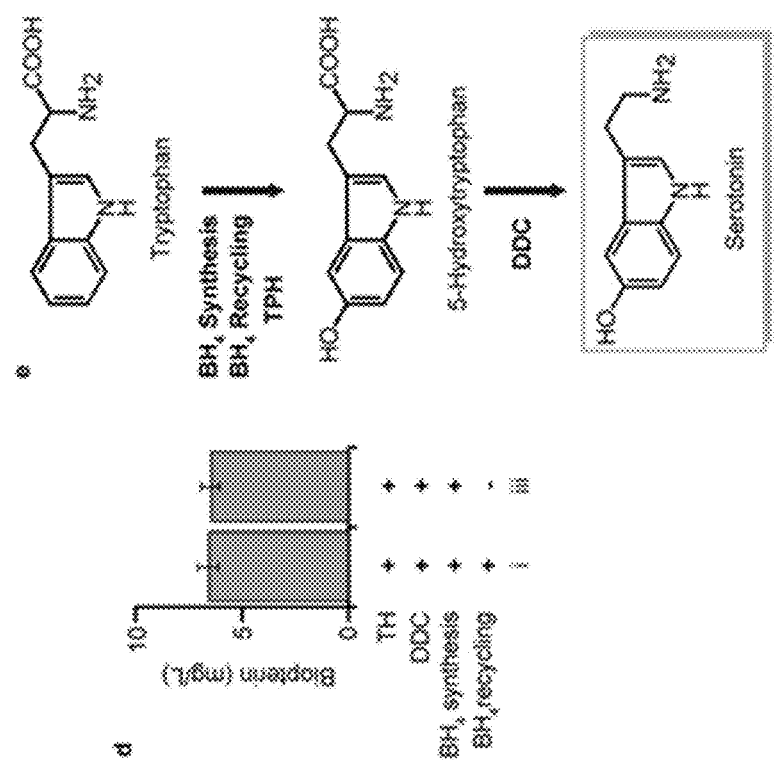
FIG. 9D

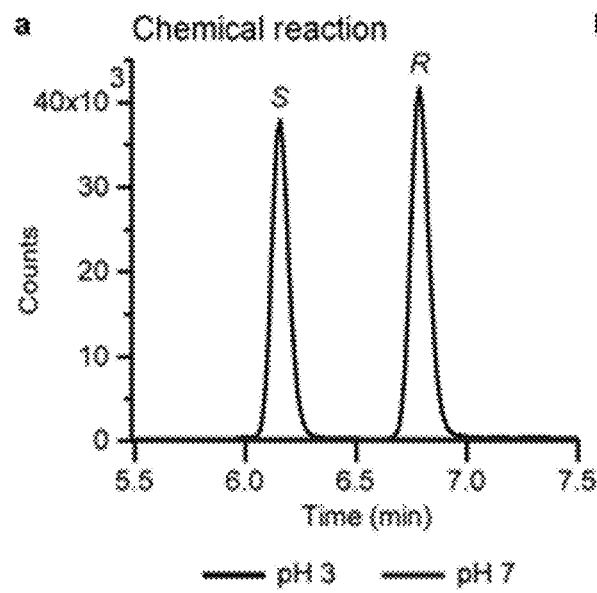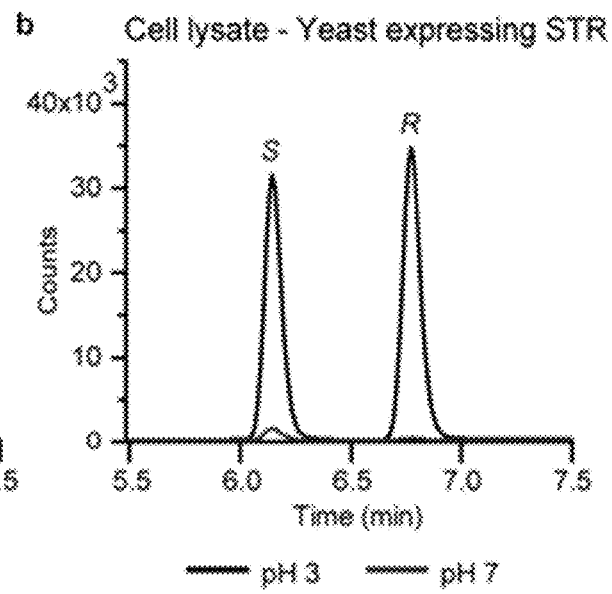
FIG. 11A  FIG. 11B
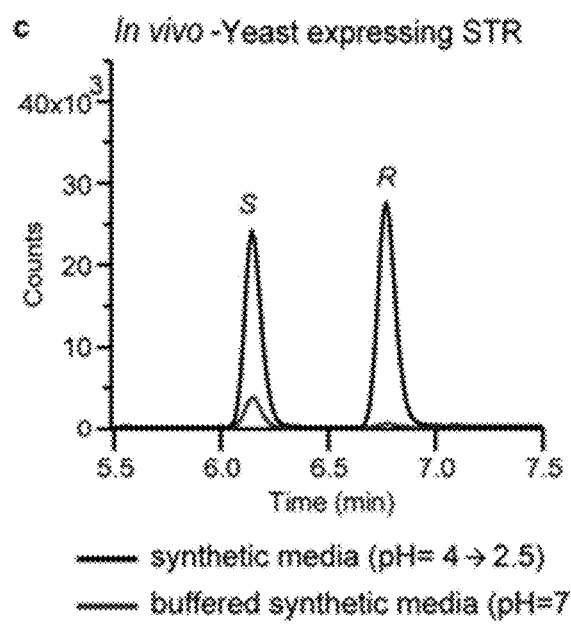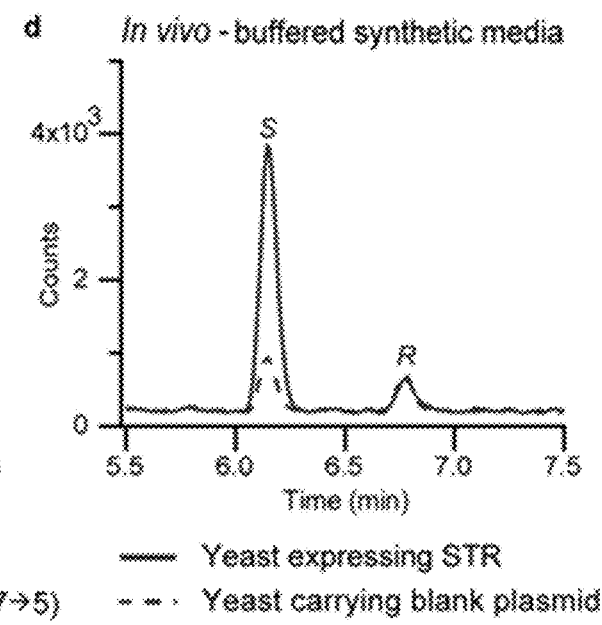
FIG. 11C  FIG. 11D

| Strain | BH4 Synthesis Pathway | BH4 Recycling Pathway | Alkaloid Synthesis Pathway | # Plasmids | Substrate(s) | Product | Production |
|---|---|---|---|---|---|---|---|
| PPY946 | | | TH | 4 | Galactose | L-DOPA | nd |
| PPY646 | ✓ | ✓ | TH | 4 | Galactose | L-DOPA | 0.33 ± 0.02 mg/L |
| PPY679 | ✓ | | TH | 4 | Galactose | L-DOPA | 0.27 ± 0.04 mg/L |
| PPY947 | | | TH, DDC | 4 | Galactose | Dopamine | nd |
| PPY658 | ✓ | ✓ | TH, DDC | 4 | Galactose | Dopamine | 1.52 ± 0.05 mg/L |
| PPY743 | ✓ | | TH, DDC | 4 | Galactose | Dopamine | 1.73 ± 0.14 mg/L |
| PPY948 | | | TPH, DDC | 4 | Galactose | Serotonin | nd |
| PPY649 | ✓ | ✓ | TPH, DDC | 4 | Galactose | Serotonin | 5.72 ± 1.18 mg/L |
| PPY741 | ✓ | | TPH, DDC | 4 | Galactose | Serotonin | 5.18 ± 0.84 mg/L |
| PPY650 | ✓ | ✓ | TPH, DDC, STR | 4 | Galactose, Secologanin | Hydroxystrictosidine | 728.8 ± 206.2 counts |
| PPY955 | ✓ | ✓ | TPH, DDC, STR | 3 | Glucose, Secologanin | Hydroxystrictosidine | 570.6 ± 280.6 counts |
| PPY744 | ✓ | | TPH, DDC, STR | 3 | Glucose, Secologanin | Hydroxystrictosidine | 819.4 ± 357.3 counts |
| PPY746 | | | TPH, DDC, STR | 2 | Glucose, Secologanin | Hydroxystrictosidine | 444.7 ± 246.5 counts |
| PPY740 | | | TPH, DDC, STR | 2 | Galactose, Secologanin | Hydroxystrictosidine | 258.7 ± 91.3 counts |
| PPY649 | ✓ | ✓ | TPH, DDC, STR | 4 | Galactose, Secologanin | Hydroxystrictosidine | 713.9 ± 281.9 counts |

FIG. 33

PTERIN-DEPENDENT BIOCATALYSTS AND USES THEREOF

CROSS-REFERENCE TO RELATED APPLICATIONS

This application is a divisional application of U.S. application Ser. No. 15/541,114, filed on Jun. 30, 2017 is the 35 U.S.C. § 371 national stage application of PCT Application No. PCT/US2015/068228, filed Dec. 31, 2015, where the PCT claims the benefit of U.S. Provisional Application Ser. No. 62/099,309 filed on Jan. 2, 2015, having the title Microbial Synthesis of Monoterpene Indole Alkaloids via Pterin-Dependent Amino Acid Hydroxylation, and U.S. Provisional Application Ser. No. 62/130,257 filed on Mar. 9, 2015, having the title Pterin Dependent Aromatic Mono-Oxidation for Lignin Valorization, all of which are herein incorporated by reference in their entireties as if fully set forth herein.

SUMMARY

Provided herein in some embodiments are biocatalysts having a pterin source and a pterin-dependent enzymatic pathway biologically coupled to the pterin source. Tetrahydrobiopterin (referred to herein as BH4 or $BH_4$) can be the pterin source. The BH4 can be synthesized by a tetrahydrobiopterin synthesis pathway. The tetrahydrobiopterin synthesis pathway can include a GTP cyclohydrase; a pyruvoyl tetrahydropterin synthase; a sepiapterin reductase, and/or any combination thereof. The biocatalyst can further contain a pterin-dependent enzymatic pathway. The pterin-dependent enzymatic pathway can be amino acid mono-oxygenase, phenylalanine hydroxylase, tryptophan hydroxylase, tyrosine hydroxylase, nitric oxide synthase, alkylglycerol monooxygenase, and/or any combination thereof. The enzymatic pathway of the biocatalyst can further contain a decarboxylase and/or modified decarboxylase. The decarboxylase can be aromatic-l-amino acid decarboxylase. The biocatalyst can further contain a synthase. The synthase can be a terpene alkaloid synthase. The synthase can be a strictosidine synthase. The biocatalyst can optionally contain a tetrahydrobiopterin recycling pathway, where the tetrahydrobiopterin recycling pathway can be biologically coupled to the enzymatic pathway. The tetrahydrobiopterin recycling pathway can contain a pterin-4a-carbinolamine dehydratase and a dihydropterin reductase.

The biocatalyst can be contained in a cell. The cell can be an engineered cell. The biocatalyst can contain a tetrahydrobiopterin source and a pterin-dependent enzymatic pathway described previously. The tetrahydrobiopterin source in the cell can be a tetrahydrobiopterin synthesis pathway. The tetrahydrobiopterin synthesis pathway can contain a GTP cyclohydrase, a pyruvoyl tetrahydropterin synthase, a sepiapterin reductase, and/or any combination thereof. The pterin-dependent enzymatic pathway in the cell can contain at least one element selected from the group of an amino acid mono-oxygenase, a modified amino acid mono-oxygenase, phenylalanine hydroxylase, tryptophan hydroxylase, tyrosine hydroxylase, nitric oxide synthase, and alkylglycerol monooxygenase. The pterin-dependent enzymatic pathway in the cell can further contain a decarboxylase and/or a modified decarboxylase. the decarboxylase can be aromatic-l-amino acid decarboxylase. The enzymatic pathway of the biocatalyst in the cell can further include a synthase. The synthase can be a modified or unmodified synthase. The synthase can be a terpene alkaloid synthase. The synthase can be a strictosidine synthase. The synthase can be a deacetylisoipecoside synthase. The biocatalyst of the cell can further contain a tetrahydrobiopterin recycling pathway. The tetrahydrobiopterin recycling pathway can contain a pterin-4a-carbinolamine dehydratase, a dihydrofolate reductase and/or a dihydropterin reductase.

Also described herein are methods of biocatalysis that can be carried out by a biocatalyst. The methods can produce direct and/or selective biocatalysis. The biocatalyst can be contained in a cell. The methods can include the steps of providing a biocatalyst as previously set forth and providing a substrate to the biocatalyst. The biocatalyst can be contained within a cell. The cell can be a eukaryotic or prokaryotic cell. In embodiments, the cell is a yeast cell. In embodiments, the biocatalyst is not contained in a cell. The substrate can be a carbohydrate. The substrate can be glucose. The substrate can be galactose. The substrate can be lignin or a derivative or metabolite thereof.

BACKGROUND

Carbohydrates, sugars and lignins, are abundant sources for a variety of compounds products that have applications ranging from pharmaceuticals to biofuels. While direct isolation of the compounds, which are often plant metabolites, produced from the carbohydrate, sugar, and/or lignin source, directly from the plant is a way to obtain the desired compounds, isolation often proves laborious and modification of the compound is difficult or impossible. As such, there exists a need for improved compositions and methods for obtaining compounds derived from carbohydrates, sugars, and lignins.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 9A-9H show embodiments of a synthesis scheme and data demonstrating microbial synthesis of biogenic amines via pterin-dependent mono-oxidation. (a) Schematic representation of dopamine biosynthesis. (b) Representative LC traces for various production strains (extracted ion chromatograms (EIC) for dopamine=m/z 154). Traces represent strains expressing: i) tyrosine hydroxylase (TH), aromatic-L-amino-acid decarboxylase (DDC), the $BH_4$ synthesis pathway, and the $BH_4$ recycling pathway, ii) TH and DDC, and iii) TH, DDC, and the $BH_4$ synthesis pathway. Trace iv is commercial dopamine standard. Full windows of the spectra can be found in FIG. 17B. (c) Production levels of dopamine in the presence (+) or absence (−) of the $BH_4$ synthesis pathway, and/or the $BH_4$ recycling pathway. (d) Production levels of biopterin in the presence (+) or absence (−) of the $BH_4$ recycling pathway. (e) Schematic representation of serotonin biosynthesis. (f) Representative LC traces for various production strains (EIC for serotonin=m/z 177). Traces represent strains expressing: i) tryptophan hydroxylase (TPH), DDC, the $BH_4$ synthesis pathway, and the $BH_4$ recycling pathway, ii) TPH and DDC, and iii) TPH, DDC, and the $BH_4$ synthesis pathway. Trace iv is commercial serotonin standard. Full windows of the spectra can be found in FIG. 17C. (g) Production levels of serotonin in the presence (+) or absence (−) of the $BH_4$ synthesis pathway and/or $BH_4$ recycling pathway. (h) Production levels of biopterin in the presence (+) or absence (−) of the $BH_4$ recycling pathway. All experiments were run in triplicate and shown are the mean and standard deviation. Strains carried four multicopy plasmids in which each gene was expressed from galactose inducible promoters ($P_{GAL1}$ or $P_{GAL10}$).

FIGS. 11A-11D show graphs demonstrating the analysis of the 10-hydroxystrictosidine isomer ratio. All reactions contain 0.4 mM each of secologanin and serotonin. LC traces trace (extracted ion chromatograms for hydroxystrictosidine=m/z 547) for (a) the chemical reaction in phosphate buffer at pH=3 (black) or pH=7 (red), (b) the reaction in cell lysate of yeast expressing strictosidine synthase (PPY827) adjusted to pH=3 (black) or pH=7 (red), (c) in vivo reaction using intact yeast cells expressing strictosidine synthase (PPY827) in standard yeast media (black) or pH=7 buffered media (red), and (d) in vivo reaction using intact yeast cells expressing either strictosidine synthase (PPY827, solid red line) or yeast expressing a blank plasmid (PPY828, dotted red line) in pH=7 buffered media. Full windows of the spectra can be found in FIG. 24.

Figure 7A:
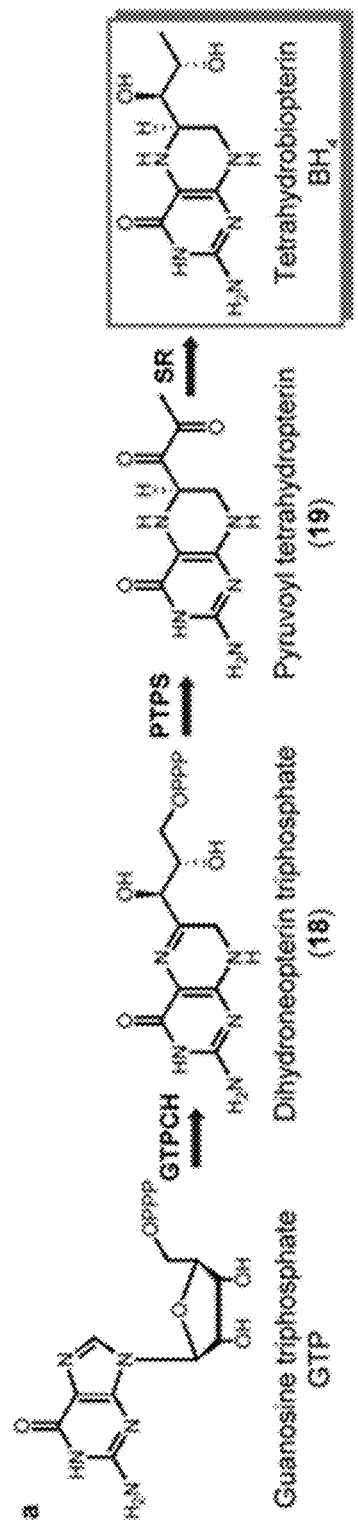
FIGS. 7A-7F show embodiments of a synthesis scheme and data demonstrating. production of tetrahydrobiopterin ($BH_4$) in *S. cerevisiae*. (a) $BH_4$ biosynthetic pathway from guanosine triphosphate (GTP), which is endogenously made by *S. cerevisiae*. (b) Heat map of biopterin titers (mg/L), as a proxy for $BH_4$ titers, from the 49 $BH_4$-production yeast strains. Except for *S. cerevisiae* chromosomal (c), where the chromosomal copy of *S. cerevisiae* GTPCH was used, each enzyme was expressed from a multicopy plasmid from an inducible galactose promoter ($P_{GAL1}$). Biopterin was quantified using liquid chromatography/mass spectrometry (LC/MS). Bio[pterin tires reporter as (−) were not determined. Production levels reported as 0.00 were either too low to quantify or undetectable. A control strain expressing green fluorescent protein in a three-plasmid system showed no biopterin production. The experiments were run in triplicate and shown are the means. Standard deviations can be found in FIG. 13A. (c) LC/MS traces (extracted ion chromatograms) of $BH_4$ (m/z 242) and oxidation products dihydrobiopterin (m/z 240) and biopterin (m/z 238) found intracellularly and in the production medium. Standard retention times: $BH_4$=2.6 min, dihydrobiopterin=5.3 min, biopterin=4.6 min. Only biopterin was observed in the production medium. Full windows of the spectra can be found in FIG. 13B. (d) Pterin-dependent mono-oxidation of tyrosine to L-DOPA using the original $BH_4$ synthesis strain (*S. cerevisiae* GTPCH, *M. alpina* PTPS and SR) and the combinatorially optimized $BH_4$ synthesis strain (*E. coli* GTPCH, *M. alpina* PTPS and SR), both strains carrying tyrosine mono-oxygenase. Improving $BH_4$ production improves amino acid mono-oxidation. (e) Optimization of $BH_4$ biosynthesis. $BH_4$ synthesis pathway: *E. coli* GTPCH, *M. alpina* PTPS and SR. For the glucose system, all three enzymes were expressed from a single multicopy plasmid under control of constitutive promoters ($P_{ADH1}$, $P_{TEF1}$, and $P_{HXT7}$). (f) $BH_4$ biosynthetic pathway bottleneck identification. Biopterin production from galactose in yeast expressing each $BH_4$ biosynthetic enzyme from either a single-copy (s) or a multicopy (m) plasmid. All experiments were run in triplicate and shown are the mean and standard deviation. GTPCH: GTP cyclohydrolase; PTPS: pyruvoyl tetrahydropterin synthase; SR: sepiapterin reductase.
Figure 7B:
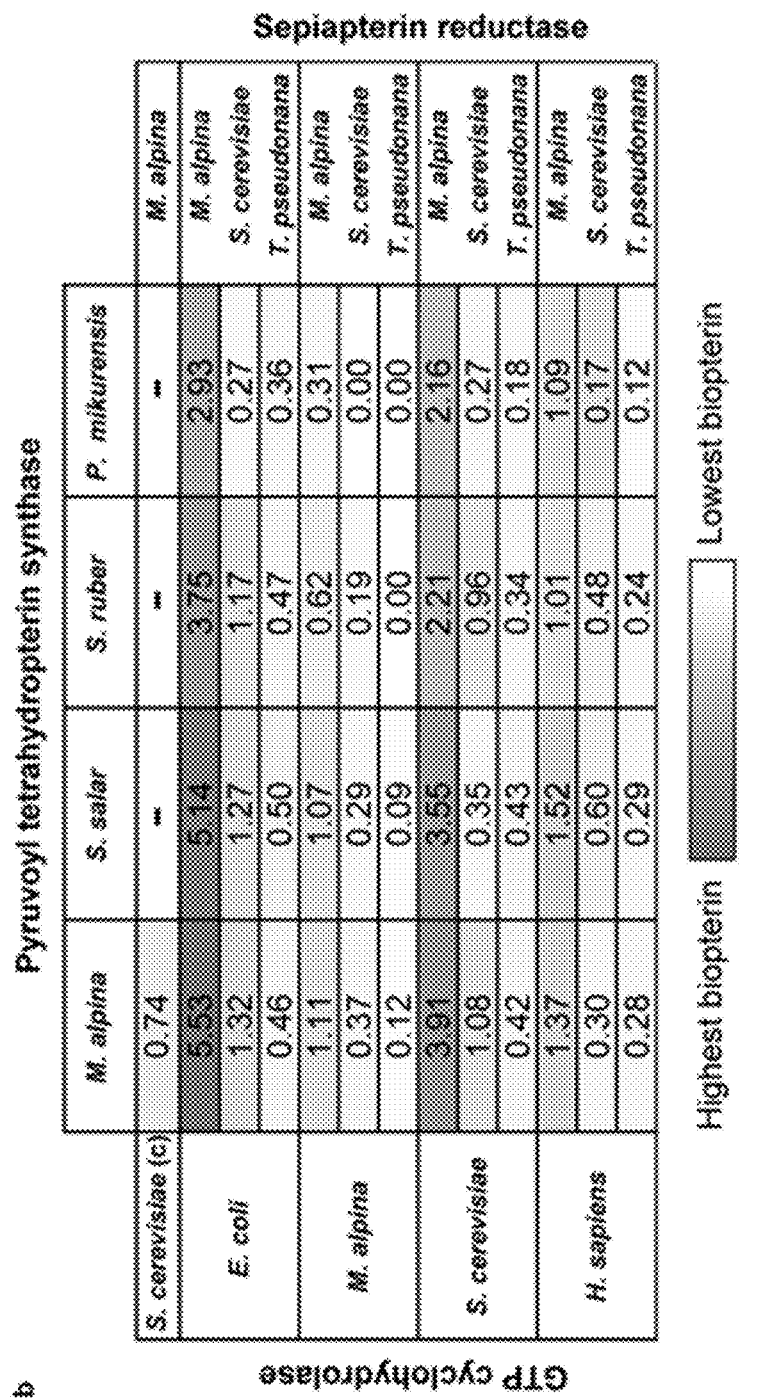
Figure 7C:
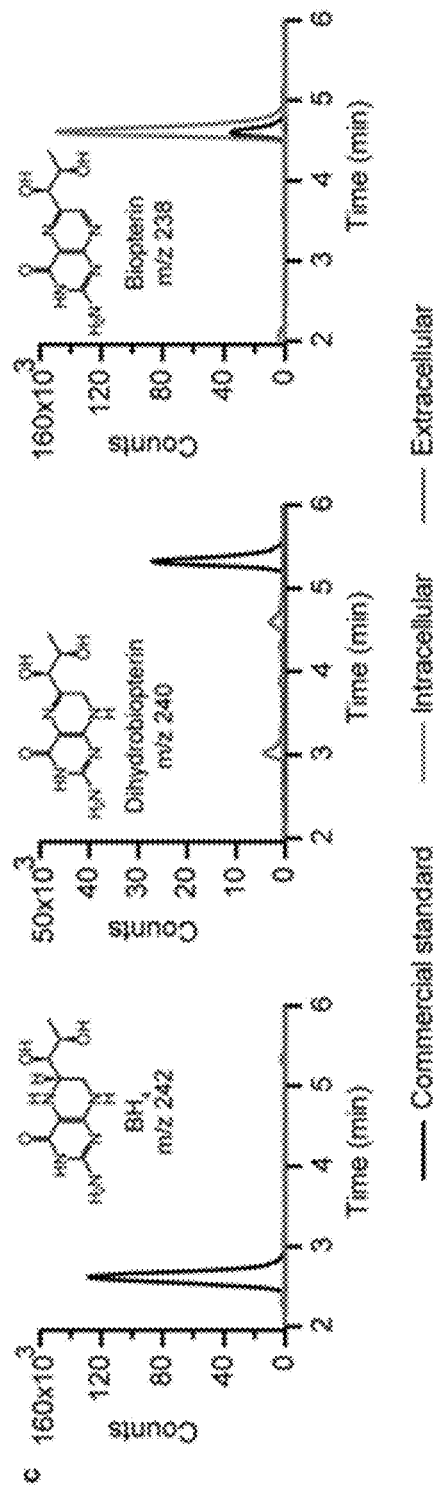
Figure 7D:
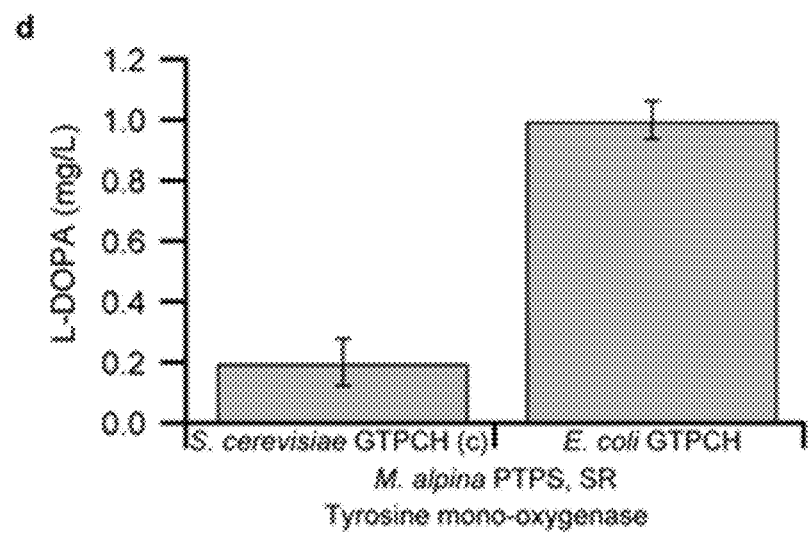
Figure 7E:
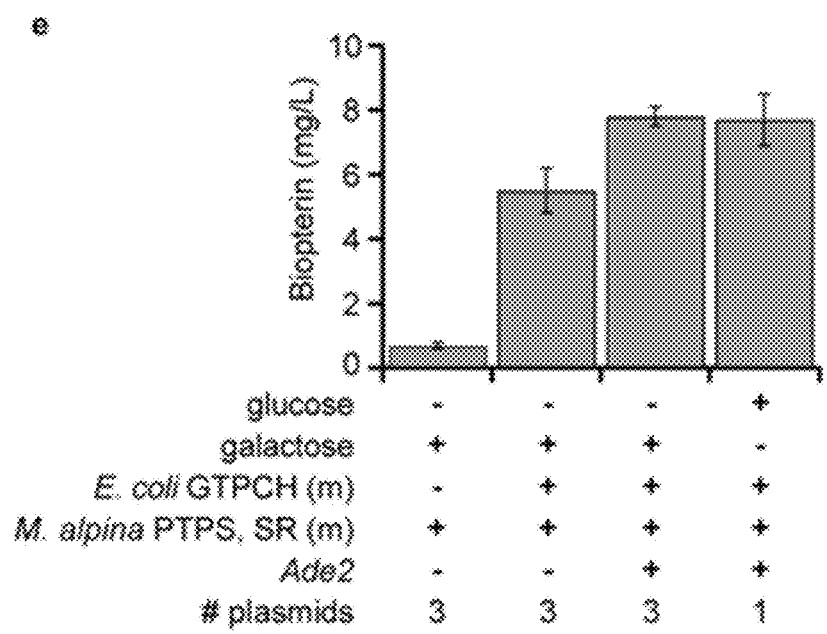
Figure 7F:
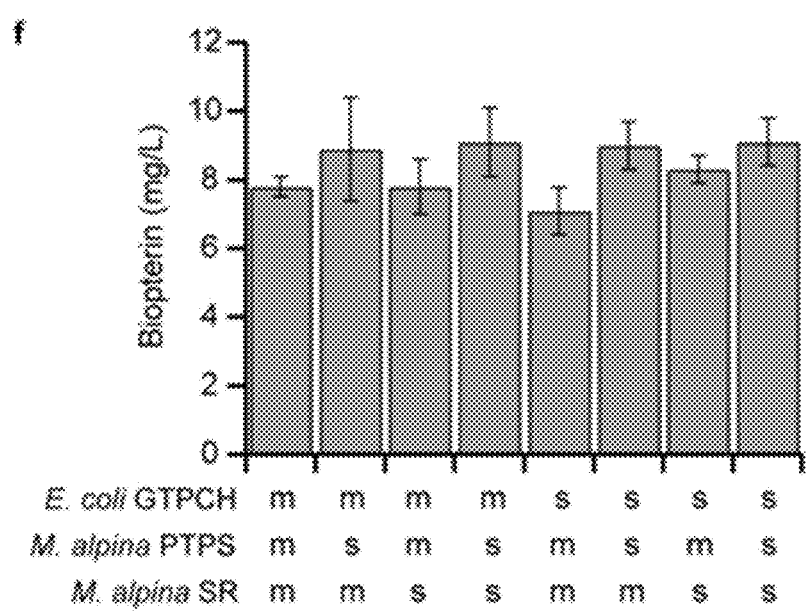
Figure 26:
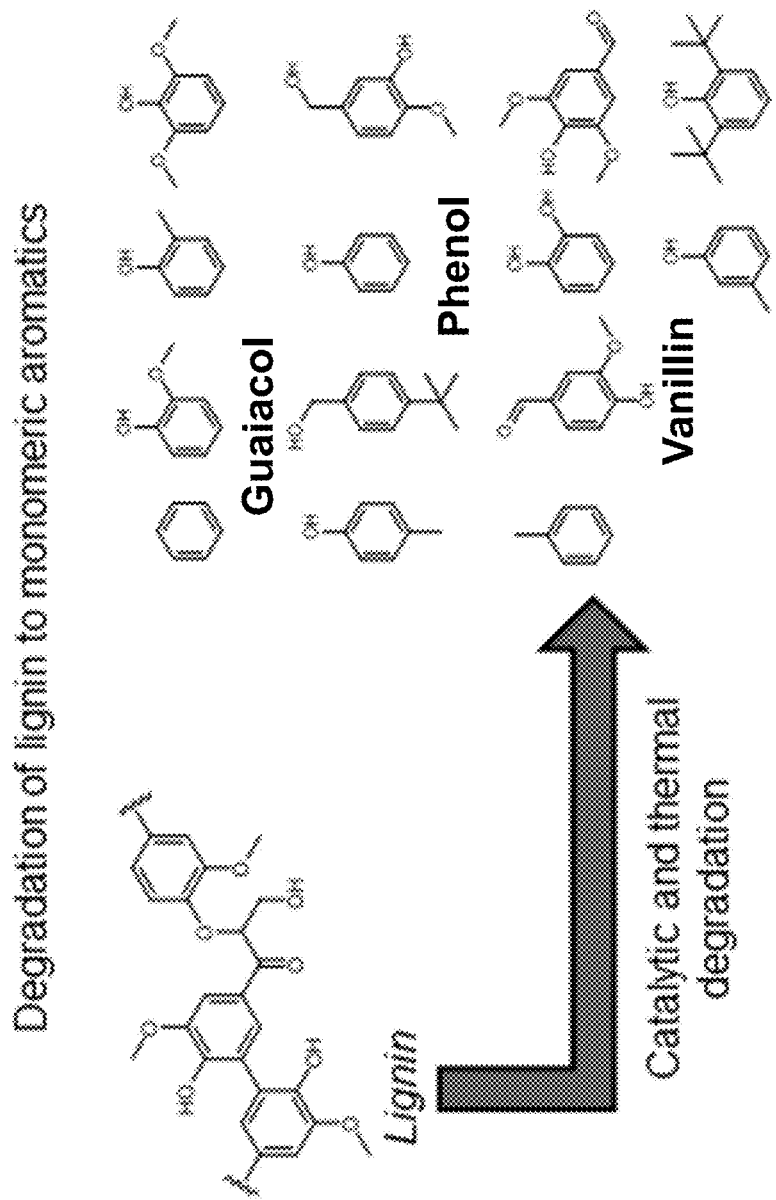

Multiple reaction monitoring of FIG. 7D can be found in FIG. 26. STR: strictosidine synthase.

Figure 12:
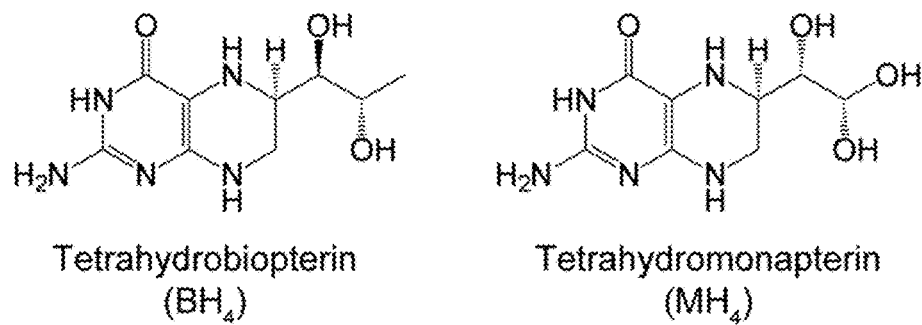

FIG. 12 shows the chemical structures and steriochemistry of BH4 and MH4. Chemical structures of tetrahydrobiopterin ($BH_4$), the natural amino acid mono-oxygenase co-factor, and tetrahydromonapterin ($MH_4$), the $BH_4$ analogue found in *E. coli*. $BH_4$ and $MH_4$ vary in stereochemistry and composition.

Figure 13A:
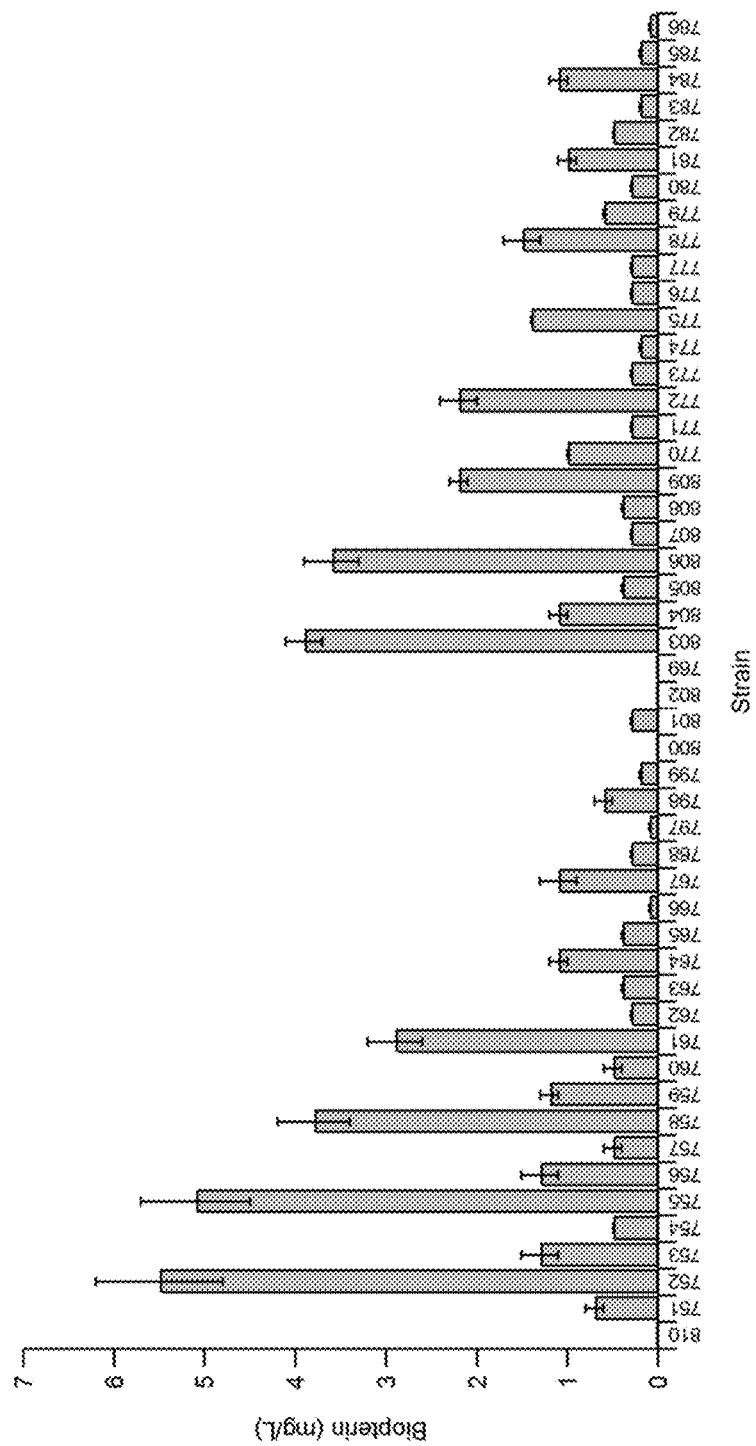
Figure 13B:
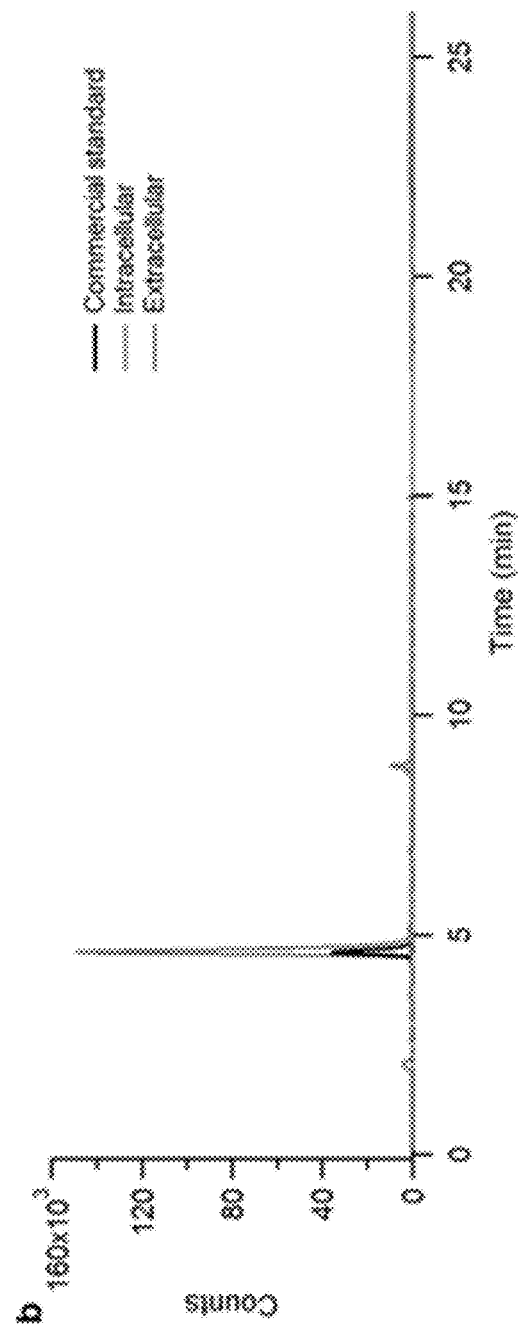

FIGS. 13A and 13B: FIG. 13A shows a graph demonstrating combinatorial production levels of biopterin. Production levels of biopterin were quantified using LC-MS. FIG. 13B shows a full window of the spectra. Production levels reported as 0.00 were either too low to quantify or undetectable. Strain PPY810 represents a control strain expressing green fluorescent protein in a three-plasmid system. The experiments were run in triplicate and shown are the mean and standard deviation.

Figure 14:
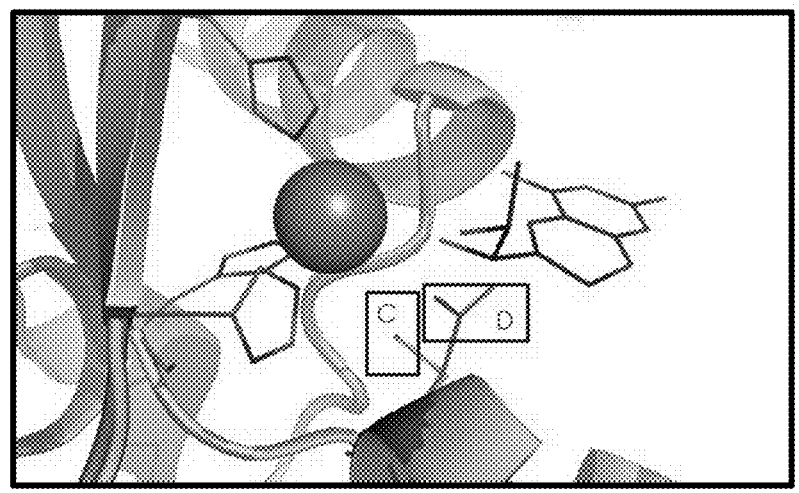

FIG. 14 shows a structural alignment of *Salinibacter ruber* and *Salmo salar* pyruvoyl tetrahydropterin synthase (PTPS). Structural alignment of homology models of *S. salar* PTPS (cyan) and *S. ruber* (green) PTPS obtained via structural homology to rat PTPS (PDB:1B66) using SWISS-MODEL[3-5]. Presented is a monomer of the active site of PTPS (which is composed of three monomers) showing the catalytic cysteine residue of *S. salar* PTPS and corresponding aspartate residue of *S. ruber* PTPS. Biopterin (blue) and Zn(II) (purple) were obtained from the crystal structure from rat. Alignment was completed with PyMOL.

Figure 15:
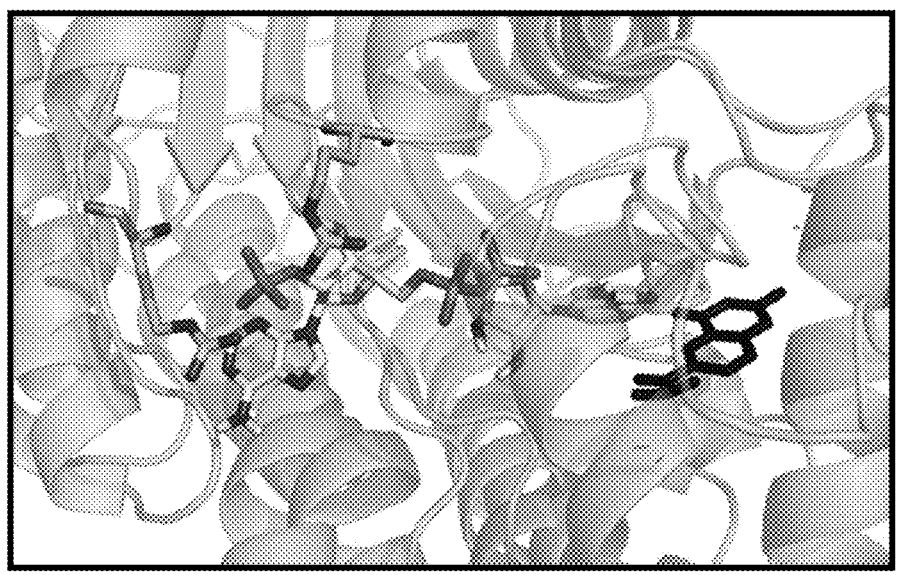

FIG. 15 shows a structural alignment of *Mortirella alpina* and *Thalassiosira pseudonana* sepiapterin reductase (SR). Structural alignment of homology models of *M. alpina* SR (green) and *T. pseudonana* (cyan) SR obtained via structural homology to PDB:1Z6Z and 3ICC, respectively, using SWISS-MODEL[3-5] NADPH (yellow) and biopterin (dark blue) were obtained from the crystal structure of mouse SR (PDB:1SEP). While arginine residues are present in the *M. alpina* structure to stabilize the phosphate group of NADPH, there are no stabilizing residues present in the *T. pseudonana* structure. Alignment was completed with PyMOL.

Figures 16, 17A:
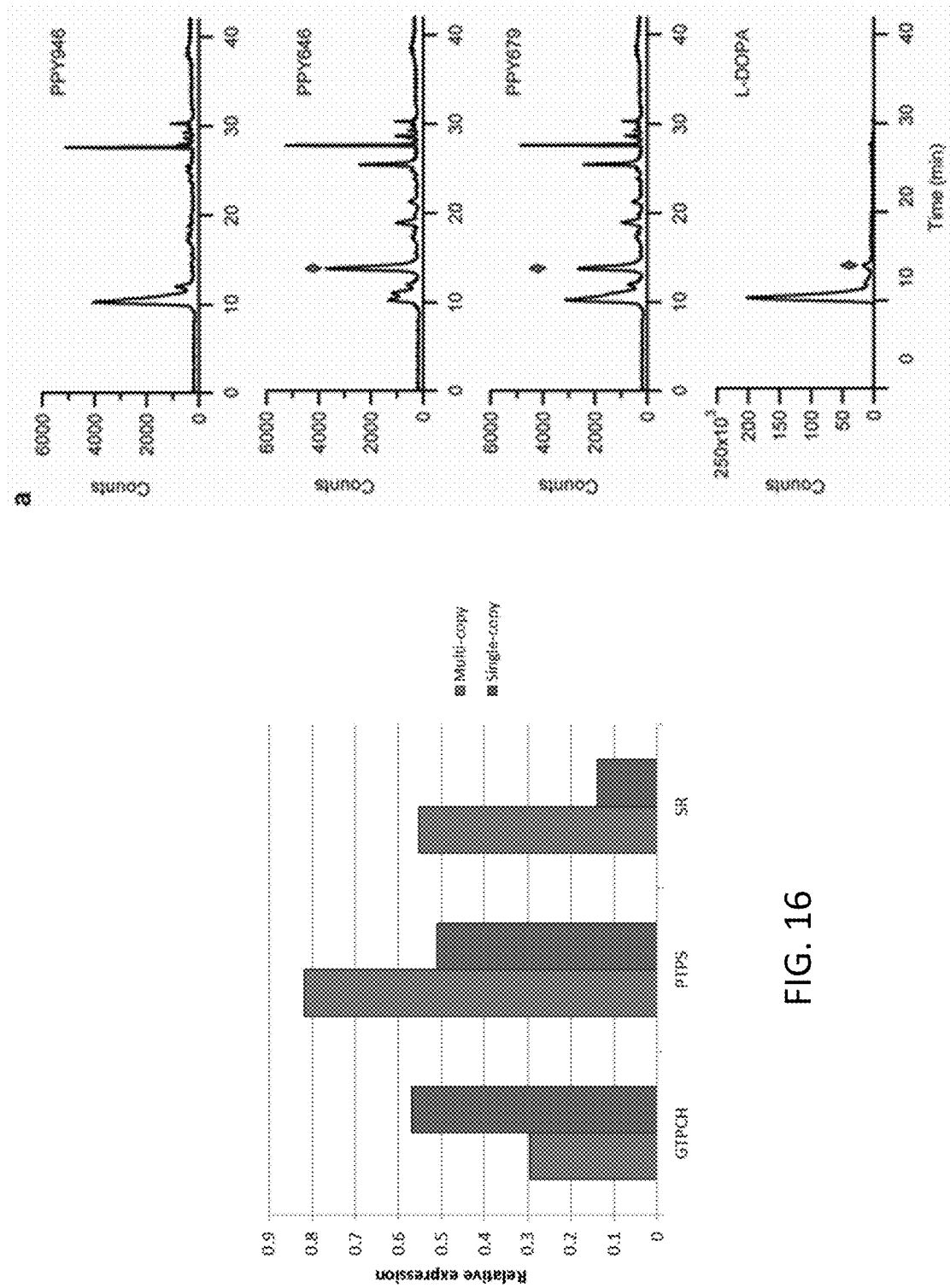

FIG. 16 shows a graph demonstrating GTPCH, PTPS and SR mRNA levels. Multi-copy: multi-copy plasmid. Single-copy: single-copy plasmid. Values represent the mean of two reactions.

Figure 4:
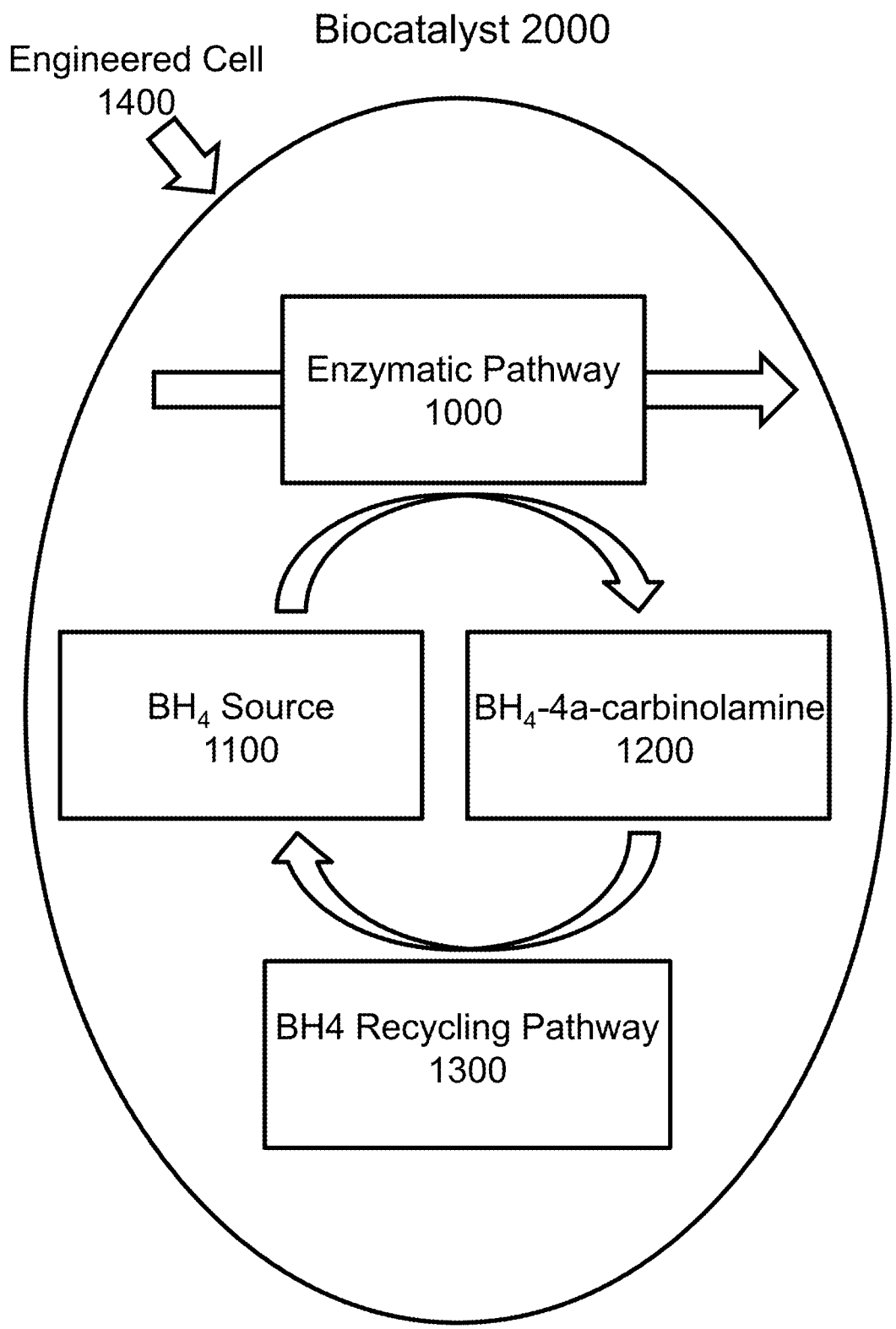
FIG. 4 shows a representative diagram of a cell 1400, which can contain an enzymatic pathway 1000 biologically coupled to a BH4 source 1100 and an optional BH4 recycling pathway 1300.
Figure 5A:
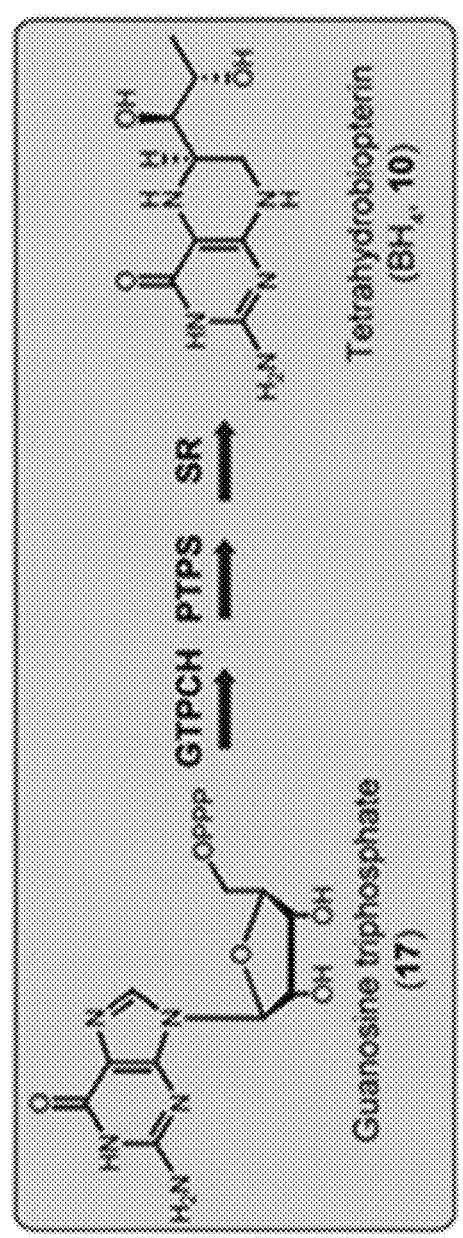
FIGS. 5A-5C demonstrate pterin-dependent synthesis of monoterpene indole alkaloids (MIAs) in *Saccharomyces cerevisiae*. Embodiments of cells, such as of *S. cerevisiae*, described herein can contain one or more of the following: I) the $BH_4$ biosynthetic pathway, II) the $BH_4$ recycling pathway, III) a pterin-dependent mono-oxygenase, IV) a decarboxylase, or V) a Pictet-Spenglerase. Grey arrows represent future potential of the system. GTPCH: GTP cyclohydrolase; PTPS: pyruvoyl tetrahydropterin synthase; SR: sepiapterin reductase; PCD: pterin-4a-carbinolamine dehydratase; DHPR: dihydropteridine reductase; TPH: tryptophan hydroxylase; TH: tyrosine hydroxylase; DDC: aromatic-L-amino-acid decarboxylase; STR: strictosidine synthase.
Figure 5B:
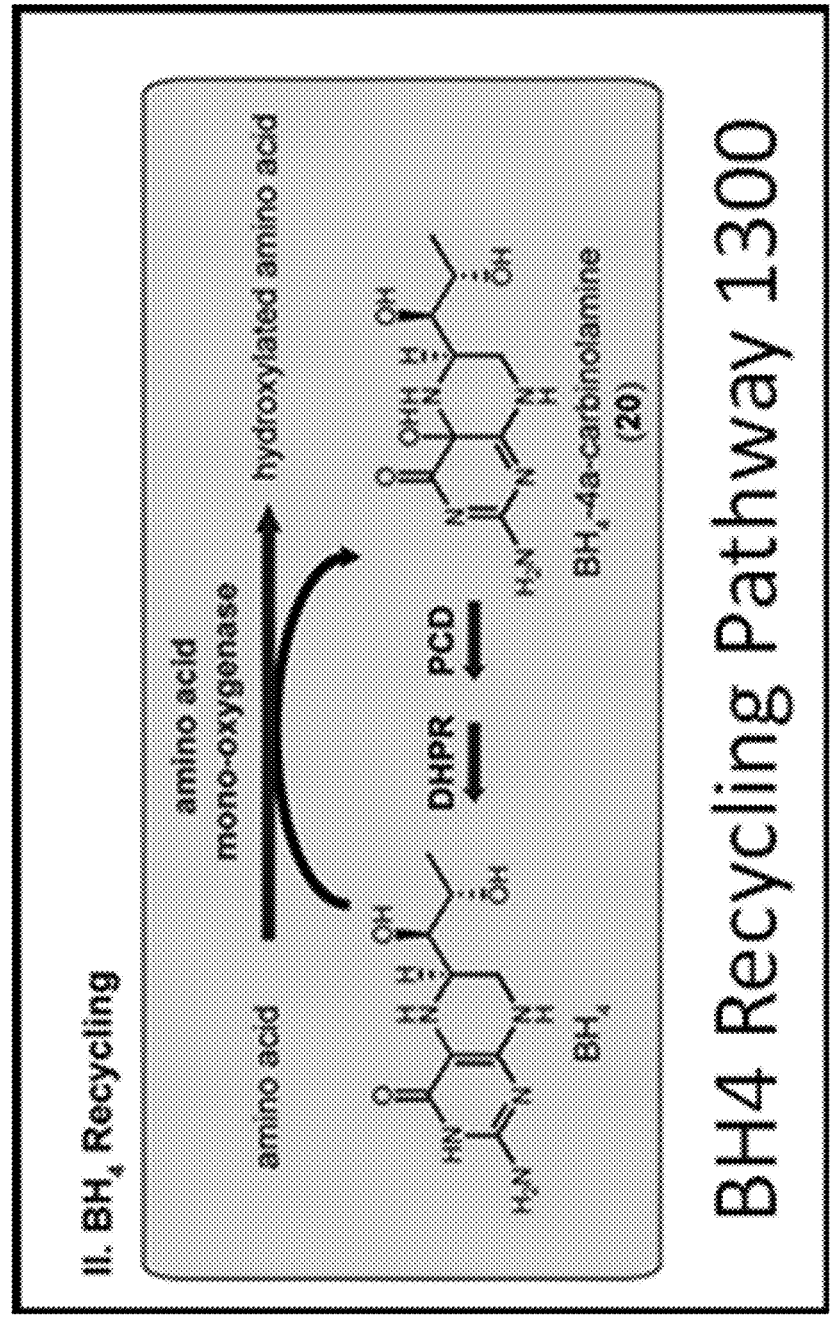
Figures 17B, 17C:
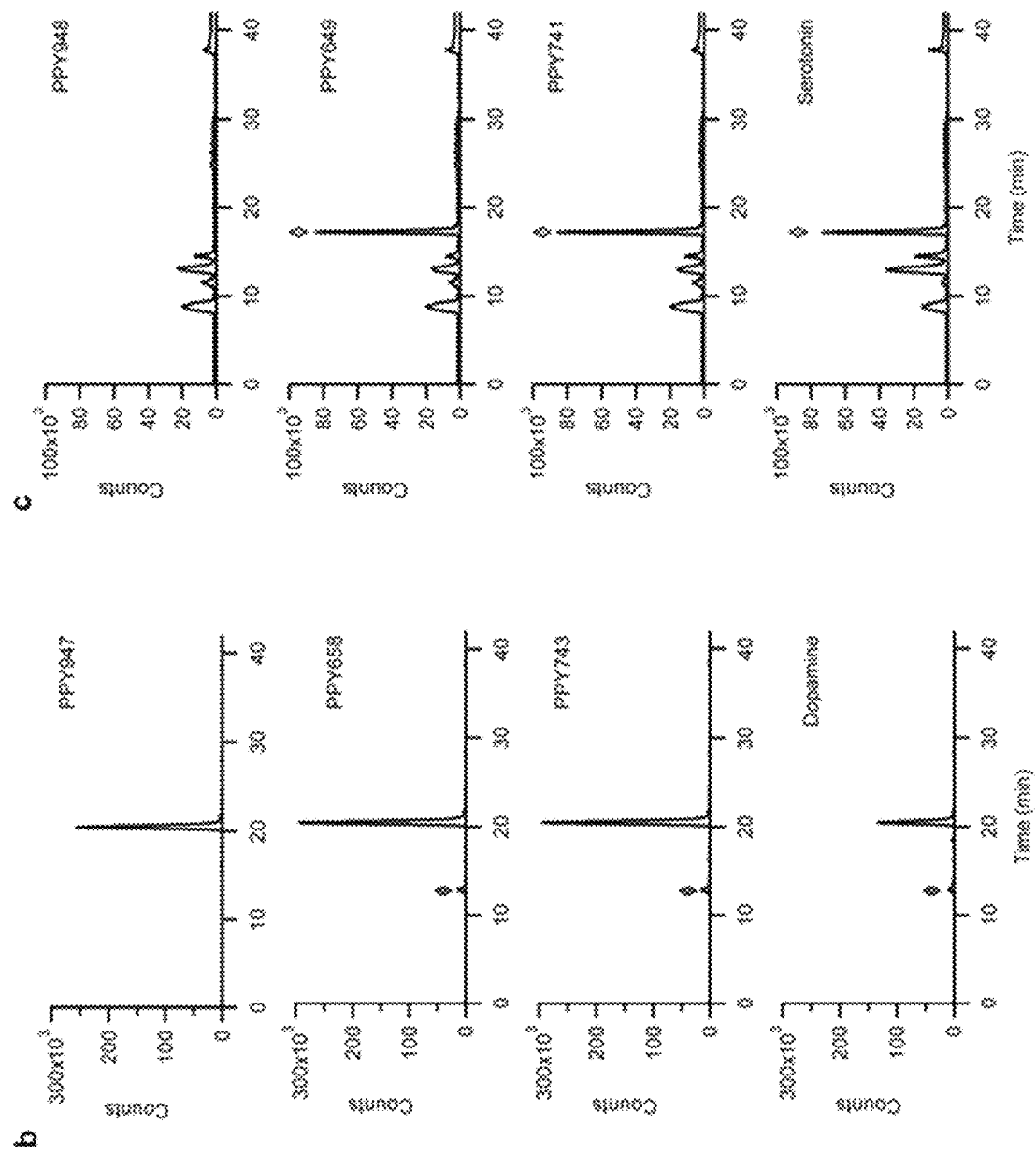

FIGS. 17A-17C show full windows of LC traces in FIGS. 4B, 5B, 5F. L-DOPA, dopamine and serotonin highlighted with a pink (L-DOPA, dopamine) or green diamond (serotonin). (a) L-DOPA (13.8 min), (b) dopamine (12.8 min), and (c) serotonin (17.2 min).

Figure 18:
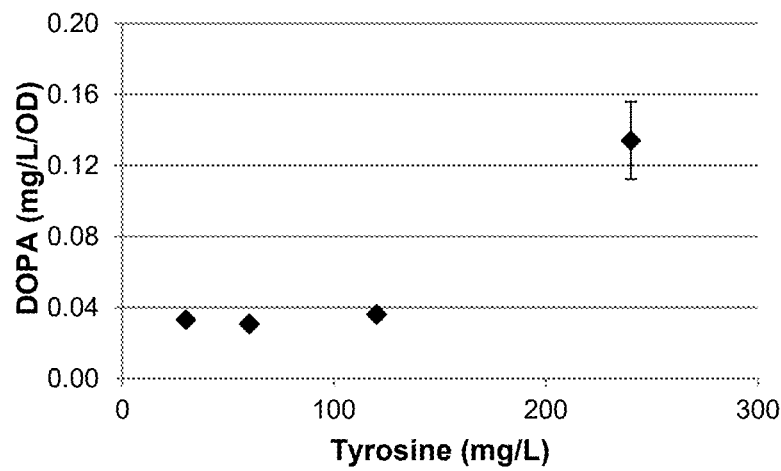

FIG. 18 shows a graph demonstrating the effect of tyrosine on L-DOPA production. In our experiments, 30 mg/L of tyrosine is present when producing L-DOPA or dopamine.

Figure 19:
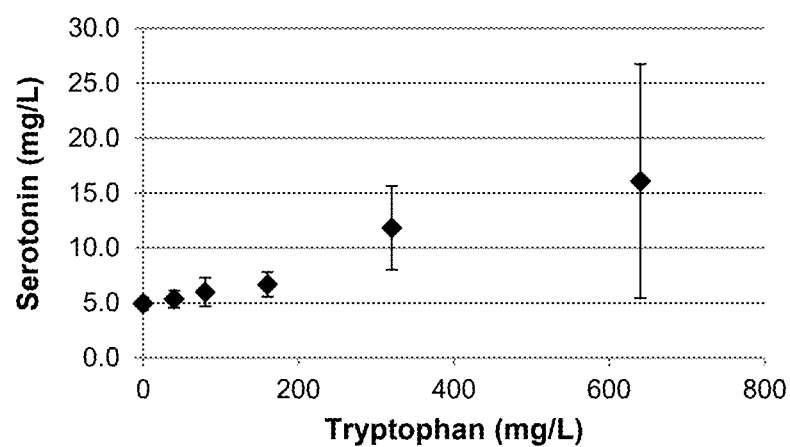

FIG. 19 shows a graph demonstrating the effect of tryptophan on serotonin production. In our experiments, tryptophan is not supplemented when producing serotonin or hydroxystrictosidine.

Figure 20:
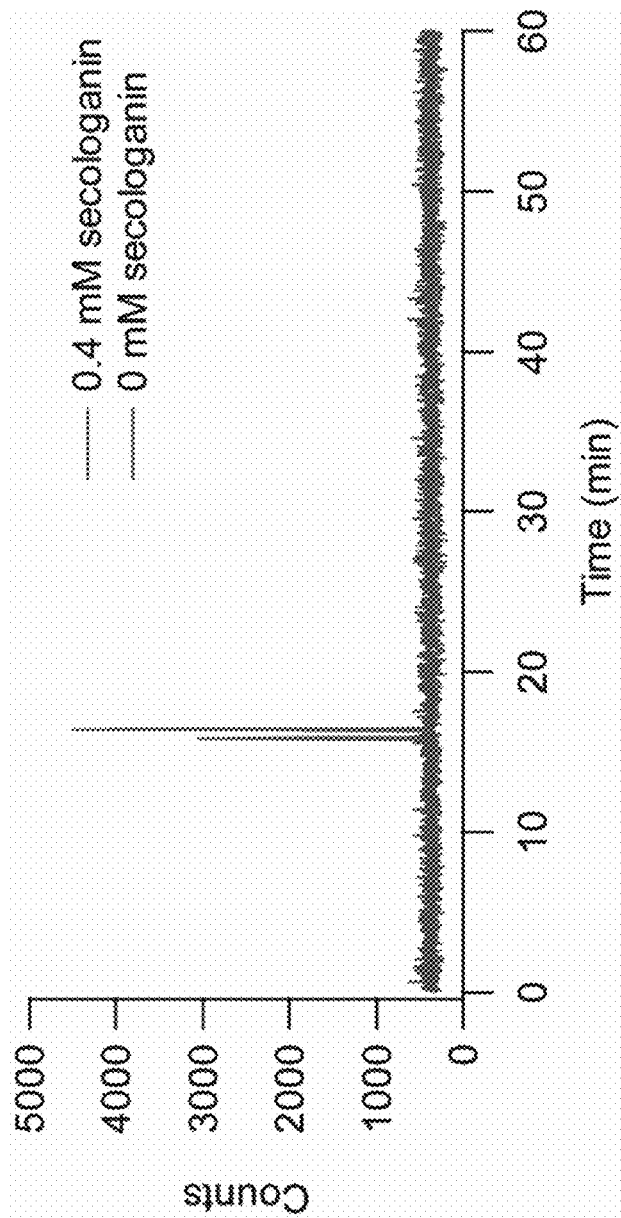
Figure 21A:
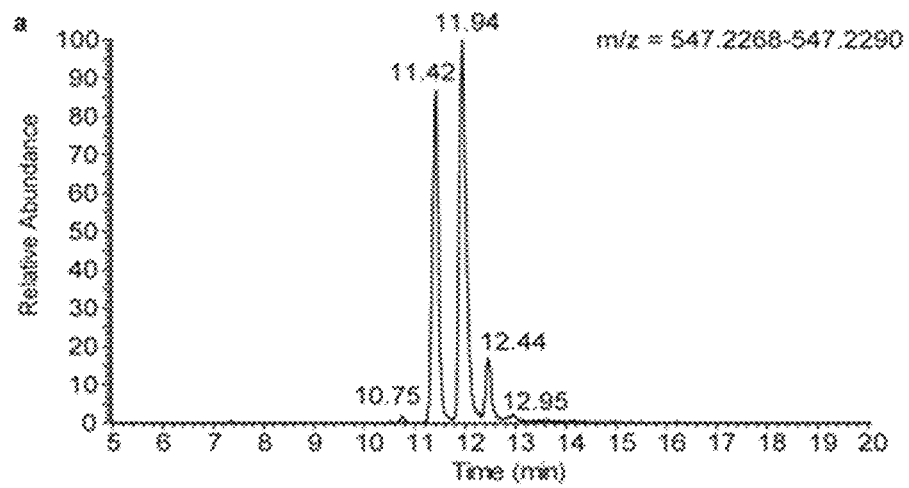
Figure 21B:
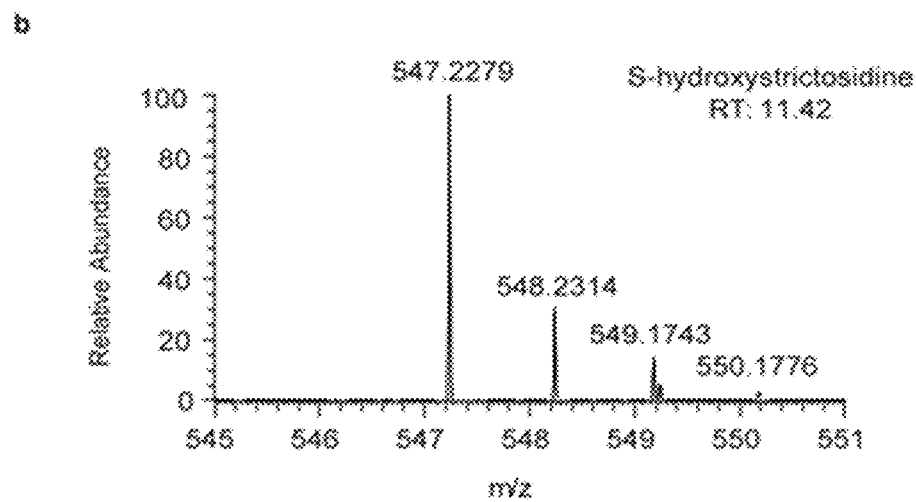
Figure 21C:
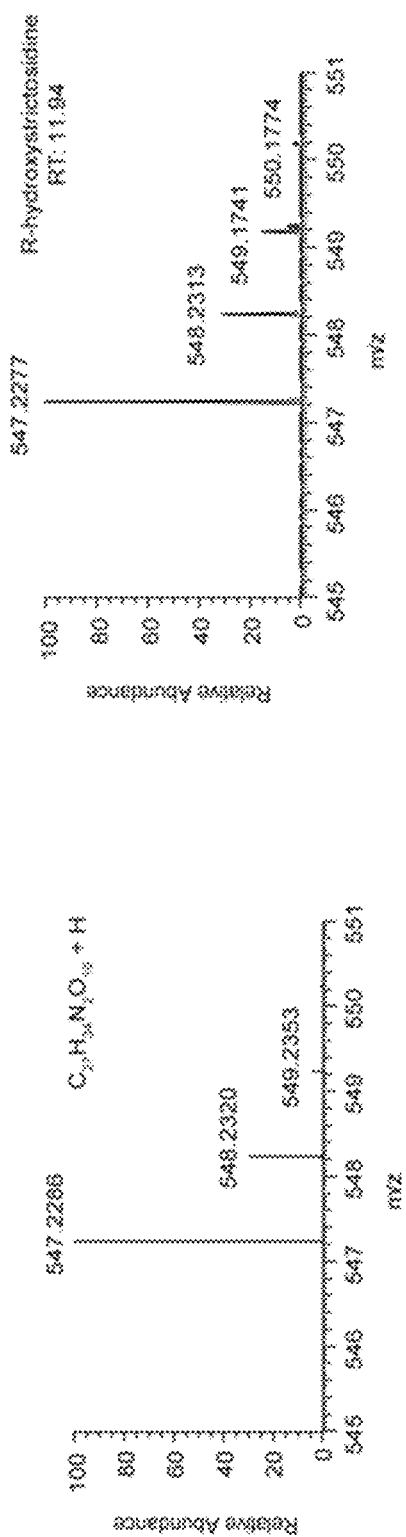
Figure 21D:
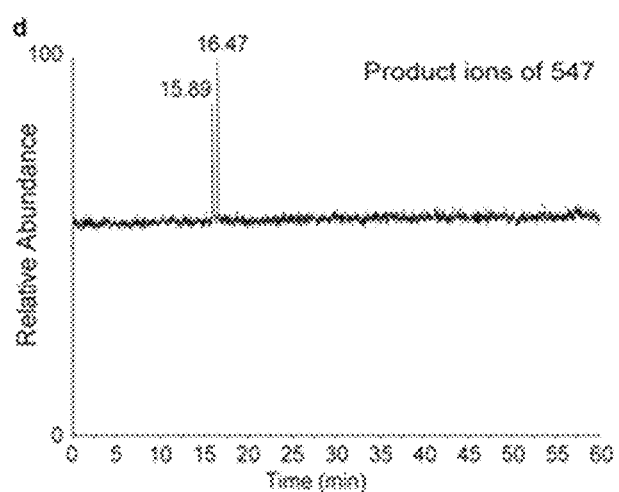
Figure 21E:
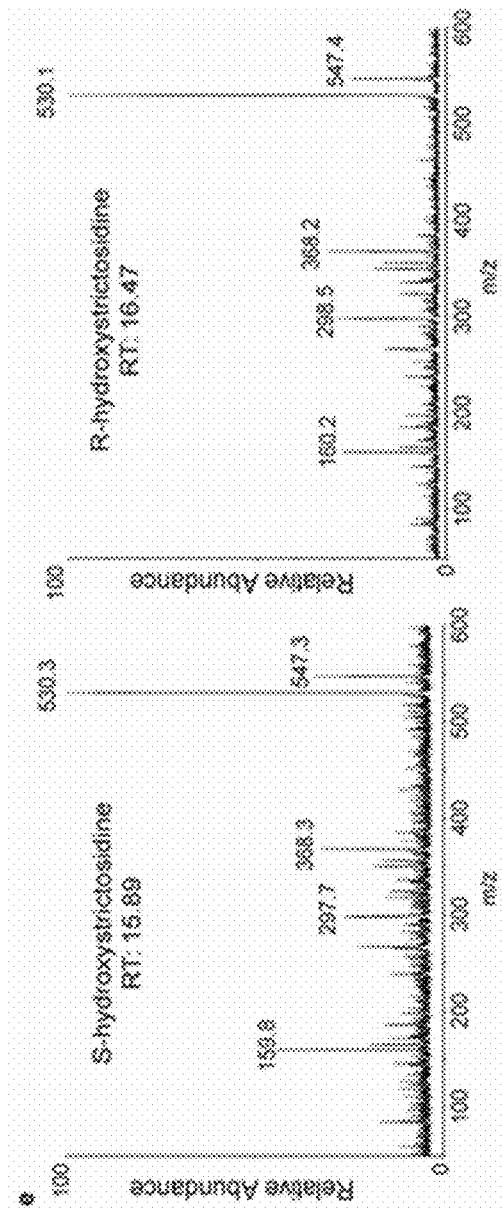

FIG. 20 shows a full window of multiple reaction monitoring for FIG. 6B. Shown hydroxystrictosidine transition: 547.60→530.00 transition.

FIGS. 21A-21E show the graphical results from mass spectral characterization of hydroxystrictosidine isomers. (a) LC trace (extracted ion chromatogram corresponding to hydroxystrictosidine, m/z 547, extracted from full scan data) from high resolution mass spectrometry analysis. (b) High-resolution mass spectrum of microbially-produced 5-hydroxystrictosidine and R-hydroxystrictosidine. (c) Theoretical high-resolution mass spectrum of hydroxystrictosidine. (d) LC trace for product ions of m/z 547 from tandem mass spectrometry analysis. (e) Tandem mass spectra of microbially-produced S-hydroxystrictosidine and R-hydroxystrictosidine.

Figure 22:
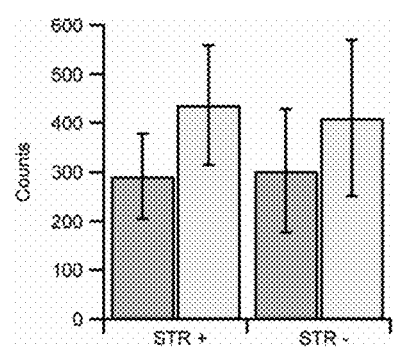

FIG. 22 shows a graph demonstrating isomer ratios produced in the presence (STR +, PPY650) or absence (STR −, PPY649) of strictosidine synthase using yeast synthetic media (pH=5-3). Green: S-hydroxystrictosidine; Yellow: R-hydroxystrictosidine.

FIGS. 23A-23D show full windows of LC traces in FIG. 7 (extracted ion chromatograms for hydroxystrictosidine, m/z 547). S-hydroxystrictosidine, rt=6.1 min. R-hydroxystrictosidine, rt=6.8 min. Isomer identification was determined due to the fact that strictosidine synthase is known to form only the S-isomer. A single isomer is formed in vivo in buffered synthetic media (pH=7→5).

Figure 24A:
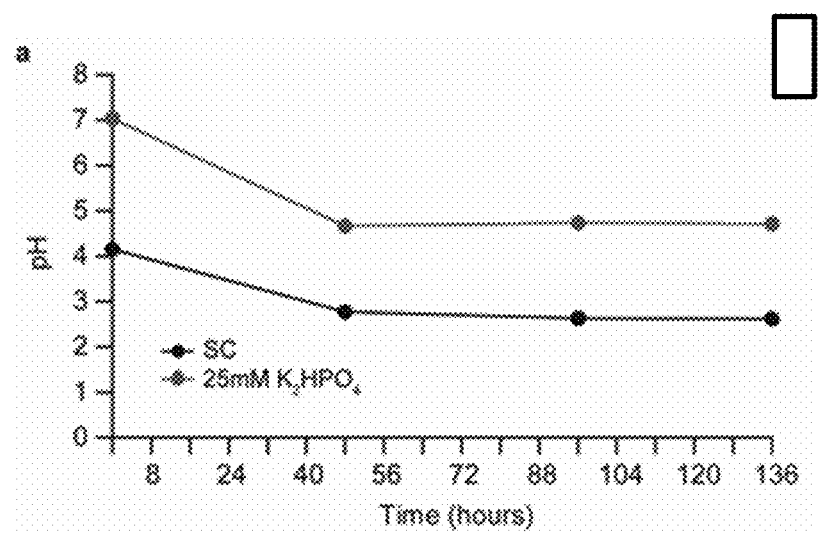
Figure 24B:
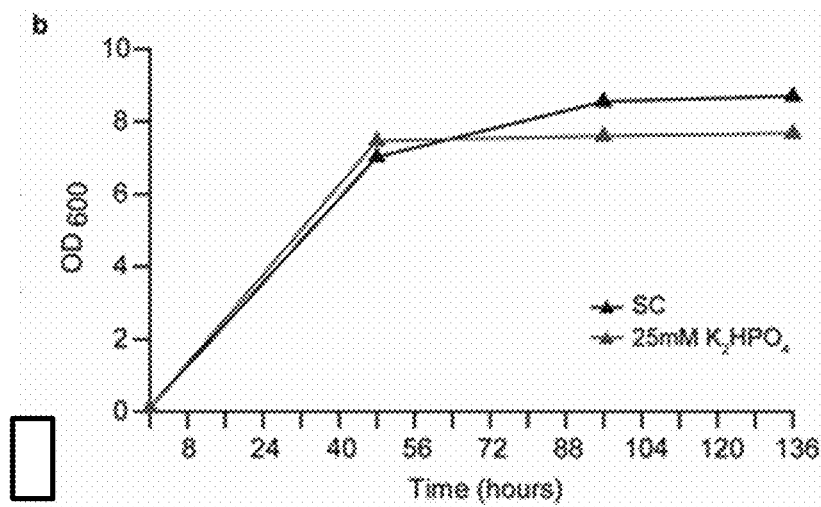

FIGS. 24A-24B show graphs of pH of media over time and cell growth. (a) pH of wild-type W303 yeast grown in synthetic complete media (black) or buffered synthetic complete media (25 mM $K_2HPO_4$, red). (b) Cell growth monitored by absorption at $OD_{600}$.

Figure 25:
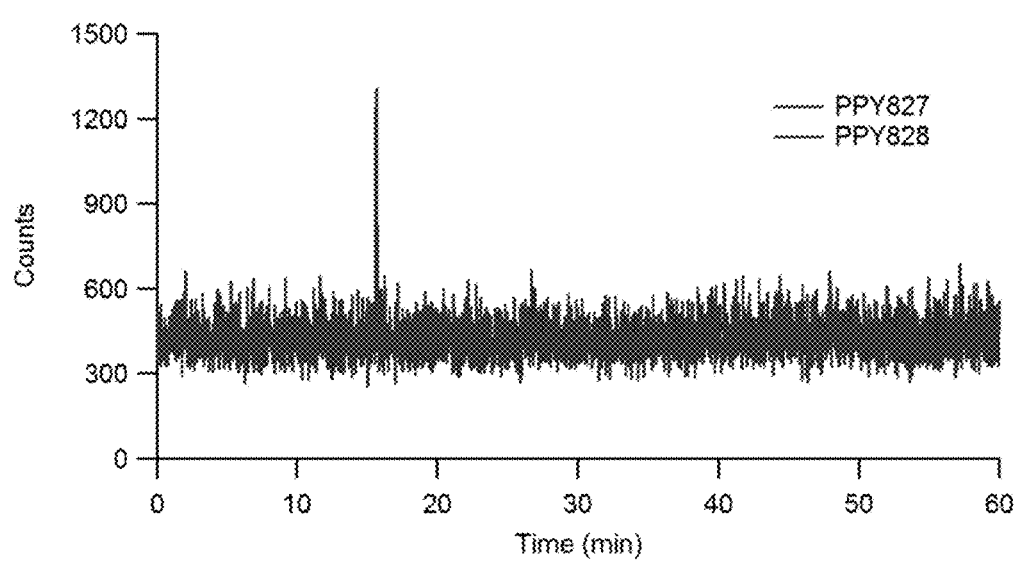

FIG. 25 shows a full window for multiple reaction monitoring (MRM) analysis for FIG. 7D. Only one peak can be found in the MRM spectrum corresponding to the characteristic hydroxystrictosidine transition 547.60→530.00. All other peaks in the FIG. 7D (and SI FIG. 13B) LC trace have m/z value of 547, but do not have the characteristic hydroxystrictosidine transition 547.60→530.

FIG. 26 demonstrates current techniques for the breakdown of lignin lead to the production of low-molecular weight monomeric aromatic units such as those shown here. Many of these are commonly used and, due to their ready availability, they tend to be very cheap, with many been only cents per gram.

Figure 27A:
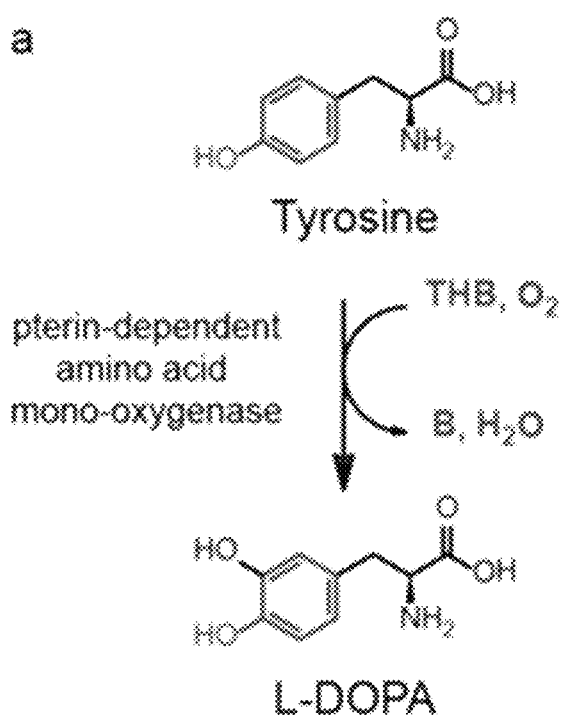
Figure 27B:
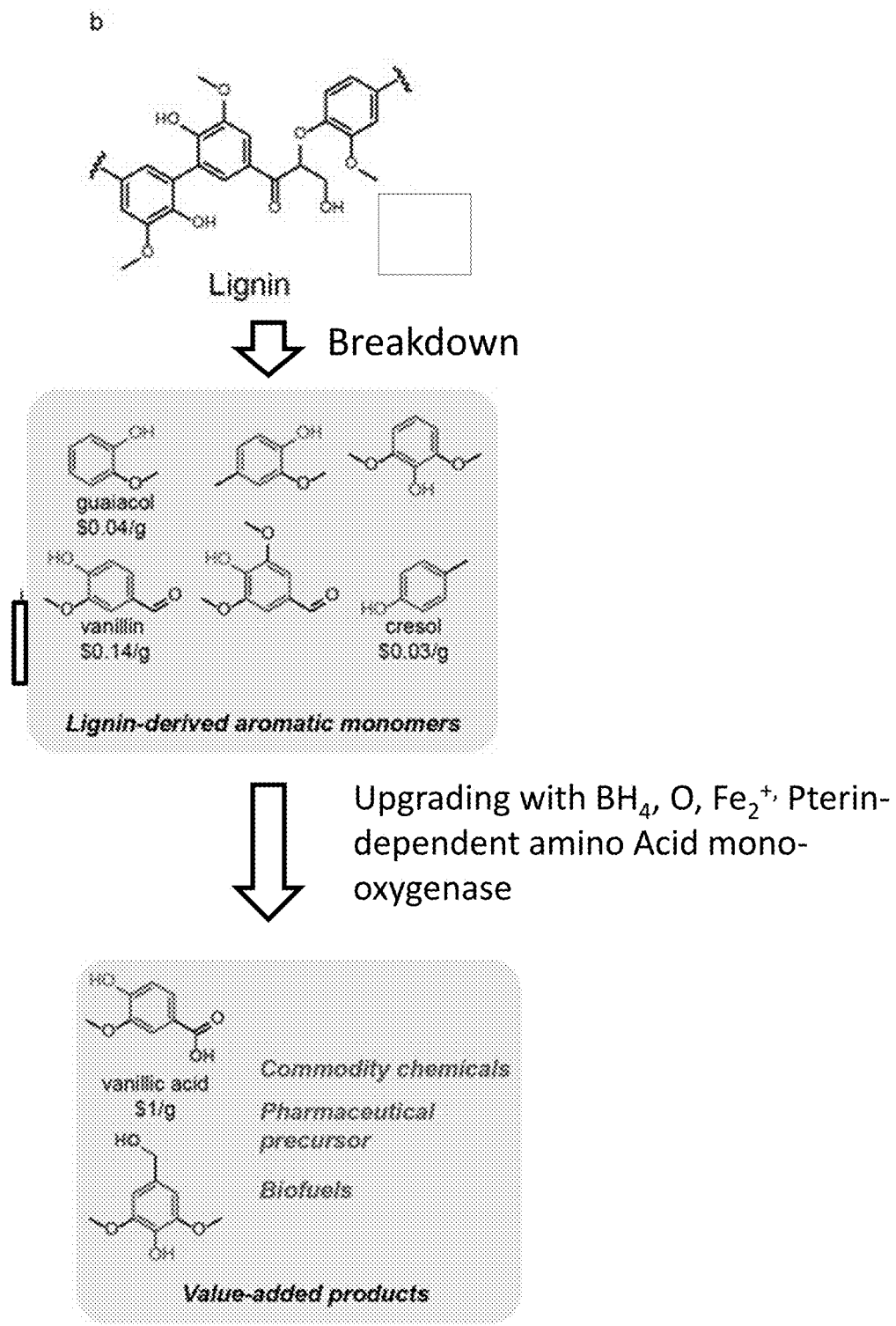

FIGS. 27A-27B show schemes demonstrating upgrading lignin-derived aromatic monomers into value-added chemicals via pterin-based mono-oxygeases. 28A. Pterin-dependent amino acid monooxygenases (AMOs) carry out the hydroxylation of aromatic amino acids. Shown tyrosine monooxygenases hydroxylating tyrosine into L-DOPA. FIG. 27B. The structure of lignin-derived aromatic amino acids is similar to tyrosine.

Figure 28A:
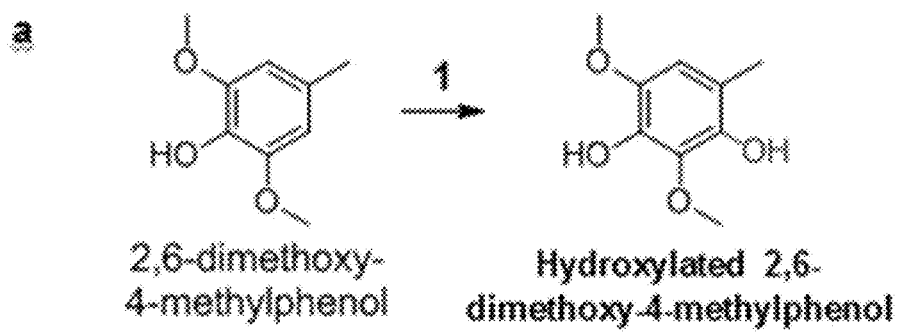
Figure 28B:
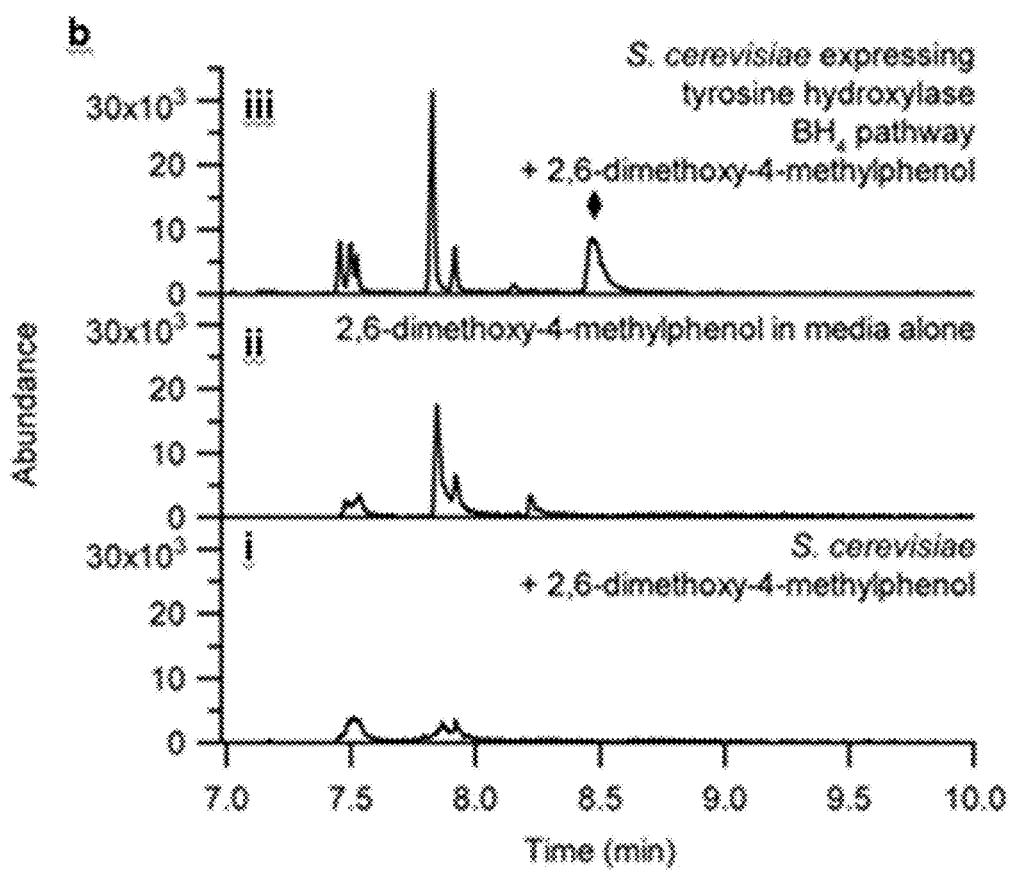

FIGS. 28A-28B demonstrate embodiments of a synthesis scheme (FIG. 28A) and data (FIG. 28B) demonstrating production of 2,6-dimethoxy-4-metholyphenol.

Figure 29:
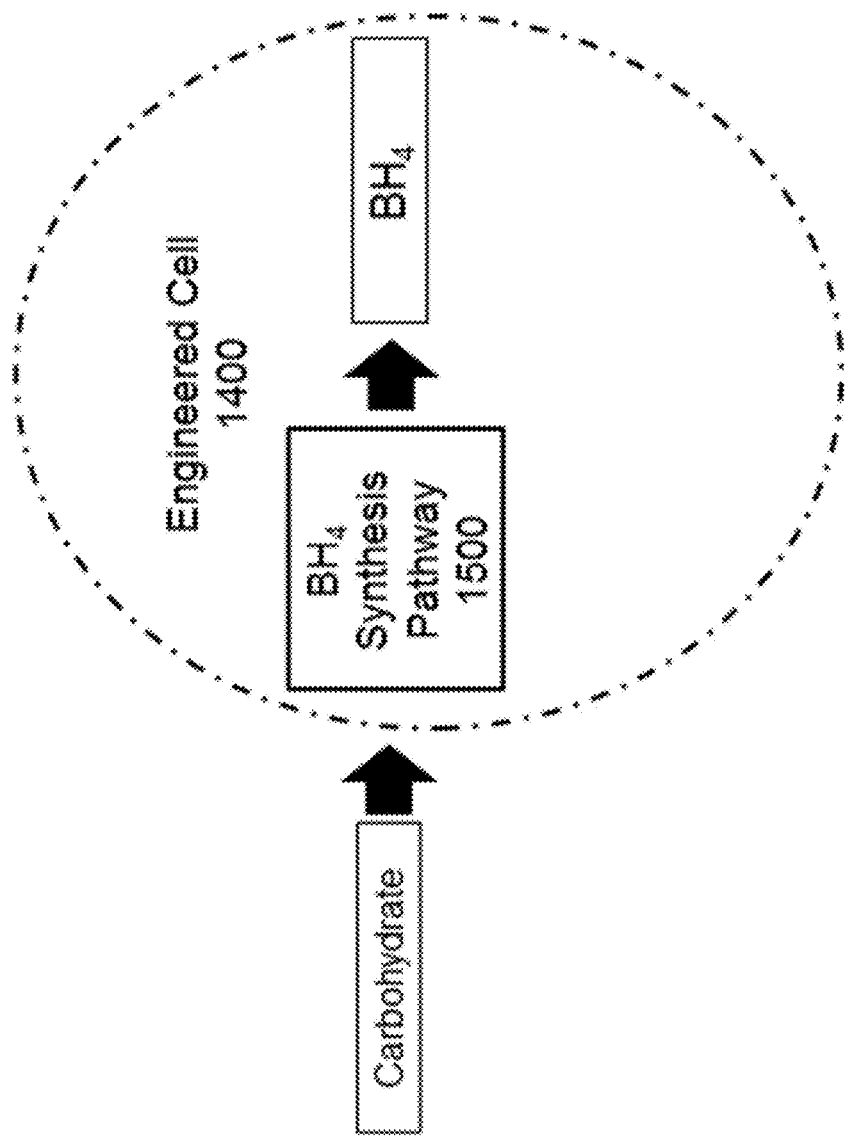

FIG. 29 demonstrates an embodiment of a cell engineered to produce BH4 as described herein. $BH_4$ can be synthesized by a $BH_4$ synthesis pathway 1500 comprising GTP cyclohydrase (GTPCH), pyruvol tetrahydrobiopterin synthase (PTPS), and sepiapterin reductase (SR). A yeast cell is engineered to express said $BH_4$ synthesis pathway. Said engineered yeast cell is incubated with media and a carbohydrate for an amount of time to produce $BH_4$. The carbohydrate can be glucose or galactose. Products of the endogenous yeast carbohydrate metabolic pathway are then used by (or coupled to) the engineered BH4 pathway to produce BH4 in the engineered yeast cell.

Figure 30:
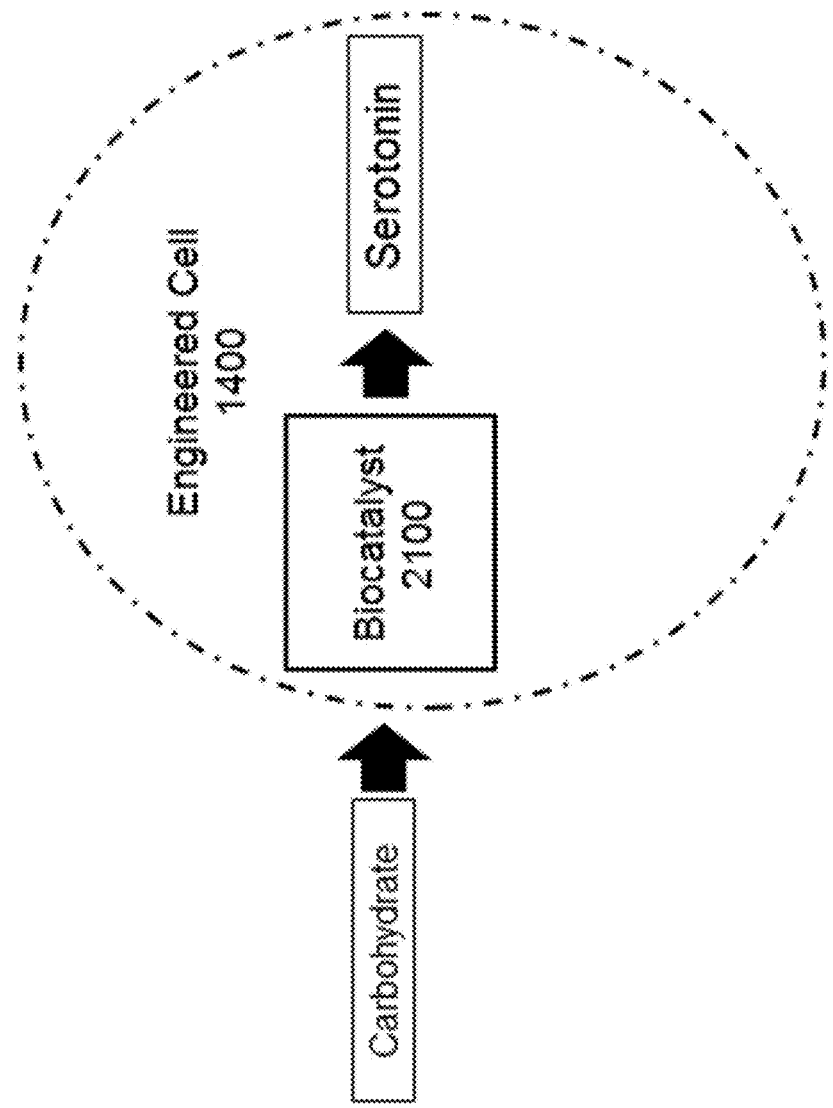

FIG. 30 demonstrates an embodiment of a cell engineered to produce serotonin using a biocatalyst as described herein. The biocatalyst 2100 is comprised of a BH4 synthesis pathway 1500 and an enzymatic pathway 1000 comprised of tryptophan hydroxylase and aromatic-l-amino acid decarboxylase. The engineered yeast cell can be incubated with media and a carbohydrate for an amount of time to produce serotonin. The carbohydrate can be glucose or galactose. Products of the endogenous yeast carbohydrate metabolic pathway are then used by (or coupled to) the biocatalyst 2100 to produce serotonin in the engineered yeast cell.

Figure 31:
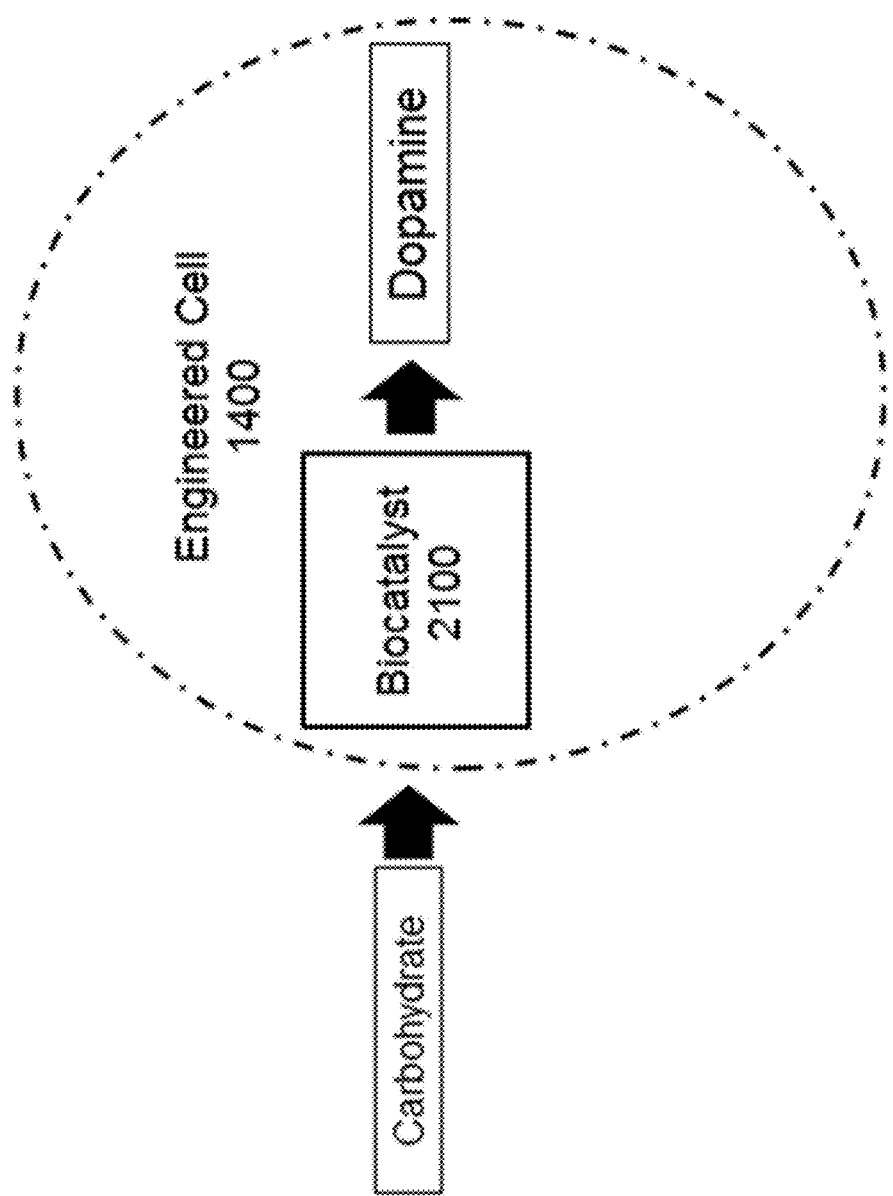

FIG. 31 demonstrates an embodiment of a cell engineered to produce dopamine from a carbohydrate using a biocatalyst as described herein.

Figure 32:
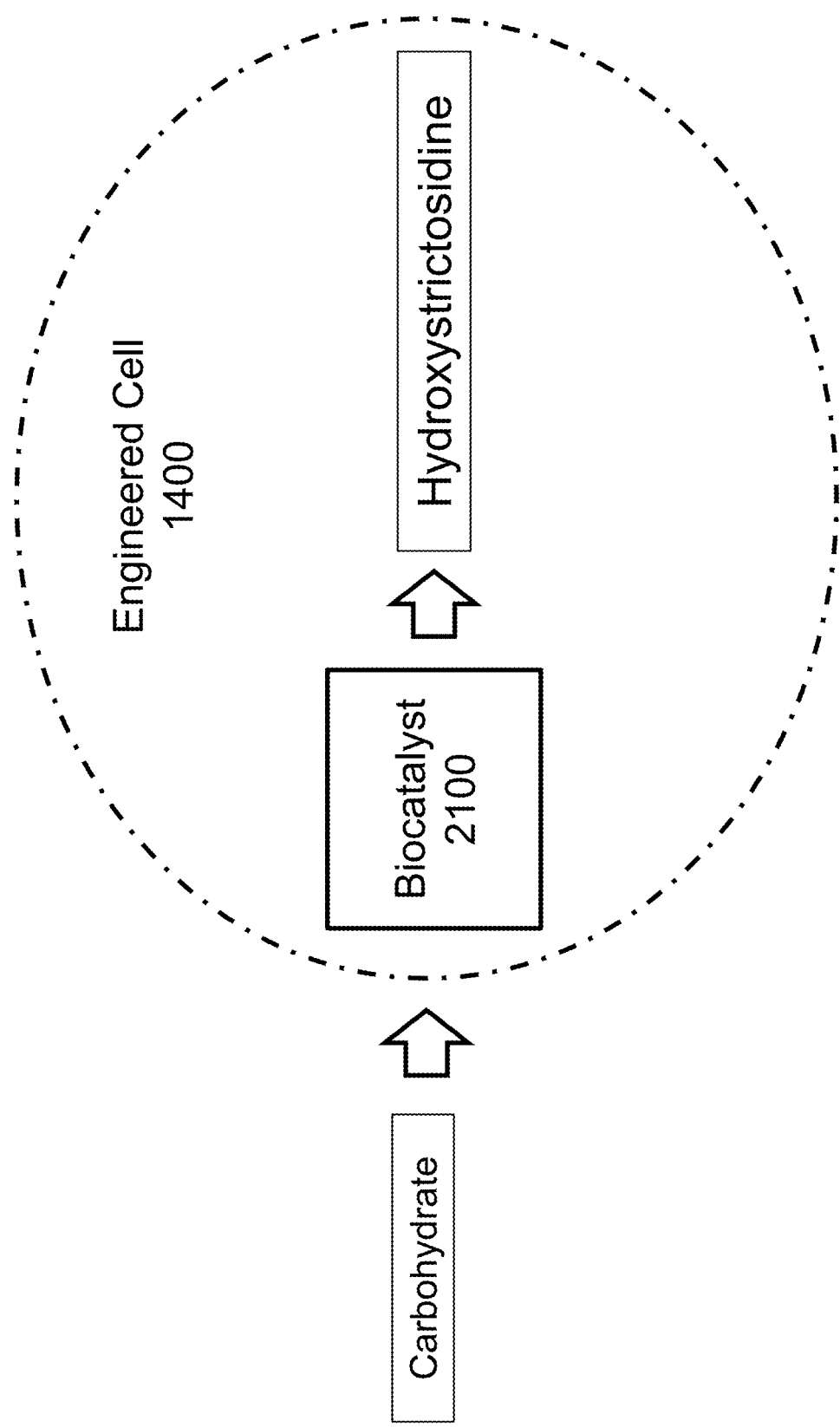

FIG. 32 demonstrates an embodiment of a cell engineered to produce hydroxystrictosidine from a carbohydrate as described herein.

FIG. 33 shows a table demonstrating the overview of the microbial synthesis of L-DOPA, dopamine, serotonin and 10-hydroxystrictosidine. Arrows represent presence of the enzyme. nd=not detectable. Amount produced is represented by the mean±standard deviation for samples run in triplicate. GTPCH: GTP cyclohydrolase; PTPS: pyruvoyl tetrahydropterin synthase; SR: sepiapterin reductase; PCD: pterin-4a-carbinolamine dehydratase; DHPR: dihydropteridine reductase; TPH: tryptophan hydroxylase; TH: tyrosine hydroxylase; DDC: aromatic-L-amino-acid decarboxylase; STR: strictosidine synthase.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, synthetic biology, chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within .+−0.10% of the indicated value, whichever is greater.

As used herein, "control" is an alternative subject or sample used in an experiment for comparison purposes and included to minimize or distinguish the effect of variables other than an independent variable.

As used herein, "overexpressed" or "overexpression" refers to an increased expression level of an RNA or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "wild-type" is the typical form of an organism, variety, strain, gene, protein, or characteristic as it occurs in nature, as distinguished from mutant forms that may result from selective breeding or transformation with a transgene.

As used herein, "identity," is a relationship between two or more polypeptide or polynucleotide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch (J. Mol. Biol., 1970, 48: 443-453) algorithm (e.g., NBLAST, and XBLAST). The default parameters are used to determine the identity for the polypeptides or polynucleotides of the present disclosure.

As used herein, "heterologous" refers to compounds, molecules, nucleotide sequences (including genes), and polypeptide sequences (including peptides and proteins) that are different in both activity (function) and sequence or chemical structure. As used herein, "heterologous" can also refer to a gene or gene product that is from a different organism. For example, a human GTP cyclohydrolase or a synthase can be said to be heterologous when expressed in yeast.

As used herein, "homologue" refers to a polypeptide sequence that shares a threshold level of similarity and/or identity as determined by alignment of matching amino acids. Two or more polypeptides determined to be homologues are said to be homologues. Homology is a qualitative term that describes the relationship between polypeptide sequences that is based upon the quantitative similarity.

As used herein, "paralog" refers to a homologue produced via gene duplication of a gene. In other words, paralogs are homologues that result from divergent evolution from a common ancestral gene.

As used herein, "orthologues" refers to homologues produced by speciation followed by divergence of sequence but not activity in separate species. When speciation follows duplication and one homologue sorts with one species and the other copy sorts with the other species, subsequent divergence of the duplicated sequence is associated with one or the other species. Such species-specific homologues are referred to herein as orthologues.

As used herein, "xenologs" are homologues resulting from horizontal gene transfer.

As used herein, "similarity" is a quantitative term that defines the degree of sequence match between two compared polypeptide sequences.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "culturing" refers to maintaining cells under conditions in which they can proliferate and avoid senescence as a group of cells. "Culturing" can also include conditions in which the cells also or alternatively differentiate.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "gene" refers to a hereditary unit corresponding to a sequence of DNA that occupies a specific location on a chromosome and that contains the genetic instruction for a characteristic(s) or trait(s) in an organism.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "plasmid" as used herein refers to a non-chromosomal double-stranded DNA sequence including an intact "replicon" such that the plasmid is replicated in a host cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "operatively linked" or "operatively coupled" indicates that the regulatory sequences useful for expression of the coding sequences of a nucleic acid are placed in the nucleic acid molecule in the appropriate positions relative to the coding sequence so as to effect expression of the coding sequence. This same definition can also be applied to the arrangement of coding sequences and transcription control elements (e.g. promoters, enhancers, and termination elements), and/or selectable markers in an expression vector.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein, "stable expression," "stable incorporation," "stable transfection" and the like refer to the integration of an exogenous gene into the genome of a host cell, which can allow for long term expression of the exogenous gene.

As used herein, "transient expression," "transient transfection," and the like refer to the introduction of an exogenous gene into a host cell that does not result in stable incorporation of the gene into the host cell.

As used herein "chemical" refers to any molecule, compound, particle, or other substance that can be a substrate for an enzyme in the enzymatic pathway described herein and/or a pterin (e.g. BH4) synthesis enzyme or biochemical pathway. A "chemical" can also be used to refer to a metabolite of a carbohydrate or lignin. As such, "chemical" can refer to nucleic acids, proteins, organic compounds, inorganic compounds, metabolites etc. "Chemical" can also refer to the product produced by the biocatalyst.

As used herein "biologically coupled" refers to the association of or interaction between two or more physically distinct molecules, groups of molecules compounds, organisms, or particles where the association is directly or indirectly mediated between the two or more physically distinct molecules, groups of molecules compounds, organisms or particles via a biologic molecule or compound. This can include direct binding between two biologic molecules and signal transduction pathways.

As used herein, "biological communication" refers to the communication between two or more molecules, compounds, or objects that is mediated by a biologic molecule or biologic interaction.

As used herein, "biologic molecule," "biomolecule," and the like refer to any molecule that is present in a living organism and includes without limitation, macromolecules (e.g. proteins, polysaccharides, lipids, and nucleic acids) as well as small molecules (e.g. metabolites and other products produced by a living organism).

As used herein, "regulation" refers to the control of gene or protein expression or function.

As used herein, "promoter" refers to the DNA sequence(s) that control or otherwise modify transcription of a gene and can include binding sites for transcription factors, RNA polymerases, and other biomolecules and substances (e.g. inorganic compounds) that can influence transcription of a gene by interaction with the promoter. Typically these sequences are located at the 5' end of the sense strand of the gene, but can be located anywhere in the genome.

As used herein, "native" refers to the endogenous version of a molecule or compound relative to the host cell or population being described.

As used herein, "non-naturally occurring" refers to a non-native version of a molecule or compound or non-native expression or presence of a molecule or compound within a host cell or other composition. This can include where a native molecule or compound is influenced to be expressed or present at a different location within a host, at a non-native period of time within a host, or is otherwise in an altered environment, even when considered within the host. Non-limiting examples include where a protein that is expressed only in the nucleus of a cell is expressed in the cytoplasm of the cell or when a protein that is only normally expressed during the embryonic stage of development is expressed during the adult stage.

As used herein, "encode" refers to the biologic phenomena of transcribing DNA into an RNA that, in some cases, can be translated into a protein product. As such, when a protein is said herein to be encoded by a particular nucleotide sequence, it is to be understood that this refers to this biologic relationship between DNA and protein. It is well established that RNA can be translated into protein based on the triplet code where 3 nucleotides represent an amino acid. This term also includes the idea that DNA can be transcribed into RNA molecules with biologic functions, such as ribozymes and interfering RNA species. As such, when a RNA molecule is said to be encoded by a particular nucleotide sequence it is to be understood that this is referring to the transcriptional relationship between the DNA and RNA species in question. As such "encoding nucleotide" refers to herein as the nucleotide which can give rise through transcription, and in the case of proteins, translation a functional RNA or protein.

As used herein, biocatalyst can refer to a single enzyme or pathway containing one or more enzymes and/or other proteins or other components that is configured to carryout, initiate, and/or modify the rate of a chemical or biochemical reaction in an organism, cell, or in-vitro cell free system.

As used herein, biocatalysis can refer to the catalysis carried out in an organism or cells, or in-vitro cell free system, by a biocatalyst.

As used herein, "pterin-dependent" can refer to the requirement of an enzyme for a pterin co-factor for the enzymatic catalysis that is mediated by the enzyme to occur. "Pterin-dependent" can thus also refer to a biochemical pathway that contains an enzyme that is pterin-dependent.

As used herein "codon optimized" or "codon optimization" refers to a codon modification or making modifications to the codons for amino acids in a polypeptide such that they reflect the codon usage bias of the cell type that the polypeptide is expressed in. Modifications to the codons can be made using techniques generally known in the art.

Discussion

Current techniques for synthesis of complex pharmaceutical compounds rely on isolation of enantiopure starting or intermediate compounds from plants, a challenging and expensive endeavor due to low tissue accumulation and purification complexities. Compounds from plants are also high in aromatic content, presenting additional challenges for the synthesis of target compounds. For example, lignin derived aromatic compounds are extremely difficult to modify, which significantly increases their cost and reduces their applications.

With the limitations of current techniques in mind, described herein is a biocatalyst that can contain a pterin source (which can be tetrahydrobiopterin, or $BH_4$) and a pterin-dependent enzymatic pathway. the biocatalyst can optionally a pterin recycling pathway. The biocatalyst described herein can synthesize non-natural amino acids, hydroxylated aromatics, neurotransmitters, neurotransmitter metabolites, and alkaloids using a direct and selective reaction step. The synthetic products of the system can be produced from a carbohydrate substrate, such as glucose or galactose. The biocatalyst can be optionally expressed and/or exist in an artificial cell-free system. The biocatalyst can be expressed and operate within a cell. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Biocatalysts

Described herein is a biocatalyst 2000 that can contain physically distinct components that are biologically coupled to and/or in biologically communication with each other. The biocatalyst can be expressed and operate independently in a cell-free environment and can be expressed and operate within a cell. The cell can be engineered to express one or more of the components, individually or in combination, of the biocatalyst system 2000 described herein.

Figure 1:
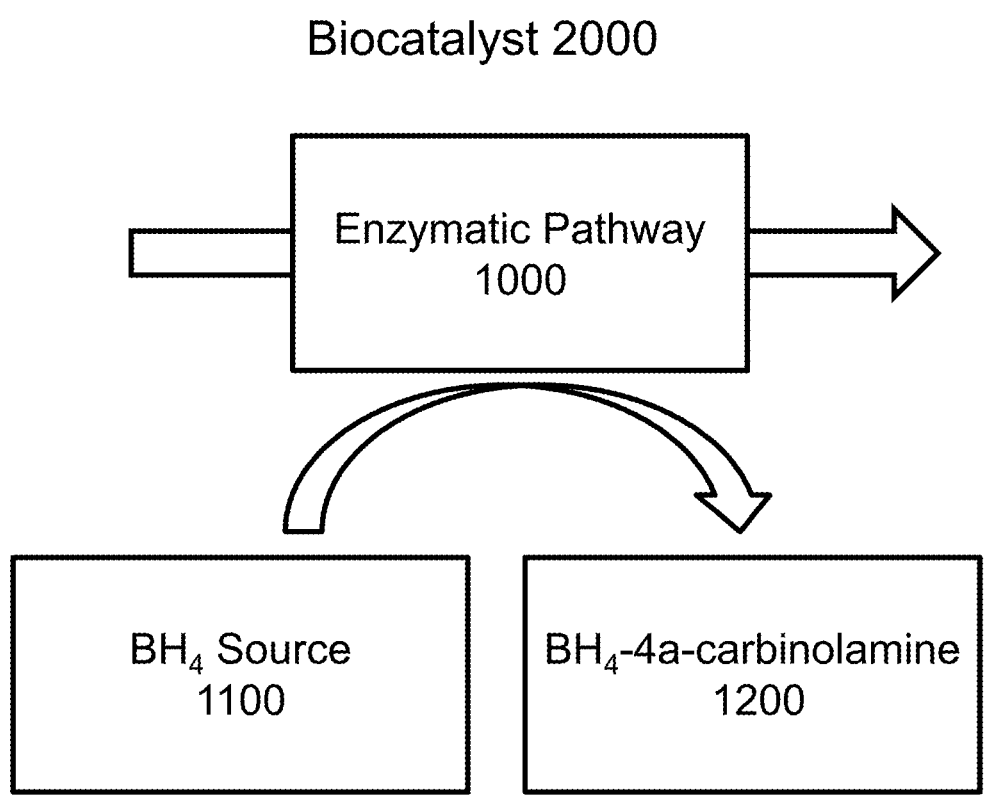
FIG. 1 shows a representative diagram of some embodiments of a biocatalyst 2000 containing an enzymatic pathway 1000 coupled to a BH4 source 1100.

An overview of the biocatalyst is presented in FIGS. 1-4. The biocatalyst can contain an enzymatic pathway 1000 coupled to a BH4 source 1100 (FIG. 1). The enzymatic pathway 1000 can utilize tetrahydrobiopterin (herein referred to as BH4 or $BH_4$) from a BH4 source 1100 as a cofactor. As the enzymatic reaction of the enzymatic pathway 1000 progresses, BH4 used by the enzymatic pathway 1000 is converted into BH4-4a-carbinolamine 1200. Tetrahydromonapterin ($MH_4$), is another pterin that can be used. The enzymatic pathway 1000 can optionally be omitted for a biocatalyst where BH4 is the only desired product.

Figure 2:
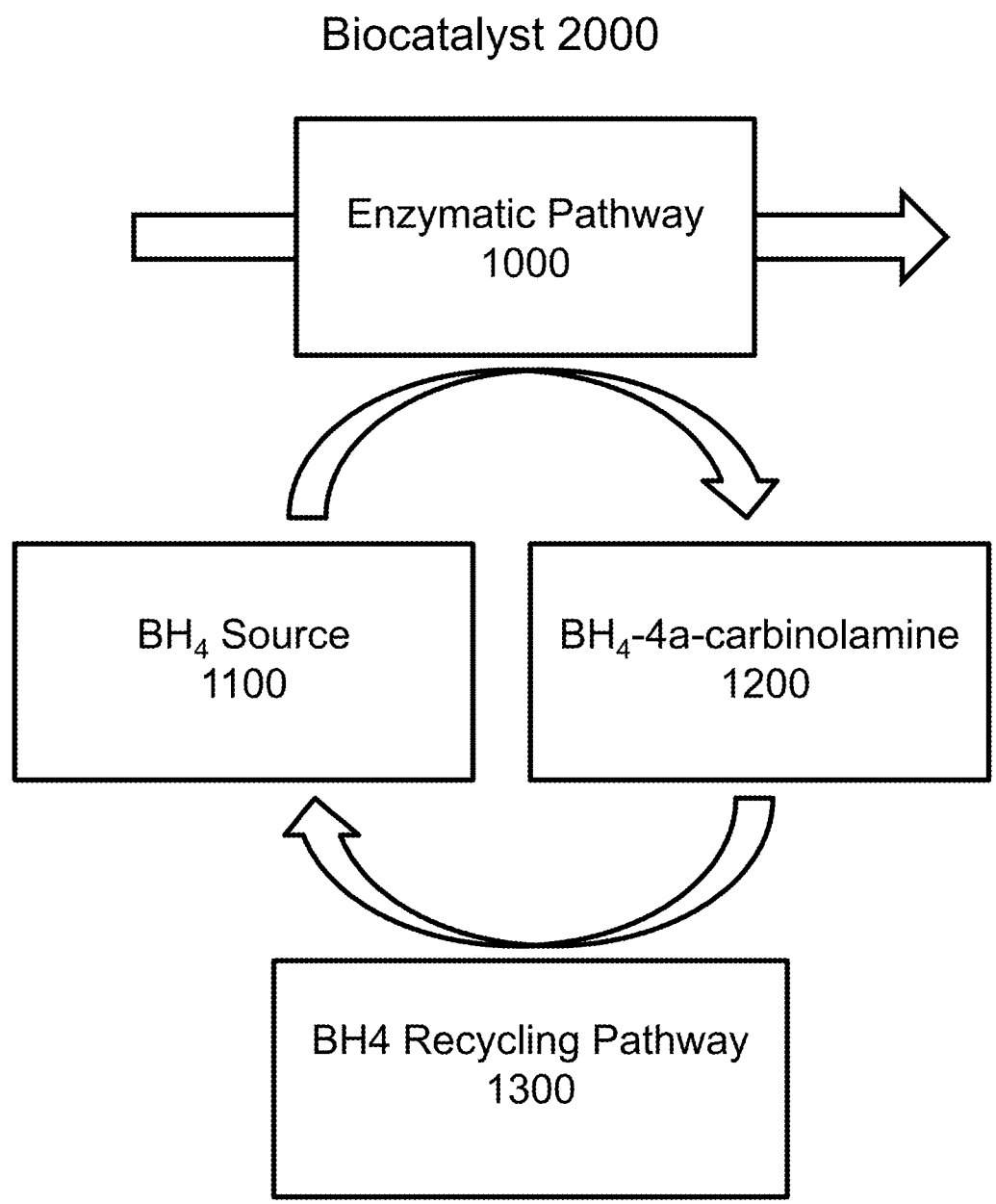
FIG. 2 shows a representative diagram of some embodiments of a biocatalyst 2000 containing an enzymatic pathway 1000 coupled to a BH4 source 1100 and a BH4 recycling pathway 1300.

The biocatalyst 2000 can contain an enzymatic pathway 1000 coupled to a BH4 source 1100 and a BH4 recycling pathway 1300 (FIG. 2). The enzymatic pathway 1000 can utilize BH4 from a BH4 source 1100 as a cofactor. As the enzymatic reaction of the enzymatic pathway 1000 progresses, BH4 used by the enzymatic pathway 1000 can be converted into BH4-4a-carbinolamine 1200. The BH4 recycling pathway 1300 can convert BH4-4a-carbinolamine back into BH4.

Figure 3:
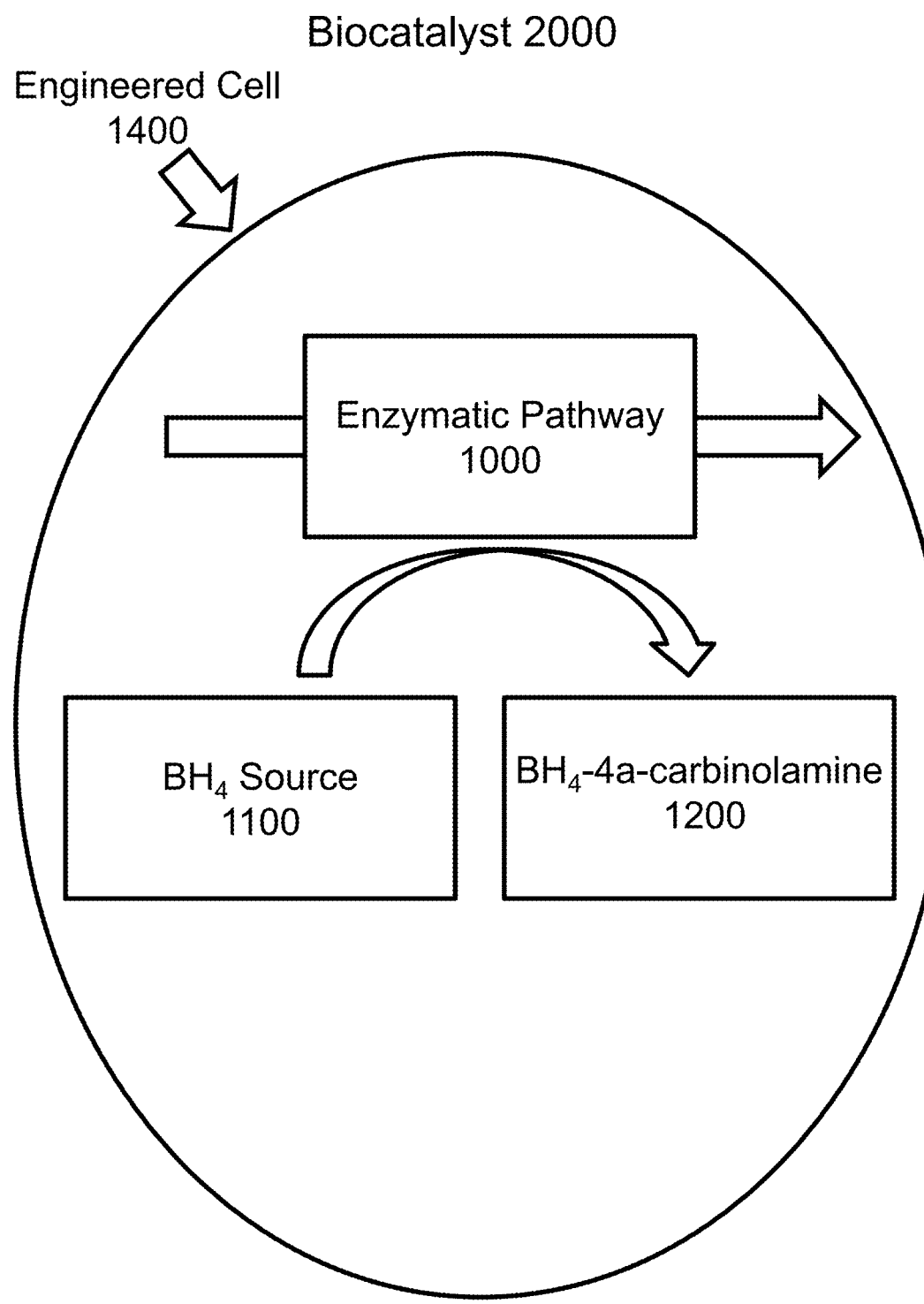
FIG. 3 shows a representative diagram of an embodiment cell 1400, which can contain a biocatalyst 2000. The biocatalyst can contain an enzymatic pathway 1000 biologically coupled to a BH4 source 1100.

The biocatalyst 2000 can be contained in or expressed in a cell 1400, which can contain an enzymatic pathway 1000 coupled to a BH4 source 1100 (FIG. 3). In other words, a cell can be engineered to contain a biocatalyst as previously described. The enzymatic pathway 1000 can utilize BH4 from a BH4 source 1100 as a cofactor. As the enzymatic reaction of the enzymatic pathway 1000 progresses, BH4 used by the enzymatic pathway can be converted into BH4-4a-carbinolamine 1200. The enzymatic pathway 1000 can optionally be omitted from the engineered cell for a biocatalytic engineered cell that only produces BH4. In some embodiments, the enzymatic pathway can be contained in a first cell and the BH4 source 1100 can be contained in a second cell. The first cell and the second cell can be contained in the same environment (e.g. a cell culture system) such that the BH4 produced by the second cell can be utilized by the enzymatic pathway 1000 of the second cell.

In some embodiments, the cell 1400, can contain an enzymatic pathway 1000 coupled to a BH4 source 1100 and an optional BH4 recycling pathway 1300 (FIG. 4). The enzymatic pathway 1000 can utilize BH4 from a BH4 source 1100 as a cofactor. As the enzymatic reaction of the enzymatic pathway 1000 progresses, BH4 can be converted into BH4-4a-carbinolamine 1200. The BH4 recycling pathway 1300 can convert BH4-4a-carbinolamine back into BH4. The enzymatic pathway 1000 can again be omitted if an engineered cell that produces and recycles BH4 only is desired. In some of these embodiments, a cell that only expresses the BH4 source 1100 and a BH4 recycling pathway 1300 can be contained in a population of cells that further contains a cell that contains an enzymatic pathway 1000, such that the BH4 produced by the cell expressing the BH4 source 1100 and recycling pathway 1300 can be utilized by the enzymatic pathway 1000 of the other cell The physically distinct components (e.g. enzymes and biochemical pathways) can be expressed within a whole cell. The whole cell can be a prokaryotic cell or a eukaryotic cell. In some embodiments, the cell is a yeast cell. In other embodiments, the physically distinct components can be expressed in a synthetic in vitro system. The physically distinct components can be considered modular components where each one can be independently manipulated and changed without alteration of the other components. This modular configuration can allow for efficient and rapid tuning and customization of system based on the desired synthetic output of the biocatalyst. The individual modular components are discussed in further detail below.

Tetrahydrobiopterin (BH4) Source

The biocatalyst 2000 described herein can include an enzymatic pathway 1000 that is dependent on and/or biologically coupled to a pterin for catalysis of the enzymatic reaction of the enzymatic pathway 1000. The biocatalyst 2000 can be expressed in a cell 1400 as previously described in relation to e.g. FIGS. 3-4. Microbes, such as yeast, do not endogenously express pterins that can be appropriately coupled to an enzymatic pathway 1000. Therefore, exogenous pterin must be provided to a microbe (or other pterin deficient cell) that expresses a pterin-dependent enzyme or pathway in order for the pterin-dependent enzyme or pathway to properly function. In embodiments, exogenous pterin can be provided directly or a pterin source 1100 can be included in the biocatalyst system for proper functioning.

The biocatalyst 2000 can contain a pterin source. The pterin source can provide tetrahydrobiopterin (herein referred to as BH4 or $BH_4$). The BH4 source 1100 can be a BH4 synthesis pathway. A BH4 source 1100 that can contain a BH4 synthesis pathway can include one or more enzymes that are biologically coupled to each other and/or in biological communication with each other. In some embodiments, the BH4 source can contain one or more of the enzymes GTP cyclohydrase, pyruvoyl tetrahydropterin synthase, and/or sepiapterin reductase. In embodiments, the BH4 source can be a BH4 synthesis pathway that contains enzymes that, in operation, biologically communicate with each other to produce BH4 from a purine, such as guanosine triphosphate (GTP). In embodiments where the BH4 source 1100 is a BH4 synthesis pathway recombinant expressed in a cell, GTP or other suitable purines that fuel the BH4 synthesis pathway can be synthesized by endogenous pathways already present in a cell from a carbohydrate or sugar substrate, such as glucose or galactose.

In some embodiments, the BH4 source can contain a polypeptide with a sequence or a part thereof that is 90% to 100% identical to or corresponds to a sequence that is 90% to 100% identical to SEQ ID NOs.: 1-11. In other embodiments, the BH4 source can contain a polypeptide with a sequence or part thereof that is a homologue, orthologue, xenologue, or paralogue to a sequence or a part thereof that is 90% to 100% identical to or corresponds to a sequence that is 90% to 100% identical to SEQ ID NOs.: 1-11. The sequences can be codon optimized. The sequences can be codon optimized for yeast.

Other pterins and modified pterins may be suitable as a pterin source, such as tetrahydromonopterin (MH$_4$) or other modified pterins. BH4 can be accepted with higher efficiency by amino acid mono-oxygenases from higher eukaryotes than MH4, such as those in the present disclosure. The BH4 synthesis pathway can be configured to catalyze a substrate such as a carbohydrate or a sugar, such as glucose or galactose, to synthesize BH4.

Tetraydrabiopterin (BH4) Recycling Pathway

The biocatalyst can optionally include a pterin recycling pathway 1300. The pterin recycling pathway 1300 can be biologically coupled to the BH4 source 1100. This can provide a constant pterin supply for the enzymatic pathway 1000. A suitable pterin can be BH4 that is provided by a BH4 source 1100. In the presence of a BH4 recycling pathway 1300, BH$_4$-4a-carbinolamine can be converted back to BH$_4$ via the intermediate quinoid dihydrobiopterin through consecutive reactions by pterin-4a-carbinolamine dehydratase (PCD) and dihydropteridine reductase (DHPR). Other suitable pterin recycling components can be substituted depending on the desired pterin utilized. In some embodiments, the BH4 recycling pathway can contain a polypeptide with a sequence or a part thereof that is 90% to 100% identical to or corresponds to a sequence that is 90% to 100% identical to SEQ ID NOs.: 12-13. In other embodiments, the BH4 recycling pathway can contain a polypeptide with a sequence or part thereof that is a homologue, orthologue, xenologue, or paralogue to a sequence or a part thereof that is 90% to 100% identical to or corresponds to a sequence that is 90% to 100% identical to SEQ ID NOs.: 12-13. The sequences can be codon optimized. The sequences can be codon optimized for yeast.

Enzymatic Pathway

The biocatalyst 2000 can have an enzymatic pathway 1000 that can or is configured to utilize BH4 from a BH4 source 1100. The enzymatic pathway 1000 can use MH4 or another modified pterin. The enzymatic pathway 1000 can be a direct and selective enzymatic hydroxylation reaction. The enzymatic pathway 1000 can be a direct and selective enzymatic hydroxylation reaction comprising a natural or modified amino acid mono-oxygenase. The enzymatic pathway 1000 can be comprised of nitric oxide synthase or alkylglycerol monooxygenase. The enzymatic pathway 1000 can be an alkaloid synthesis pathway. An enzymatic pathway 1000 comprising an alkaloid synthesis pathway can be comprised of a pterin-dependent oxidation component that is coupled to a pterin, a decarboxylation component, and/or a condensation component. The enzymatic pathway 1000 can be configured to receive a carbohydrate, glucose, galactose, and/or lignin or a derivative or a metabolite thereof. In some embodiments, the enzymatic pathway can contain a polypeptide having a sequence or a part thereof that is 90% to 100% identical to or corresponds to a sequence that is 90% to 100% identical to SEQ ID NOs.: 14-17. In other embodiments, the enzymatic pathway can contain polypeptide having a sequence or part thereof that is a homologue, orthologue, xenologue, or paralogue to a sequence or a part thereof that is 90% to 100% identical to or corresponds to a sequence that is 90% to 100% identical to SEQ ID NOs.: 14-17. The sequences can be codon optimized. The sequences can be codon optimized for yeast.

Biocatalyst-Expressing Vectors and Cells

Enzymes and other components of the biocatalyst 2000 herein can be present as DNA sequences in an expression vector. The expression vector can be a plasmid. The DNA sequences can be coding sequences and/or codon optimized for suitable expression in a host. The DNA sequences in the vector can be expressed downstream of a promoter. A promoter can be a generic constitutive promoter, generic species-specific promoter, host-specific promoter, or inducible promoter. A promoter can be naturally occurring or artificial, codon optimized, and/or modified. In embodiments, a vector can contain a sequence containing all or part of a sequence having about 90% to 100% identity to any one of SEQ ID NOs: 1-17. The vector can contain all or part of a sequence that is a homologue, orthologue, xenologue, paralogue to any sequence having about 90%-100% identity to any one of SEQ ID NOs: 1-17. The sequences can be codon optimized. The sequences can be codon optimized for yeast.

The BH4 synthesis pathway, BH4 recycling pathway, and enzymatic pathway can be expressed or otherwise contained within a single host cell. The host cell can be eukaryotic or prokaryotic. In some embodiments, the host cell can be a fungal cell or a bacterial cell. In some embodiments the host cell is a yeast cell. A yeast platform for amino acid mono-oxidation can facilitate the synthesis of complex plant alkaloids, as expression of downstream alkaloid pathway enzymes are thought to be mainly transmembrane cytochrome P450s, which are difficult to functionally express in bacteria such as *E. coli* without protein engineering. In addition, *S. cerevisiae*'s robustness, tolerance to industrial conditions, including low pH and high sugar concentrations, and insusceptibility to phage infection can make it a suitable host for chemical production. Yeast species for the host cell can include but are not limited to *S. cerevisiae, Pichia Pastoris, Saccharomyces Pombe*. Suitable strains of *S. cerevisiae* include, but are not limited to the W303 strain (ATCC), PPY810, PPY752, PPY753, PPY754, PPY755, PPY756, PPY757, PPY758, PPY759, PPY760, PPY761, PPY762, PPY764, PPY764, PPY765, PPY766, PPY767, PPY768, PPY797, PPY798, PPY799, PPY800, PPY801, PPY802, PPY803, PPY769, PPY804, PPY805, PPY806, PPY807, PPY808, PPY809, PPY770, PPY771, PPY772, PPY773, PPY774, PPY775, PPY776, PPY77, PPY778, PPY779, PPY780, PPY781, PPY782, PPY783, PPY784, PPY785, and PPY786.

The biocatalyst system or any component thereof can be introduced into the host cell via a single or multiple plasmid system (transient expression) or integrated into the genome (for stable expression). The biocatalyst system can be introduced vie electroporation, nucleofection, transfection, transformation, or any otherwise suitable technique for introducing exogenous genetic sequences into a prokaryotic or eukaryotic cell. There can be single and/or multiple copies of each system component present. The biocatalyst can be stably or transiently expressed within the host cell. Stable or transient expression of the biocatalyst system within the host cell can be accomplished under generic constitutive promoters, generic species-specific promoters, host-specific promoters, or inducible promoters. Promoters can be naturally occurring or artificial, codon optimized, and/or modified. Components of the biocatalysts and systems thereof described herein can also be introduced into a cell by a virus. The virus can be an adeno-associated virus, a lentivirus, a baculovirus, or any other viral host suitable for delivering a genetic sequence into a host.

Systems and Methods of Using the Pterin-Dependent Biocatalysts

Also described herein are systems and methods of using the biocatalyst 2000. As described above the modular components of the biocatalyst 2000 can be expressed within a host cell (also referred to herein as a cell or an engineered cell). The biocatalyst (either in a cell-free system) or as contained within an engineered cell can be used in a method to produce amino acids, non-natural amino acids, hydroxylated aromatics, and other compounds of interest. The method can include providing a biocatalyst and/or cell containing a biocatalyst as described elsewhere herein and a substrate. The method can further contain the step of incubating the biocatalysts and/or the cell containing a biocatalyst 2000 as described herein in with the substrate for a length of time. The length of time can range from about 1 hour to about 1, 2, 3, 4 or more weeks. Suitable substrates include, but are not limited to carbohydrates and sugars. In some embodiments, the substrate is glucose and/or galactose. Suitable cell culture techniques will be appreciated by those of skill in the art.

After incubation a suitable assay or other suitable measurement technique can be performed to confirm and/or measure the product or amount of product produced by the biocatalyst. One of skill in the art will appreciate that the particular assays or measurement technique used will depend on the type of substrate and the enzymatic components of the enzymatic pathway. Suitable assays and measurement techniques include, but are not limited to, mass spectrometry, nuclear magnetic resonance, UV-Vis evaluation, flow cytometry, FACS, luciferase assays (single and dual), β-galactosidase assays, microtiter plate reader, and CAT assays, antibiotic selection, auxotrophic forward and counter selection. Other assays and techniques will be readily appreciated by those of ordinary skill in the art.

The biocatalyst can produce BH4 from a carbohydrate substrate. The biocatalyst can directly and/or selectively hydroxylate aromatic rings. The biocatalyst can produce alkaloids. In some embodiments, the biocatalyst can produce non-natural amino acids. In embodiments, the biocatalyst can convert tyrosine to L-DOPA, which is an example of an unnatural amino acid. It will be appreciated that unnatural amino acids can be incorporated into polypeptide using appropriate tRNA/aminoacyl-tRNA synthase pairs. In other embodiments, the biocatalyst contained in an engineered cell can produce L-dopa, dopamine, 5-hydroxytryptophan and serotonin from a carbohydrate substrate, this carbohydrate can be glucose or galactose.

Figure 5C:
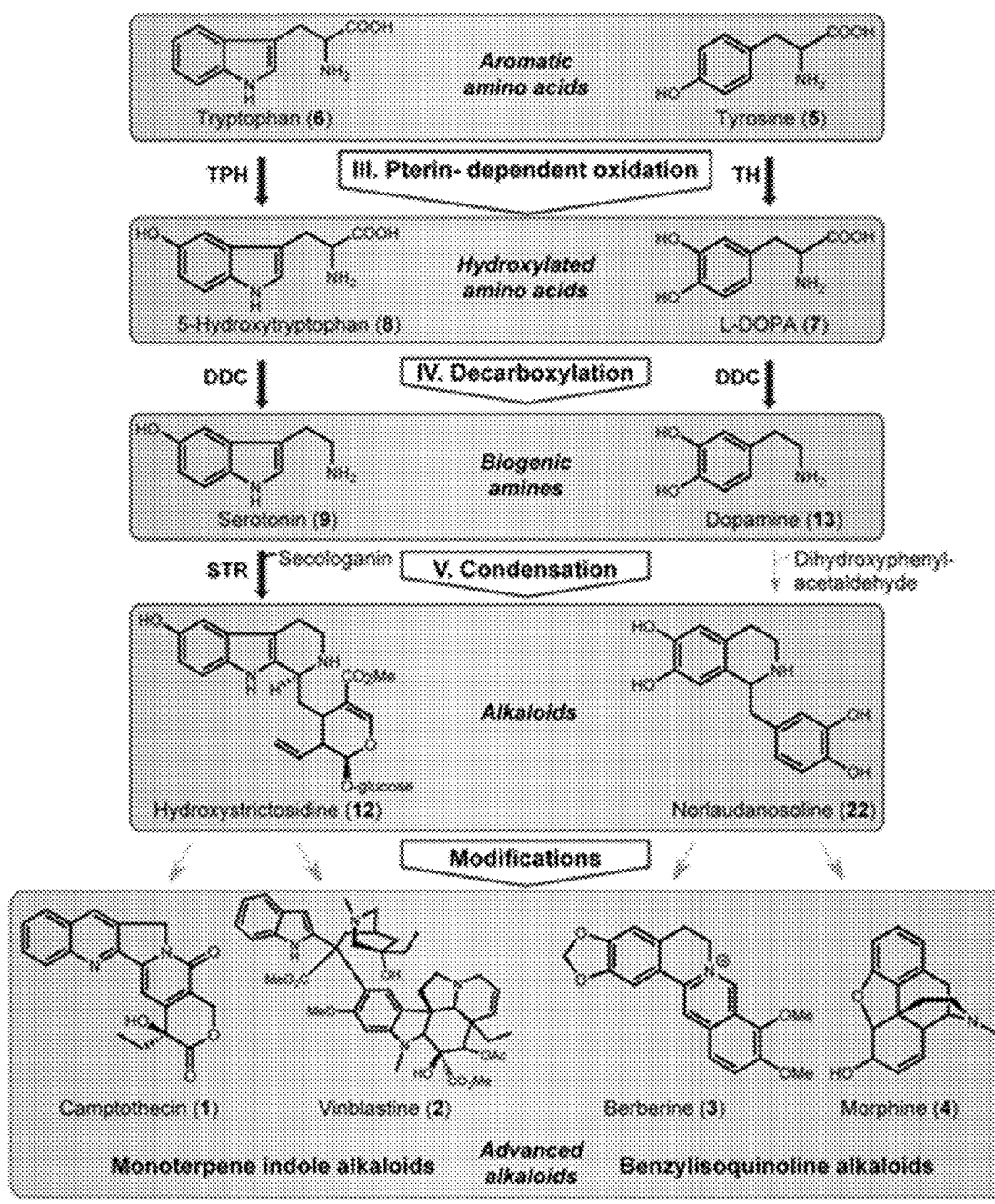
Figure 6:
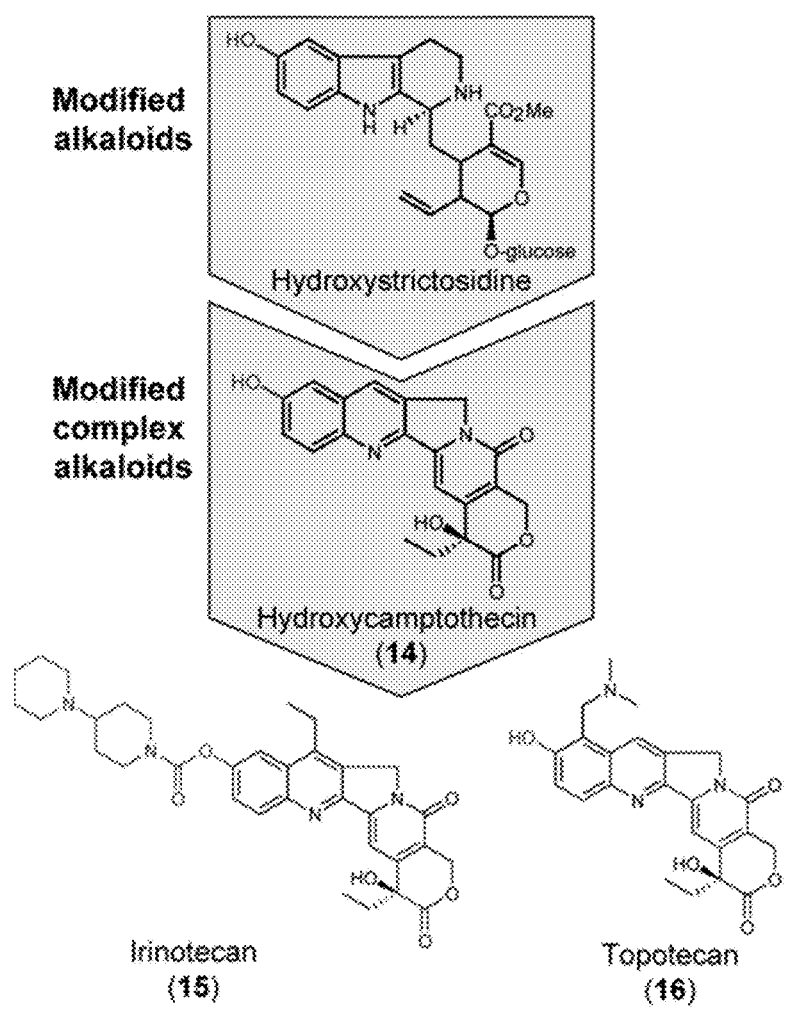
FIG. 6 shows a scheme demonstrating embodiments of a modified MIAs for the semi-synthesis of pharmaceuticals.

Additional embodiments of the biocatalyst can modify monoterpene indole alkaloids or modified monoterpene indole alkaloids produced by condensation to produce more advanced complex monoterpene indole alkaloid products or benzlisoquinoline alkaloids (FIG. 5). Modifications of hydroxystrictosidine and norlaudanosoline can produce valuable pharmaceutical compounds such as camptothecin, vinblastine, berberine, and morphine. In some embodiments, the biocatalyst can be used to produce pharmaceutical compounds. FIG. 6 shows one embodiment of pharmaceutical semisynthesis wherein hydroxycamptothecin 31 can be converted from hydroxystrictosidine 30 via the MIA biosynthetic pathway. Hydroxycamptothecin can then enable rapid access to the anticancer drugs topotecan and irinotecan. As such, in embodiments, the biocatalyst can be used to produce chemotherapeutics, including but not limited to topotecan and irinotecan.

Kits

Also provided herein are kits containing a biocatalyst, a cell or population thereof containing a biocatalyst as described herein, and/or one or more vectors configured to express one or more components of the biocatalyst described herein. The kit can contain one or more substrates suitable for use with the biocatalyst described herein. The kit can further contain additional reagents, diluents, cell culture media, cell culture plates or other container, syringes, and other components (cells, vectors, transfection regents, etc.) that can be used with the biocatalyst, a cell or population thereof containing a biocatalyst as described herein, and/or one or more vectors.

EXAMPLES

Now having described the embodiments of the present disclosure, in general, the following examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Alkaloid Synthesis

Alkaloids are the largest group of nitrogen-containing secondary metabolites, with more than 20,000 structures[1], are present in roughly 20% of plant species[2], and are important because of their medicinal use[3]. Of particular importance are monoterpene indole alkaloids (MIAs) (FIG. 5), which include anticancer agents such as camptothecin (1) and vinblastine (2), antimalarial agents such as quinine, and antiarrhythmic agents such as ajmalicine. Another important alkaloid family is benzylisoquinoline alkaloids (BIAs), which include the antibiotic berberine (3) and the analgesic morphine (4)[4]. Due to their chemical complexity, alkaloids often require multi-step chemical syntheses, which, coupled with the necessity of enantiopure material, make them a challenging synthetic target[5-8]. Therefore, medically important alkaloids, or advanced intermediates thereof, are frequently isolated directly from the native plants[5,7,9]. Although effective, isolation of alkaloids from plants is often limited by their low accumulation in plant tissue and their difficult separation from other natural products, thus resulting in the high cost of alkaloid-derived pharmaceuticals, especially those based on MIAs[5-7]. Via plant breeding and, more recently, plant metabolic engineering, the production of BIAs and MIAs in planta has been increased[10-13]. Further, plants have been engineered to produce halogenated MIAs, with potentially higher bioactivity, which can serve as late intermediates in the semi-synthesis of other alkaloids[14-16]. Nevertheless, limited understanding of plant secondary metabolite regulation and slow plant growth rate cloud the future of engineering plants to overproduce alkaloids[2,5,7]. These limitations result in the underrepresentation of alkaloid-derived compounds in pharmaceutical drug screenings[17]. The synthesis of plant alkaloids in microbes would enable the rapid and scalable production of known alkaloids and open the door to the biosynthesis of novel alkaloids using engineered enzymes or combinatorial enzyme assembly. Plant alkaloid production in microbes has the advantages of short doubling time, rapid extraction of the alkaloid from the culture medium, easier isolation of the desired alkaloid due to the absence of similar natural products, and a lack of endogenous pathway regulation, which allows for deregulation of alkaloid biosynthesis.

Many alkaloids are obtained via the hydroxylation and decarboxylation of amino acids[18]. Specifically, BIAs are derived from tyrosine (5) and MIAs are derived from tryptophan (6). In the last ten years, full elucidation of many BIA biosynthetic pathways in conjunction with advances in synthetic biology, have allowed the reconstruction of BIA pathways in both $Escherichia\ coli$ and $Saccharomyces\ cerevisiae$[19-25]. Although MIA biosynthetic pathways have been extensively engineered in planta, the engineering of MIA alkaloids in microbes has been limited. A major problem in engineering microbes for the synthesis of plant alkaloid is the amino acid hydroxylation step. Tyrosinase (also known as tyrosine hydroxylase), the most common enzyme used to hydroxylate tyrosine, not only oxidizes tyrosine into L-3,4-dihydroxyphenylalanine (L-DOPA, 7), but its o-diphenolase activity also results in further oxidation of L-DOPA to L-dopaquinone, a melanin precursor[26-28], thus reducing the availability of L-DOPA for alkaloid production. Nevertheless, tyrosinase has been used to produce the BIA reticuline from glycerol[21 and 25]. Recently, a P450 enzyme from beet was engineered for reduced o-diphenolase activity to increase the specificity of tyrosine hydroxylation to L-DOPA[29]. There is no equivalent to tyrosinase for tryptophan hydroxylation. To circumvent this problem, microbial production of 5-hydroxytryptophan (8) can be achieved by indole hydroxylation followed by coupling to serine[30] or using an engineered phenylalanine hydroxylase with changed substrate specificity[31]. Hydroxytrytophan has not been converted to serotonin (9) or to MIAs microbially from glucose. Specific mono-oxygenases for tyrosine and tryptophan exist in higher eukaryotes; however, they require the pterin co-factor tetrahydrobiopterin ($BH_4$, 10), which is not present in $E.\ coli$ or $S.\ cerevisiae$.

A pterin-dependent oxidation strategy to specifically mono-oxidize of tyrosine or tryptophan can provide an alternative biosynthetic route for MIA and BIA biosynthesis (FIG. 5). The difficulty in this strategy is that neither $E.\ coli$ nor $S.\ cerevisiae$ endogenously produce $BH_4$, which is necessary for the activity of mono-oxygenases found in higher eukaroytes[32,33]. Although $BH_4$ production has been previously accomplished in $E.\ coli$[34], it was not coupled to amino acid mono-oxidation. The endogenous $E.\ coli$ $BH_4$ analog, tetrahydromonapterin ($MH_4$), can be used as a co-factor for $BH_4$-dependent mono-oxygenases in the production of hydroxytyrosol[35] and 5-hydroxytryptophan[31]. However, $MH_4$ has a different composition and stereochemistry when compared to $BH_4$ (FIG. 12). To establish a microbial platform for the synthesis of plant alkaloids via the pterin-dependent mono-oxidation strategy, $S.\ cerevisiae$ can be engineered for $BH_4$ production. A yeast platform for amino acid mono-oxidation can further facilitate the synthesis of complex plant alkaloids.

A pterin-dependent mono-oxidation strategy for the microbial synthesis of the biogenic amines dopamine and serotonin is described herein. Serontonin synthesis can further be leveraged to produce a modified MIA. An engineered $BH_4$-producing yeast can mono-oxidize tryptophan to 5-hydroxytryptophan, which, after decarboxylation to serotonin, can be condensed with the monoterpene secologanin (11) to produce the modified MIA hydroxystrictosidine (12). $BH_4$ biosynthetic enzymes can be combinatorially screened to produce different levels of BH4. A $BH_4$ recycling pathway can optionally be present to guarantee supply of $BH_4$ to the amino acid mono-oxygenases. Pterin-dependent oxidation of tryptophan is shown herein, followed by decarboxylation results in the biogenic amine serotonin, a key MIA intermediate. The MIA biosynthetic pathway can further be introduced to ultimately produce hydroxystrictosidine from glucose and secologanin. The generality of the pterin-dependent mono-oxidation strategy for the microbial synthesis of alkaloids is shown herein by using the example of a tyrosine mono-oxygenase to convert tyrosine into L-DOPA, which can subsequently decarboxylated to dopamine (13), a key BIA intermediate. The microbial strains presented herein can be used for the scalable production of MIAs, as well as the production of modified MIAs to serve as late intermediates in the semisynthesis of known and novel therapeutics (FIG. 34). Further, the microbial strains in this work can be used as plant pathway discovery tools to elucidate known MIA biosynthetic pathways or to identify pathways leading to novel MIAs.

Target choice: hydroxystrictosidine. While the natural branch point in MIA biosynthesis is strictosidine[44], the biosynthesis of 10-hydroxystrictosidine can be pursued instead, a minor MIA produced by $Camptotheca\ acuminata$[45], the major producer of the anticancer agent camptothecin. The biosynthesis of 10' functionalized strictosidine can provide a chemical handle for the rapid derivatization of strictosidine-derived MIAs. 10-hydroxystrictosidine can be synthesized via the condensation of 5-hydroxytryptamine (serotonin) and secologanin, rather than tryptamine and secologanin as in the case of strictosidine. Modifications at the 5' position of tryptophan have been shown to be processed by MIA enzymes in $Catheranthus\ roseus$ to produce 10' modified ajmalicine, serpentine, and tabersonine[46]. In this spirit, 10-hydroxystrictosidine can enable the biosynthesis of modified MIAs, such as 10-hydroxycamptothecin (14), which has higher anticancer activity than camptothecin[18] (FIG. 6). Modified MIAs such as 10-hydroxycamptothecin can serve as better semi-synthesis intermediates than camptothecin for the chemical synthesis of more water soluble derivatives[18], such as the colon anticancer drug irinotecan (15) and the ovarian and lung cancer drug topotecan (16). More generally, modified MIAs can serve as synthons for the semisynthesis of novel complex alkaloids with potential therapeutic activities.

Microbial synthesis of tetrahydrobiopterin in $S.\ cerevisiae$. $S.\ cerevisiae$ does not produce $BH_4$, but guanosine triphosphate (GTP, 17) can be re-routed to produce $BH_4$ through the intermediates dihydroneopterin triphosphate (18) and pyruvoyl tetrahydropterin (19) using three enzymes: GTP cyclohydrolase I (GTPCH), pyruvoyl tetrahydropterin synthase (PTPS), and sepiapterin reductase (SR) (FIG. 7A). Given that $BH_4$ oxidizes to dihydrobiopterin and, subsequently, to biopterin in water[47], the presence of biopterin in the medium can be used to monitor BH4 in cells. GTPCH is the first committed step in $BH_4$ biosynthesis[48]. $S.\ cerevisiae$ has an endogenous GTPCH as part of the folate biosynthetic pathway and thus requires only expression of heterologous PTPS and SR to produce $BH_4$. $Mortierella\ alpina$ is the only fungus shown to carry the full $BH_4$ biosynthetic pathway from GTP[49], and, given that *S. cerevisiae* is also a fungus, *M. alpina* enzymes can be efficiently expressed in this organism. Overexpression of *M. alpina* PTPS and SR in *S. cerevisiae* produced 0.74 mg/L of $BH_4$, measured as biopterin (FIG. 7B, FIGS. 13A-13B). $BH_4$ can be exogenously fed to yeast cells expressing only a pterin-dependent tyrosine mono-oxygenase to convert tyrosine into L-DOPA. No L-DOPA was seen when feeding 0-50 mg/L of $BH_4$, suggesting that $BH_4$ oxidizes to dihydrobiopterin or biopterin before reaching the tyrosine mono-oxygenase. $BH_4$ can be synthesized intracellularly rather than exogenously fed to determine whether 0.74 mg/L $BH_4$ limits alkaloid biosynthesis.

Four GTPCHs, four PTPSs, and three SRs can be combinatorially expressed in *S. cerevisiae* to identify yeast strains that produce different amounts of BH4. Among GTPCHs, enzymes from *E. coli, M. alpina, Homo sapiens*, and *S. cerevisiae* can be expressed. *E. coli* GTPCH has a low $K_M$ (0.02[50]-100[51] μM) and has been previously expressed in *S. cerevisiae*[52]. *H. sapiens* GTPCH has a pI of 5.6[53], which could aid in its solubility, and it has also been expressed in *S. cerevisiae*[52]. Among PTPSs, the enzymes from *M. alpina, Salmo salar*, the halophile *Salinibacter ruber*, and the bacteria *Phycisphaera mikurensis* can be screened. *S. salar* PTPS has a specific activity that is fifty times higher, and a $K_M$ that is five times lower, than that of the canonical human PTPS[54]. The putative PTPS from *S. ruber* may be suitable because a structural homology model alignment with *S. salar* PTPS revealed that these enzymes have an almost identical active site, except that *S. ruber* PTPS has a catalytic aspartate rather than a cysteine residue[55] (FIG. 14). The aspartate's carboxylate can function as a better acid-base catalyst compared to cysteine's thiol group. The predicted PTPS from *P. mikurensis* can be suitable because its active site is almost identical to the well-studied *Rattus rattus* PTP[56]; however, the *P. mikurensis* PTPS N-terminus has an additional ~100 amino acids. A bioinformatics search revealed that *S. cerevisiae* lacked any PTPS homolog. Among SRs, the SR from *M. alpine*, a predicted SR from the diatom *Thalassiosira pseudonana*, which, based on structural homology models is hypothesized to be NADH- rather than NADPH-dependent (FIG. 15), and a putative SR from *S. cerevisiae* found using bioinformatics can be screened.

Optimization of tetrahydrobiopterin biosynthesis. Increasing the flux through the purine pathway can increase GTP levels and, in turn, $BH_4$ production. The parent yeast strain, W303, has a non-functional phosphoribosylaminoimidazole carboxylase (ade2) gene located upstream of GTP in the purine biosynthetic pathway. A functional Ade2 yeast strain can be generated and introduced the $BH_4$ synthesis pathway. To identify bottlenecks within the $BH_4$ pathway, the expression of each gene in the combinatorially optimized $BH_4$ synthesis pathway can be monitored by expressing each gene from a single- or multi-copy plasmid using galactose-inducible promoters. GTPCH, PTPS and SR mRNA levels can be measured when expressed from single- or multi-copy plasmids (FIG. 16) to determine a suitable expression level. To produce $BH_4$ from glucose and to reduce plasmid burden[57,58], an enzyme combination can be expressed from a multicopy plasmid using constitutive promoters.

Figure 8B:
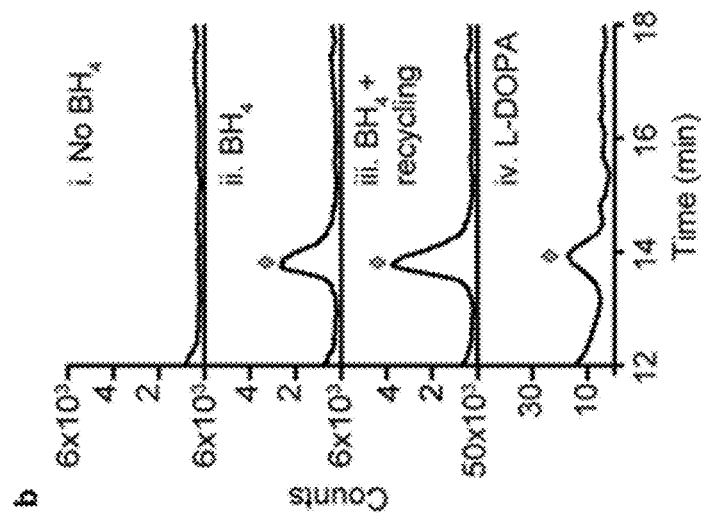
FIGS. 8A-8D demonstrate embodiments of a synthesis scheme and data demonstrating microbial synthesis of L-DOPA via pterin-dependent tyrosine hydroxylation. (a) Schematic representation of the $BH_4$ recycling pathway. (b) Representative LC traces for various production strains (extracted ion chromatograms for L-DOPA=m/z 198). Traces represent strains expressing: i) only tyrosine hydroxylase (TH), ii) TH and the $BH_4$ synthesis pathway, and iii) TH, the $BH_4$ synthesis pathway, and the $BH_4$ recycling pathway. Trace iv is commercial L-DOPA standard. Full windows of the spectra can be found in FIG. 21a. (c) Production levels of L-DOPA from galactose in the presence (+) or absence (−) of the $BH_4$ synthesis pathway and/or $BH_4$ recycling pathway. (d) Production levels of biopterin from galactose in the presence (+) or absence (−) of the $BH_4$ recycling pathway. All experiments were run in triplicate and shown are the mean and standard deviation. Strains carried four multicopy plasmids in which each gene was expressed from galactose inducible promoters ($P_{GAL1}$ or $P_{GAL10}$). PCD: pterin-4a-carbinolamine dehydratase; DHPR: dihydropteridine reductase.
Figure 8A:
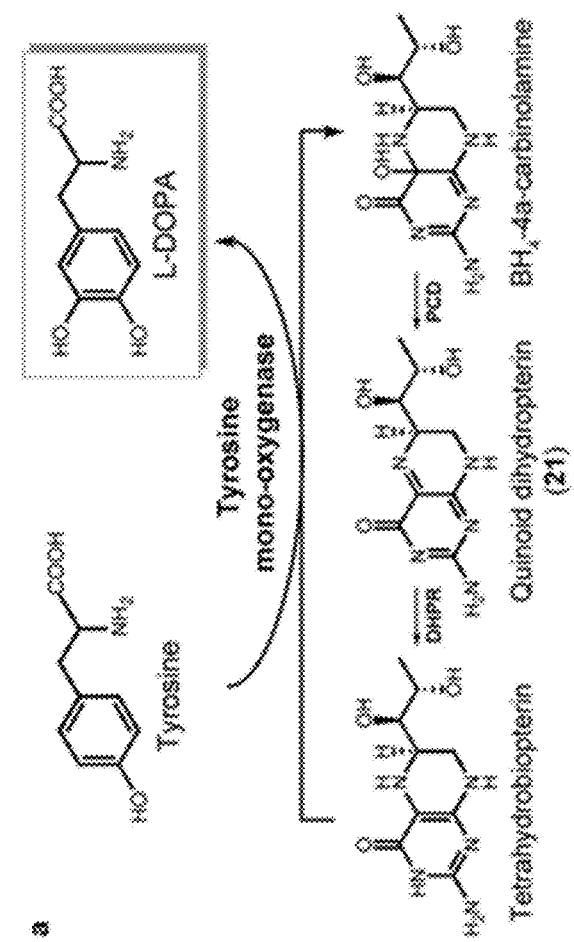
Figure 8D:
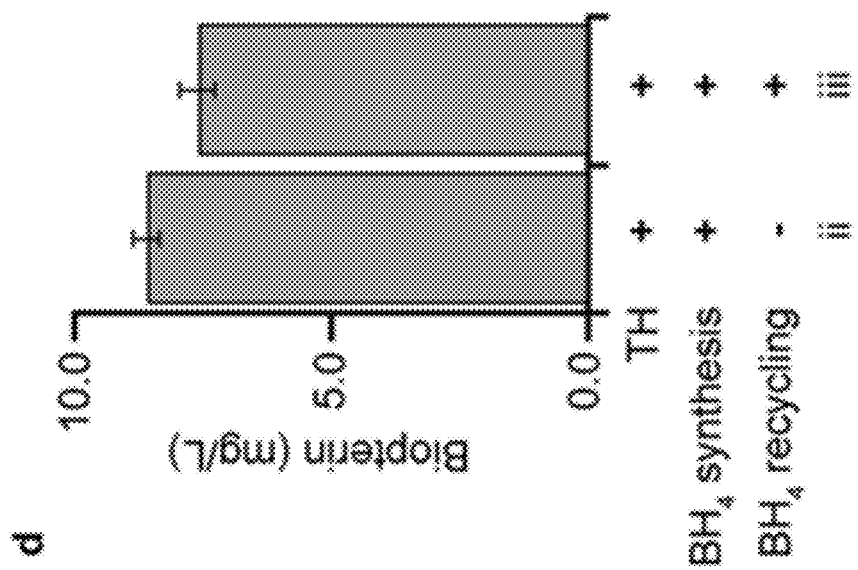
Figure 8C:
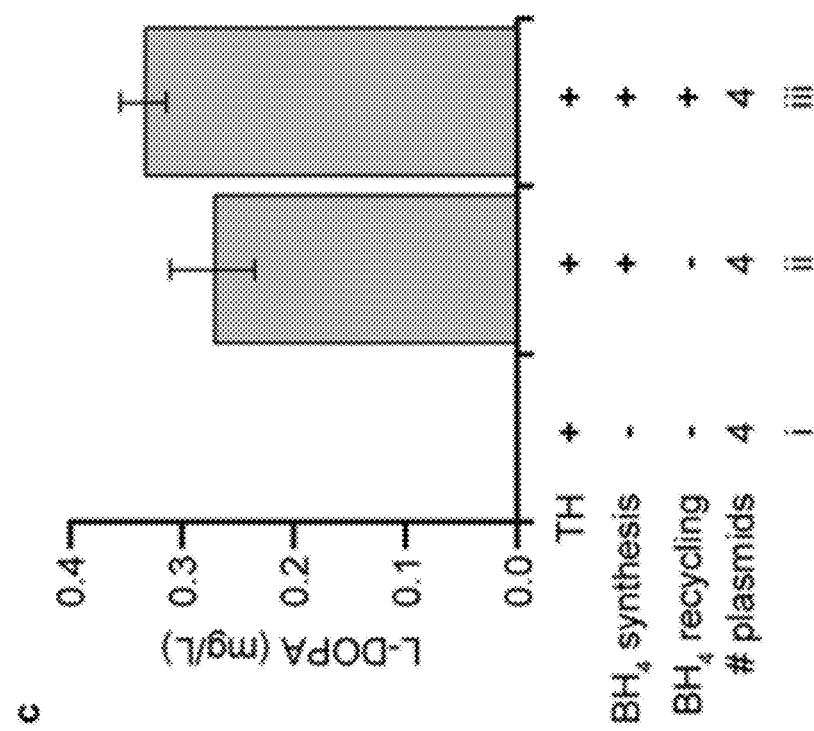
Figure 9G:
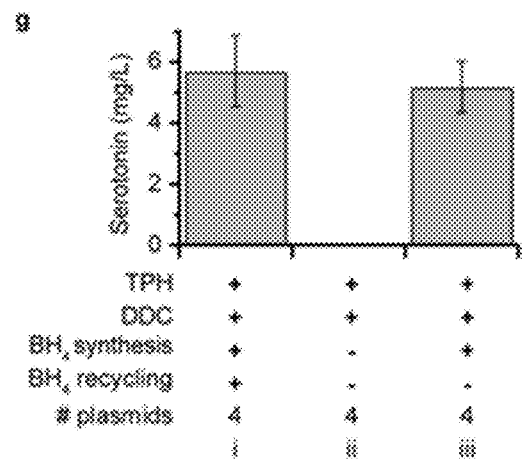
Figure 9H:
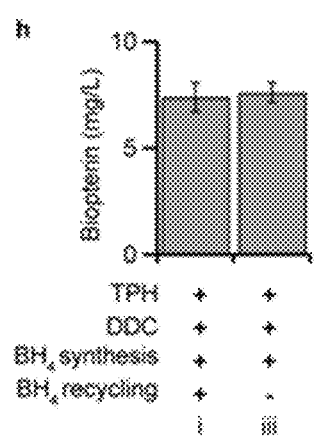

Tetrahydrobiopterin recycling for pterin-dependent amino acid mono-oxidation. Upon amino acid mono-oxidation, $BH_4$ can be converted to $BH_4$-4a-carbinolamine (20). Previous work in *E. coli* has shown the $BH_4$ recycling pathway to be critical to ensure continuous supply of the $BH_4$ analog $MH_4$ in pterin-dependent amino acid mono-oxidation[31,35]. To provide a continuous supply of $BH_4$ to the amino acid mono-oxygenases, a $BH_4$ recycling pathway in *S. cerevisiae* can optionally be included. In the recycling pathway, $BH_4$-4a-carbinolamine is converted back to $BH_4$ via the intermediate quinoid dihydrobiopterin (21) through consecutive reactions by pterin-4a-carbinolamine dehydratase (PCD) and dihydropteridine reductase (DHPR) (FIG. 8A). The effect of the *H. sapiens* $BH_4$ recycling pathway on the pterin-dependent mono-oxidation of tyrosine to L-DOPA can be measured, using the codon optimized *Mus musculus* tyrosine hydroxylase, in 1) the absence of the $BH_4$ biosynthetic and recycling pathways, 2) the presence of only the $BH_4$ biosynthetic pathway, and 3) the presence of both the $BH_4$ biosynthetic and recycling pathways (FIGS. 8B-8C, FIG. 17A). The media can be optionally supplemented with tyrosine to increase L-DOPA production. High-level $BH_4$ synthesis can eliminate the necessity of the $BH_4$ recycling pathway at the current rate of tyrosine mono-oxidation. The media can be supplemented with tyrosine to improve tyrosine biosynthesis.

Microbial synthesis of biogenic amines via pterin-dependent mono-oxidation. Biogenic amines can be the immediate precursors to both MIAs and BIA[5]. To microbially synthesize the BIA biogenic amine precursor dopamine from galactose, a strain carrying the $BH_4$ biosynthetic and recycling pathways, tyrosine mono-oxygenase, and the codon optimized *Sus scrofa* aromatic L-amino-acid decarboxylase (DDC) can be engineered (FIGS. 9A-9D). To microbially synthesize the MIA biogenic amine serotonin from galactose, a yeast strain carrying the $BH_4$ biosynthetic and recycling pathways, a truncated codon optimized *H. sapiens* tryptophan hydroxylas[59], and aromatic-l-amino acid decarboxylase (also known herein as DDC) (FIGS. 9E-9H) can be engineered. The $BH_4$ recycling pathway may not affect biogenic amine production. The media can be optionally supplemented with tryptophan to increase serotonin production.

Figure 10A:
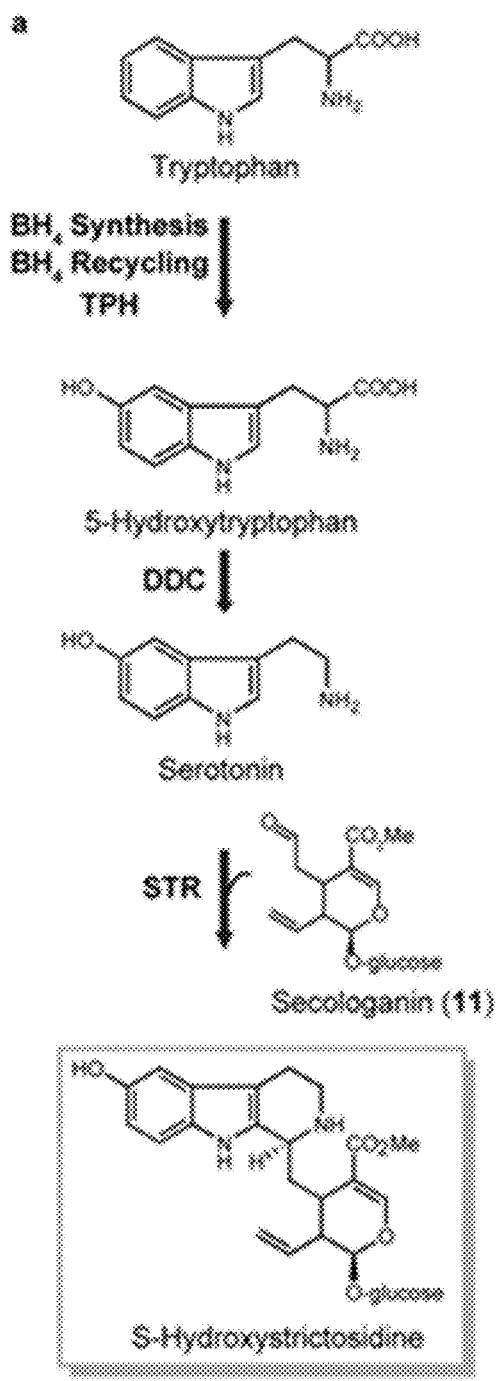
FIGS. 10A-10E show embodiments of a synthesis scheme and data demonstrating microbial synthesis of the modified MIA 10-hydroxystrictosidine. (a) Schematic of hydroxystrictosidine biosynthesis. (b) Representative LC trace (Multiple Reaction Monitoring hydroxystrictosidine 547.60→530.00 transition) for the yeast strain (PPY650) carrying tryptophan hydroxylase, aromatic-L-amino-acid decarboxylase, strictosidine synthase, and the $BH_4$ biosynthesis and recycling pathways in the presence or absence of 0.4 mM secologanin. S=(S)-Hydroxystrictosidine; R=(R)-Hydroxystrictosidine. Full window of the spectra can be found in FIG. 21. (c) Tandem mass spectrum of microbially-produced 5-hydroxystrictosidine. (d) High-resolution mass spectrum of microbially-produced 5-hydroxystrictosidine. (e) (S) and (R)-Hydroxystrictosidine production in *S. cerevisiae*. DDC: aromatic-L-amino-acid decarboxylase; TPH: tryptophan hydroxylase; STR: strictosidine synthase.
Figure 10B:
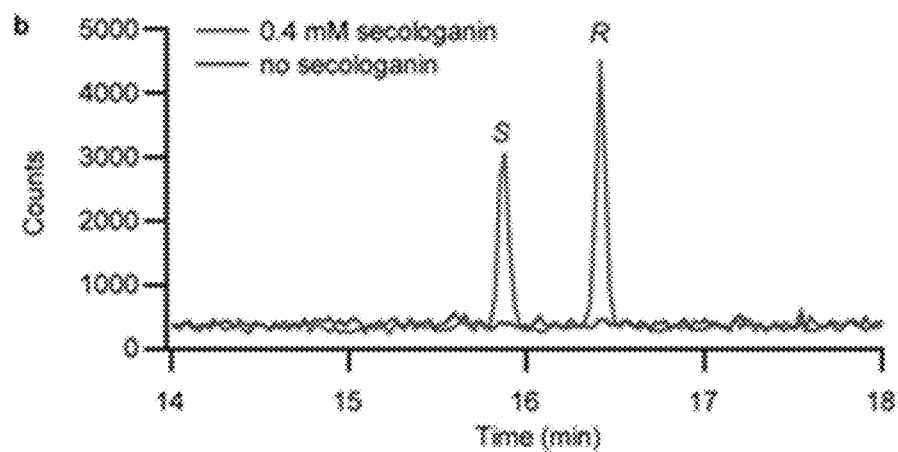
Figure 10C:
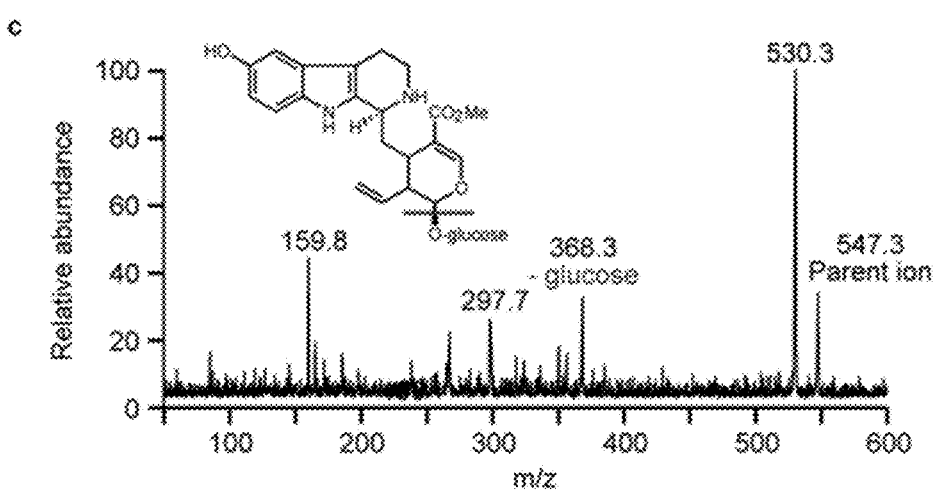
Figure 10D:
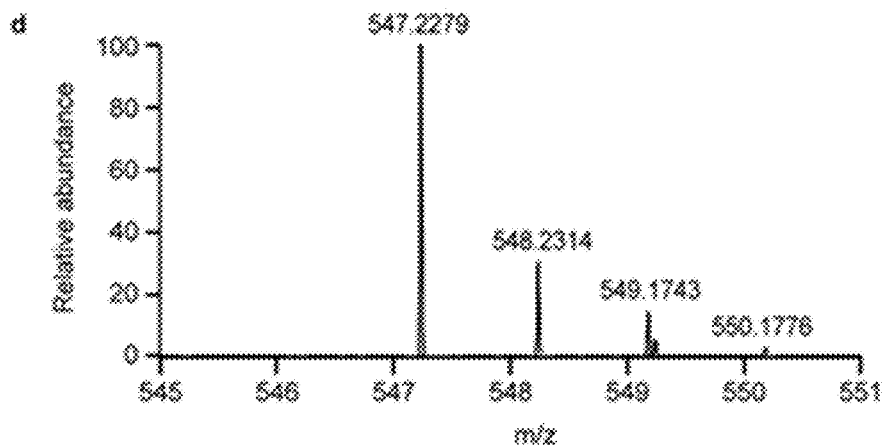
Figure 10E:
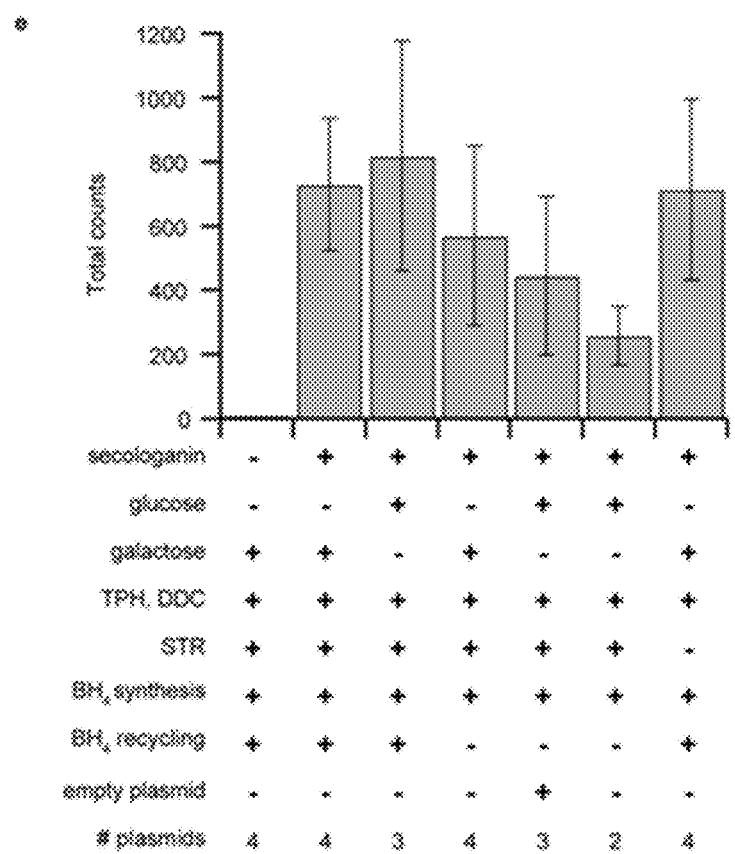

Microbial synthesis of the modified MIA hydroxystrictosidine. Although several microbial strains have been engineered for the production of BIAs[19-25], engineering of MIA microbial platforms has lagged behind[60]. Further, to our knowledge no modified alkaloid has been produced microbially to date. Microbial synthesis of modified alkaloids can generate more amenable intermediates for chemical derivatization to obtain final therapeutics. The pterin-dependent biogenic amine-producing strain can be used for the production of the modified MIA hydroxystrictosidine. To microbially synthesize hydroxystrictosidine from galactose and secologanin, the serotonin-producing strain, carrying the $BH_4$ recycling pathway and expressing the *Ophiorrhiza pumila* strictosidine synthase[61] with the vacuolar tag removed so as to avoid enzyme secretion[62] (FIG. 10A) can be utilized. The strain produced both R- and S-hydroxystrictosidine. (FIG. 10B, FIG. 20). Given that hydroxystrictosidine is not commercially available, the compounds using tandem mass spectrometry and high resolution mass spectrometry (FIGS. 10C-10D, FIG. 21) can be characterized. To improve upon the inducible four-plasmid system, a three-plasmid system using multicopy plasmids with the enzymes under control of constitutive promoters can be used instead of an inducible four plasmid system. The $BH_4$ recycling pathway can be optionally expressed in both the four- and three-plasmid systems. A two-plasmid system without the $BH_4$ recycling pathway can be utilized. The hydroxystrictosidine-producing yeast strains can result in a mixture of R- and S-hydroxystrictosidine isomers. Removing strictosidine synthase from the hydroxystrictosidine-producing strain resulted in similar R- and S-hydroxystrictosidine levels (FIG. 22). This indicated that, at the low pH of the yeast medium (pH=5-3), secologanin and serotonin can couple chemically rather than enzymatically to produce a mixture of hydroxystrictosidine isomers[63]. Indeed, strictosidine synthase can retain less than one tenth of its activity at pH=4-3[64] and has three orders of magnitude less catalytic activity with serotonin when compared to tryptamine[65]

Figure 23A:
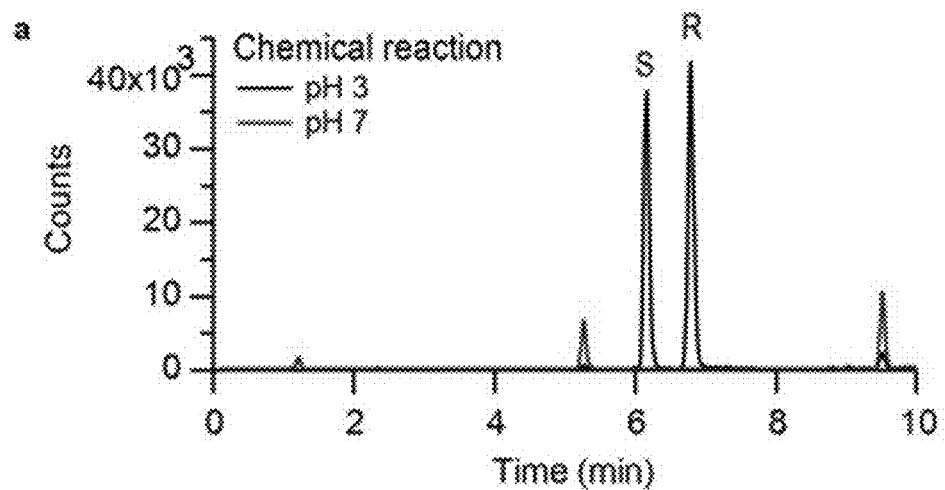
Figure 23B:
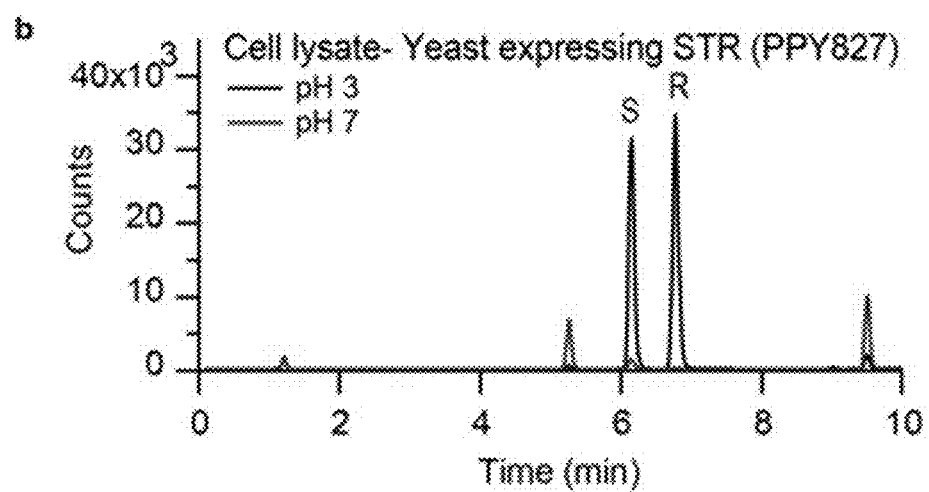
Figure 23C:
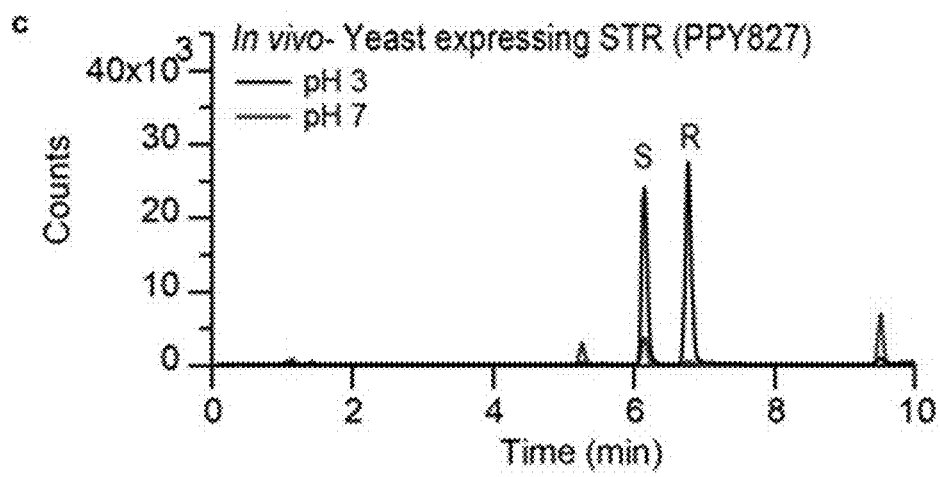
Figure 23D:
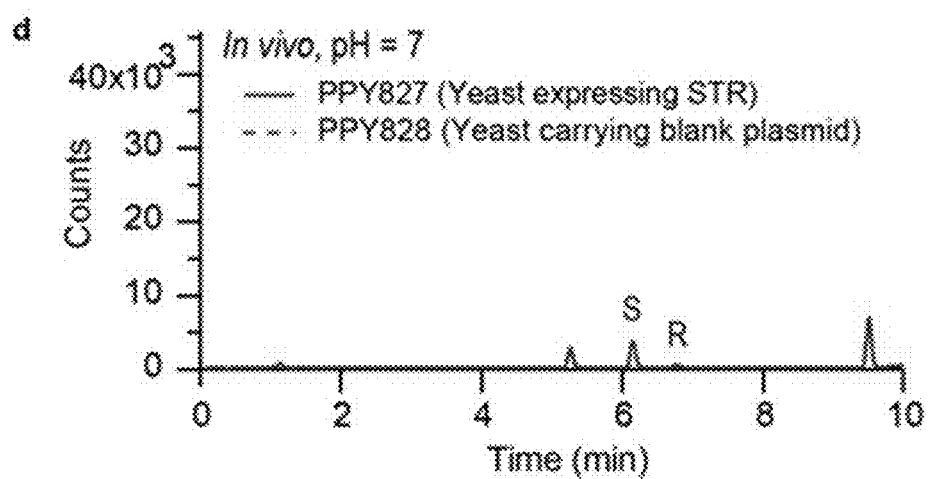

Determining strictosidine synthase functionality. To determine if strictosidine synthase was functionally expressed in the hydroxystrictosidine-producing strain, the level of spontaneous and enzymatic hydroxystrictosidine synthesis can be examined under different conditions. The spontaneous condensation of serotonin and secologanin may not occur at pH=7, but can occur at pH=3, producing both hydroxystrictosidine isomers (FIG. 11A, FIG. 23A). Next, hydroxystrictosidine formation can be examined using the lysate of yeast cells expressing strictosidine synthase. When the lysate was placed at pH=3 and fed serotonin and secologanin, both hydroxystrictosidine isomers can be formed, while the same experiment at pH=7 resulted in only the S-isomer (FIG. 11B, FIG. 23B), demonstrating that strictosidine synthase can be functionally expressed in yeast. Isomer identification can be determined due to the fact that strictosidine synthase is known to form only the S-isomer[61] while the spontaneous chemical condensation produces both R- and S-isomers, with the R-isomer being the major product[63]. Intact yeast cells expressing strictosidine synthase, can be fed exogenous serotonin and secologanin, and cultured the cells for 136 hours using standard (pH=4-2.5, FIG. 24) or buffered (pH=7-5, FIG. 24) synthetic complete media. Yeast cells in the buffered media can result in the synthesis of only 5-hydroxystrictosidine (FIG. 11C, FIG. 23C). Finally, strictosidine synthase can be necessary for S-hydroxystrictosidine production in yeast and that the reaction was not catalyzed by an endogenous yeast enzyme (FIG. 11D, FIG. 23D, FIG. 25). These results demonstrate that strictosidine synthase can be functionally expressed in a hydroxystrictosidine-producing yeast strain, that the enzymatic reaction leading to the S-isomer can take place intracellularly, and that secologanin can cross the yeast cell membrane. In standard yeast synthetic complete media, however, the spontaneous coupling of serotonin and secologanin can be the predominant hydroxystrictosidine forming reaction.

Example 2: Pterin-Dependent Direct and Selective Hydroxylation of Lignin-Derived Aromatic Monomers The utility of plant-derived compounds is not limited to the synthesis of advanced pharmaceuticals. Lignins are a class of complex cross-linked phenol polymers that are important structural components of vascular plants and some algae. Lignocellosic feedstocks, high in lignin content, supply sources of energy, chemicals, and fuel. Most of the products we obtain from feedstocks come from cellulose and hemicellulose, while lignin, which is the second most abundant carbon source on earth, is largely unutilized, with the majority of lignin being burned for energy. Lignin is the only large-volume renewable source that's composed of aromatic units, so there is a great potential for conversion of lignin to products in a variety of industries, including plastics, fuels, and various chemicals.

Current techniques for the breakdown of lignin lead to the production of low-molecular weight monomeric aromatic units such as those shown here (FIG. 26). Many of these are commonly used and, due to their ready availability, they tend to be very cheap, with many being only cents per gram. These monomeric units can then be upgraded, or valorized, to create more costly molecules by various reactions including repolymerization, alkylation, oxidation to quinones, reduction, or oxidation, specifically hydroxylation.

Hydroxylation is a useful tool in chemical synthesis, however it is very challenging to obtain direct and selective hydroxylation onto aromatic rings. Various reactions exist for chemical hydroxylation, however they each have their own drawbacks. These include metal catalysis, which can be unpredictable in the number and selectivity of the hydroxylations, the use of super critical $CO_2$, which hasn't been used on aromatic substrates, and the Heck process, which represents a multi-step hydroxylation process. One solution to these problems is to utilize biology and take advantage of enzymes already found throughout nature.

Enzymatic hydroxylation as described previously and further described herein can also be applied to monomeric aromatic compounds that are the degradation products of lignins. This yields an environmentally-friendly solution to the direct and selective hydroxylation of aromatic rings. Enzymatic hydroxylation is catalyzed by many classes of enzymes, a few of which are described herein. The first class includes dioxygenases, which use molecular oxygen to hydroxylate either the substrate twice, such as the case in indigo production by napthalene dioxygenase, creating a cis-diol, or hydroxylate the substrate and a co-substrate, such as is the case with flavone 6 hydroxylase. The most well-known class of oxygenases are cytochrome P450s, which are typically membrane-bound enzymes which hydroxylate their substrates using a heme-iron and a reductase partner. Non-heme monooxygenases include many subclasses. Flavin mono-oxygenases, which utilize reducing cofactors NADH or NADPH, have been used in the production of muconic acid. A further type of oxygenases are aromatic amino acid mono-oxygenases.

The side chain of tyrosine resembles many of the major products obtained during lignin pyrolysis, having the phenol scaffold (FIG. 26). A whole-cell biocatalysis system where various monomeric aromatics (which can be products of lignin degradation, FIG. 26) are fed to a cell expressing an amino acid mono-oxygenase coupled to a pterin source (exemplified in FIGS. 27A-27B) to obtain selectively hydroxylated products with a single step reaction is described in further detail in an example below. The active site of an amino-acid mono oxygenase can be modified to improve substrate specificity for aromatic monomers or other aromatic compounds. These hydroxylated products could then be further used in industry or in the creation of industrially-used chemicals, used as pharmaceutical precursors, or used as fuel precursors (FIGS. 27A-27B).

Example 3: Biosynthesis of Hydroxylated 2,6-Dimethoxy-4-Methylphenol Via Pterin-Dependent Tyrosine Mono-Oxidation FIG. 29A shows a schematic representation of the mono-oxidation of 2,6-dimethoxy-4-methylphenol. 1: Engineered yeast carrying the BH4 synthesis pathway to provide a BH4 source and tyrosine hydroxylase. FIG. 29B shows representative LC traces for 2,6-dimethoxy-4-methylphenol mono-oxidation. i) Wild type yeast with 2,6-dimethoxy-4-methylphenol. ii) Media with 2,6-dimethoxy-4-methylphenol. iii). Engineered yeast carrying the BH4 synthesis pathway (BH4 pathway), tyrosine hydroxylase and 2,6-dimethoxy- 4-methylphenol result in the biosynthesis of a hydroxylated 2,6-dimethoxy-4-methylphenol (m/z=184) at retention time 8.5 min (black diamond).

REFERENCES FOR EXAMPLES 1, 2, AND 3

1 Schafer, H., and Wink, M. (2009) Medicinally important secondary metabolites in recombinant microorganisms or plants: progress in alkaloid biosynthesis. *Biotechnol. J.* 4, 1684-1703.
2 Minami, H. (2013) Fermentative Production of Plant Benzylisoquinoline Alkaloids in Microbes. *Biosci. Biotech. Bioch.* 77, 1617-1622.
3 Yang, L. Q., and Stockigt, J. (2010) Trends for diverse production strategies of plant medicinal alkaloids. *Nat. Prod. Rep.* 27, 1469-1479.
4 Hagel, J. M., and Facchini, P. J. (2013) Benzylisoquinoline Alkaloid Metabolism: A Century of Discovery and a Brave New World. *Plant Cell Physiol.* 54, 647-672.
5 Leonard, E., Runguphan, W., O'Connor, S., and Prather, K. J. (2009) Opportunities in metabolic engineering to facilitate scalable alkaloid production. *Nat. Chem. Biol.* 5, 292-300.
6 Winter, J. M., and Tang, Y. (2012) Synthetic biological approaches to natural product biosynthesis. *Curr. Opin. Biotechnol.* 23, 736-743.
7 Chemler, J. A., and Koffas, M. A. (2008) Metabolic engineering for plant natural product biosynthesis in microbes. *Curr. Opin. Biotechnol.* 19, 597-605.
8 Kuboyama, T., Yokoshima, S., Tokuyama, H., and Fukuyama, T. (2004) Stereocontrolled total synthesis of (+)-vincristine. *Proc. Natl. Acad. Sci. U.S.A.* 101, 11966-11970.
9 Murata, J., Roepke, J., Gordon, H., and De Luca, V. (2008) The leaf epidermome of *Catharanthus roseus* reveals its biochemical specialization. *Plant Cell* 20, 524-542.
10 Sato, F., Hashimoto, T., Hachiya, A., Tamura, K., Choi, K. B., Morishige, T., Fujimoto, H., and Yamada, Y. (2001) Metabolic engineering of plant alkaloid biosynthesis. *Proc. Natl. Acad. Sci. U.S.A.* 98, 367-372.
11 Frick, S., Kramell, R., and Kutchan, T. M. (2007) Metabolic engineering with a morphine biosynthetic P450 in opium poppy surpasses breeding. *Metab. Eng.* 9, 169-176.
12 Allen, R. S., Millgate, A. G., Chitty, J. A., Thisleton, J., Miller, J. A. C., Fist, A. J., Gerlach, W. L., and Larkin, P. J. (2004) RNAi-mediated replacement of morphine with the nonnarcotic alkaloid reticuline in opium poppy. *Nat. Biotechnol.* 22, 1559-1566.
13 Glenn, W. S., Runguphan, W., and O'Connor, S. E. (2013) Recent progress in the metabolic engineering of alkaloids in plant systems. *Curr. Opin. Biotechnol.* 24, 354-365.
14 Runguphan, W., and O'Connor, S. E. (2009) Metabolic reprogramming of periwinkle plant culture. *Nat. Chem. Biol.* 5, 151-153.
15 Runguphan, W., Qu, X. D., and O'connor, S. E. (2010) Integrating carbon-halogen bond formation into medicinal plant metabolism. *Nature* 468, 461-464.
16 Glenn, W. S., Nims, E., and O'Connor, S. E. (2011) Reengineering a Tryptophan Halogenase To Preferentially Chlorinate a Direct Alkaloid Precursor. *J. Am. Chem. Soc.* 133, 19346-19349.
17 Harvey, A. L. (2008) Natural products in drug discovery. *Drug Discovery Today* 13, 894-901.
18 Dewick, P. M. (2002) Medicinal natural products: a biosynthetic approach, 2nd ed., John Wiley & Sons Ltd.
19 Hawkins, K. M., and Smolke, C. D. (2008) Production of benzylisoquinoline alkaloids in *Saccharomyces cerevisiae*. *Nat. Chem. Biol.* 4, 564-573.
20 Minami, H., Kim, J. S., Ikezawa, N., Takemura, T., Katayama, T., Kumagai, H., and Sato, F. (2008) Microbial production of plant benzylisoquinoline alkaloids. *Proc. Natl. Acad. Sci. U.S.A.* 105, 7393-7398.
21 Nakagawa, A., Minami, H., Kim, J. S., Koyanagi, T., Katayama, T., Sato, F., and Kumagai, H. (2011) A bacterial platform for fermentative production of plant alkaloids. *Nat. Commun.* 2:326 doi: 10.1038/ncomms1327.
22 Fossati, E., Ekins, A., Narcross, L., Zhu, Y., Falgueyret, J. P., Beaudoin, G. A. W., Facchini, P. J., and Martin, V. J. J. (2014) Reconstitution of a 10-gene pathway for synthesis of the plant alkaloid dihydrosanguinarine in *Saccharomyces cerevisiae*. *Nat. Commun.* 5:3283 doi: 10.1038/ncomms4283.
23 Thodey, K., Galanie, S., and Smolke, C. D. (2014) A microbial biomanufacturing platform for natural and semisynthetic opioids. *Nat. Chem. Biol.* 10, 837-844
24 Fossati, E., Narcross, L., Ekins, A., Falgueyret, J. P., and Martin, V. J. J. (2015)
Synthesis of Morphinan Alkaloids in *Saccharomyces cerevisiae*. *PloS one* 10, DOI: 10.1371/journal.pone.0124459.
25 Nakagawa, A., Matsuzaki, C., Matsumura, E., Koyanagi, T., Katayama, T., Yamamoto, K., Sato, F., Kumagai, H., and Minami, H. (2014) (R, S)-Tetrahydropapaveroline production by stepwise fermentation using engineered *Escherichia coli*. *Sci Rep* 4 doi:10.1038/srep06695.
26 Hernandez-Romero, D., Sanchez-Amat, A., and Solano, F. (2006) A tyrosinase with an abnormally high tyrosine hydroxylase/dopa oxidase ratio—Role of the seventh histidine and accessibility to the active site. *Febs J.* 273, 257-270.
27 Luetke-Eversloh, T., Santos, C. N. S., and Stephanopoulos, G. (2007) Perspectives of biotechnological production of L-tyrosine and its applications. *Appl. Microbiol. Biotechnol.* 77, 751-762.
28 Land, E. J., Ramsden, C. A., and Riley, P. A. (2003) Tyrosinase autoactivation and the chemistry of ortho-quinone amines. *Accounts Chem. Res.* 36, 300-308.
29 DeLoache, W. C., Russ, Z. N., Narcross, L., Gonzales, A. M., Martin, V. J., and Dueber, J. E. (2015) An enzyme-coupled biosensor enables (S)-reticuline production in yeast from glucose. *Nat. Chem. Biol.* doi:10.1038/nchembio.1816.
30 Sun, X., Lin, Y., Yuan, Q., and Yan, Y. (2014) Precursor-Directed Biosynthesis of 5-Hydroxytryptophan Using Metabolically Engineered *E. coli*. *ACS Synth. Biol.* 4, 554-558.
31 Lin, Y. H., Sun, X. X., Yuan, Q. P., and Yan, Y. J. (2014) Engineering Bacterial Phenylalanine 4-Hydroxylase for Microbial Synthesis of Human Neurotransmitter Precursor 5-Hydroxytryptophan. *ACS Synth. Biol.* 3, 497-505.
32 Fitzpatrick, P. F. (1999) Tetrahydropterin-dependent amino acid hydroxylases. *Annu. Rev. Biochem.* 68, 355-381.
33 Werner-Felmayer, G., Golderer, G., and Werner, E. R. (2002) Tetrahydrobiopterin biosynthesis, utilization and pharmacological effects. *Curr. Drug Metab.* 3, 159-173.
34 Yamamoto, K., Kataoka, E., Miyamoto, N., Furukawa, K., Ohsuye, K., and Yabuta,
M. (2003) Genetic engineering of *Escherichia coli* for production of tetrahydrobiopterin. *Metab. Eng.* 5, 246-254.
35 Satoh, Y., Tajima, K., Munekata, M., Keasling, J. D., and Lee, T. S. (2012) Engineering of L-tyrosine oxidation in

*Escherichia coli* and microbial production of hydroxytyrosol. *Metab. Eng.* 14, 603-610.

36. Leiros, H. K. S., Pey, A. L., Innselset, M., Moe, E., Leiros, I., Steen, I. H., and Martinez, A. (2007) Structure of phenylalanine hydroxylase from *Colwellia psychrerythraea* 34H, a monomeric cold active enzyme with local flexibility around the active site and high overall stability. *J. Biol. Chem.* 282, 21973-21986.
37. Siddiqui, M. S., Thodey, K., Trenchard, I., and Smolke, C. D. (2012) Advancing secondary metabolite biosynthesis in yeast with synthetic biology tools. *Ferns Yeast Res.* 12, 144-170.
38. Chang, M. C. Y., Eachus, R. A., Trieu, W., Ro, D. K., and Keasling, J. D. (2007) Engineering *Escherichia coli* for production of functionalized terpenoids using plant P450s. *Nat. Chem. Biol.* 3, 274-277.
39. Miki, Y., and Asano, Y. (2014) Biosynthetic pathway for the cyanide-free production of phenylacetonitrile in *Escherichia coli* by utilizing plant cytochrome P450 79A2 and bacterial aldoxime dehydratase. *Appl. Environ. Microbiol.* 80, 6828-6836.
40. Barnes, H. J., Arlotto, M. P., and Waterman, M. R. (1991) Expression and Enzymatic-Activity of Recombinant Cytochrome-P450 17-Alpha-Hydroxylase in *Escherichia-Coli*. *Proc. Natl. Acad. Sci. U.S.A.* 88, 5597-5601.
41. Hong, K. K., and Nielsen, J. (2012) Metabolic engineering of *Saccharomyces cerevisiae*: a key cell factory platform for future biorefineries. *Cell Mol. Life Sci.* 69, 2671-2690.
42. Peralta-Yahya, P. P., Zhang, F. Z., del Cardayre, S. B., and Keasling, J. D. (2012) Microbial engineering for the production of advanced biofuels. *Nature* 488, 320-328.
43. Da Silva, N. A., and Srikrishnan, S. (2012) Introduction and expression of genes for metabolic engineering applications in *Saccharomyces cerevisiae*. *Fems Yeast Res.* 12, 197-214.
44. O'Connor, S. E., and Maresh, J. J. (2006) Chemistry and biology of monoterpene indole alkaloid biosynthesis. *Nat. Prod. Rep.* 23, 532-547.
45. Silvestrini, A., Pasqua, G., Botta, B., Monacelli, B., van der Heijden, R., and Verpoorte, R. (2002) Effects of alkaloid precursor feeding on a *Camptotheca acuminata* cell line. *Plant Physiol. Bioch.* 40, 749-753.
46. Friedrich, A., Brase, S., and O'Connor, S. E. (2009) Synthesis of 4-, 5-, 6-, and 7-azidotryptamines. *Tetrahedron Lett.* 50, 75-76.
47. Davis, M. D., Kaufman, S., and Milstien, S. (1988) The auto-oxidation of tetrahydrobiopterin. *Eur. J. Biochem.* 173, 345-351.
48. Thony, B., Auerbach, G., and Blau, N. (2000) Tetrahydrobiopterin biosynthesis, regeneration and functions. *Biochem. J.* 347, 1-16.
49. Wang, H. C., Yang, B., Hao, G. F., Feng, Y., Chen, H. Q., Feng, L., Zhao, J. X., Zhang, H., Chen, Y. Q., Wang, L., and Chen, W. (2011) Biochemical characterization of the tetrahydrobiopterin synthesis pathway in the oleaginous fungus *Mortierella alpina*. *Microbiology*. 157, 3059-3070.
50. Yim, J. J., and Brown, G. M. (1976) Characteristics of Guanosine Triphosphate Cyclohydrolase-I Purified from *Escherichia-Coli*. *J. Biol. Chem.* 251, 5087-5094.
51. Schoedon, G., Redweik, U., Frank, G., Cotton, R. G. H., and Blau, N. (1992) Allosteric Characteristics of Gtp Cyclohydrolase-I from *Escherichia-Coli*. *Eur. J. Biochem.* 210, 561-568.
52. Mancini, R., Saracino, F., Buscemi, G., Fischer, M., Schramek, N., Bracher, A., Becher, A., Gutlich, M., and Carbone, M. L. A. (1999) Complementation of the fol2 deletion in *Saccharomyces cerevisiae* by human and *Escherichia coli* genes encoding GTP cyclohydrolase I. *Biochem. Biophys. Res. Commun.* 255, 521-527.
53. Blau, N., and Niederwieser, A. (1986) The application of 8-aminoguanosine triphosphate, a new inhibitor of GTP cyclohydrolase I, to the purification of the enzyme from human liver. *Biochim. Biophys. Acta* 880, 26-31.
54. Hasler, T., and Curtius, H. C. (1989) Purification and characterization of 6-pyruvoyl tetrahydropterin synthase from salmon liver. *Eur. J. Biochem./FEBS* 180, 205-211.
55. Burgisser, D. M., Thony, B., Redweik, U., Hess, D., Heizmann, C. W., Huber, R., and Nar, H. (1995) 6-Pyruvoyl Tetrahydropterin Synthase, an Enzyme with a Novel Type of Active-Site Involving Both Zinc-Binding and an Intersubunit Catalytic Triad Motif—Site-Directed Mutagenesis of the Proposed Active-Center, Characterization of the Metal-Binding Site and Modeling of Substrate-Binding. *J. Mol. Biol.* 253, 358-369.
56. Ploom, T., Thony, B., Yim, J., Lee, S., Nar, H., Leimbacher, W., Richardson, J., Huber, R., and Auerbach, G. (1999) Crystallographic and kinetic investigations on the mechanism of 6-pyruvoyl tetrahydropterin synthase. *J. Mol. Biol.* 286, 851-860.
57. Glick, B. R. (1995) Metabolic Load and Heterologous Gene-Expression. *Biotechnol. Adv.* 13, 247-261.
58. Jones, K. L., Kim, S. W., and Keasling, J. D. (2000) Low-Copy Plasmids can Perform as Well as or Better Than High-Copy Plasmids for Metabolic Engineering of Bacteria. *Metab. Eng.* 2, 328-338.
59. Carkaci-Salli, N., Flanagan, J. M., Martz, M. K., Salli, U., Walther, D. J., Bader, M., and Vrana, K. E. (2006) Functional domains of human tryptophan hydroxylase 2 (hTPH2). *J. Biol. Chem.* 281, 28105-28112.
60. Brown, S., Clastre, M., Courdavault, V., and O'Connor, S. E. (2015) De novo production of the plant-derived alkaloid strictosidine in yeast. *Proc. Natl. Acad. Sci. U.S.A.* 112, 3205-3210.
61. Bernhardt, P., Usera, A. R., and O'Connor, S. E. (2010) Biocatalytic asymmetric formation of tetrahydro-beta-carbolines. *Tetrahedron Lett.* 51, 4400-4402.
62. Geerlings, A., Redondo, F. J., Contin, A., Memelink, J., van der Heijden, R., and Verpoorte, R. (2001) Biotransformation of tryptamine and secologanin into plant terpenoid indole alkaloids by transgenic yeast. *Appl. Microbiol. Biotechnol.* 56, 420-424.
63. Battersby A. R., Burnett, A. R., and Parsons, P. G. (1969) Alkaloid Biosynthesis Part XV. Partial Synthesis and Isolation of Vincoside and Isovincoside—Biosynthesis of 3 Major Classes of Indole Alkaloids from Vincoside. *J. Chem. Soc. C* 1193-1200.
64. Maresh, J. J., Giddings, L. A., Friedrich, A., Loris, E. A., Panjikar, S., Trout, B. L., Stockigt, J., Peters, B., and O'Connor, S. E. (2008) Strictosidine synthase: mechanism of a Pictet-Spengler catalyzing enzyme. *J. Am. Chem. Soc.* 130, 710-723.
65. McCoy, E., Galan, M. C., and O'Connor, S. E. (2006) Substrate specificity of strictosidine synthase. *Bioorg. Med. Chem. Lett.* 16, 2475-2478.
66. Miettinen, K., Dong, L. M., Navrot, N., Schneider, T., Burlat, V., Pollier, J., Woittiez, L., van der Krol, S., Lugan, R., Ilc, T., Verpoorte, R., Oksman-Caldentey, K. M., Martinoia, E., Bouwmeester, H., Goossens, A., Memelink, J., and Werck-Reichhart, D. (2014) The seco-iridoid pathway from *Catharanthus roseus*. *Nat. Commun.* 5:3606 doi: 10.1038/ncomms460.

67 Yerkes, N., Wu, J. X., McCoy, E., Galan, M. C., Chen, S., and O'Connor, S. E. (2008) Substrate specificity and diastereoselectivity of strictosidine glucosidase, a key enzyme in monoterpene indole alkaloid biosynthesis. *Bioorg. Med. Chem. Lett.* 18, 3095-3098.

68 Bernhardt, P., Yerkes, N., and O'Connor, S. E. (2009) Bypassing stereoselectivity in the early steps of alkaloid biosynthesis. *Org. Biomol. Chem.* 7, 4166-4168.

69 Dittrich, H. Kutcham, T. M. (1991) Molecular clonin, expression, and induction of berberine bridge enzyme, and enzyme essential to the formation of benzyophenanthridine alkaloids in the response of plants to pathogenic attack. *Proc. Natl. Acad. Sci. U.S.A.* 88, 9969-9973.

70 Luttik, M. A. H., Vuralhan, Z., Suir, E., Braus, G. H., Pronk, J. T. & Daran, J. M. (2008) Alleviation of feedback inhibition in *Saccharomyces cerevisiae* aromatic amino acid biosynthesis: Quantification of metabolic impact. *Metab Eng* 10, 141-153.

71 Gold, N. D., Gowen, C. M., Lussier, F. X., Cautha, S. C., Mahadevan, R. & Martin, V. J. (2015) Metabolic engineering of a tyrosine-overproducing yeast platform using targeted metabolomics. *Microb Cell Fact* 14, 73.

72 Sarria, S., Wong, B., Martin, H. G., Keasling, J. D. & Peralta-Yahya, P. (2014) Microbial Synthesis of Pinene. *ACS Synth. Biol.*, 3, 466-475.

73 Mukherjee, K., Bhattacharyya, S. & Peralta-Yahya, P. GPCR-Based Chemical Biosensors for Medium-Chain Fatty Acids. *ACS Synth. Biol.*, doi:10.1021/sb500365m (2015).

74 Belanger-Quintana, A., Burlina, A., Harding, C. O., and Muntau, A. C. (2011) Up to date knowledge on different treatment strategies for phenylketonuria. *Mol. Genet. Metab.* 104, S19-S25.

75 Byerley, W. F., Judd, L. L., Reimherr, F. W., and Grosser, B. I. (1987) 5-Hydroxytryptophan—a Review of Its Antidepressant Efficacy and Adverse-Effects. *J. Clin. Psychopharm.* 7, 127-137.

76 Birdsall, T. C. (1998) 5-Hydroxytryptophan: a clinically-effective serotonin precursor. *Alt. Med. Rev.: a journal of clinical therapeutic* 3, 271-280.

77 Bloom, F., and Kupfer, D. (1995) *Psychopharmacology, the fourth generation of progress* pp 933-944, Raven Press.

78 Connolly, B. S., and Lang, A. E. (2014) Pharmacological Treatment of Parkinson Disease A Review. JAMA, *J. Am. Med. Assoc.* 311, 1670-1683.

Example 4: Experimental Methods for Examples 1, 2 and 3

FIG. 34 shows an overview of the microbial synthesis of L-DOPA, dopamine, serotonin and 10-hydroxystrictosidine. Arrows represent presence of the enzyme. nd=not detectable. Amount produced is represented by the mean±standard deviation for samples run in triplicate. GTPCH: GTP cyclohydrolase; PTPS: pyruvoyl tetrahydropterin synthase; SR: sepiapterin reductase; PCD: pterin-4a-carbinolamine dehydratase; DHPR: dihydropteridine reductase; TPH: tryptophan hydroxylase; TH: tyrosine hydroxylase; DDC: aromatic-L-amino-acid decarboxylase; STR: strictosidine synthase Abbreviations used in Examples 1-2: GTPCH—GTP cyclohydrolase I; PTPS—pyruvoyl tetrahydropterin synthase; SR— sepiapterin reductase; PCD—pterin-4-alpha-carbinolamine dehydratase; DHPR—dihydropteridine reductase; TH—tyrosine hydroxylase; TPH—tryptophan hydroxylase; DDC—aromatic-L-amino-acid decarboxylase; STR—strictosidine synthase Yeast Strain Construction.

Construction of W303-Ade2+ strain. *S. cerevisiae* W303 were transformed with AME245 and AME246 via an adapted electroporation protocol. Transformed cells were plated and subsequently patched on synthetic complete media with 2% glucose lacking adenine (SD (Ade−)). To confirm the presence of a functional Ade2, genomic DNA from multiple patches was isolated, the mutation was amplified by PCR using primers AME128/AME247, and the PCR product sequenced with AME247.

Yeast transformation. A modified electroporation method[2] was utilized to transform *S. cerevisiae* W303 or W303-Ade2+. Modifications included no DNA precipitation step and immediately after electroporation, cells were rescued with YPD and left at room temperature overnight before plating on selection media plates.

Strains used are shown in Table 1.

TABLE 1

Table of Strains

| Strain # | Strain name | Description | Source |
|---|---|---|---|
| PPY11 | W303 | *S. cerevisiae* MATa ade2-1 ura3-1 his3-11 trp1-1 leu2-3 leu2-112 can1-100 | ATCC ® 20835 |
| PPY568 | W303-Ade2+ | *S. cerevisiae* W303 with a T190G mutation in Ade2 gene | This study |
| PPY752 | W303-172226 | W303 transformed with pAME17, pAME22, and pAME26 | This study |
| PPY753 | W303-172227 | W303 transformed with pAME17, pAME22, and pAME27 | This study |
| PPY754 | W303-172228 | W303 transformed with pAME17, pAME22, and pAME28 | This study |
| PPY755 | W303-172326 | W303 transformed with pAME17, pAME23, and pAME26 | This study |
| PPY756 | W303-172327 | W303 transformed with pAME17, pAME23, and pAME27 | This study |
| PPY757 | W303-172328 | W303 transformed with pAME17, pAME23, and pAME28 | This study |
| PPY758 | W303-172426 | W303 transformed with pAME17, pAME24, and pAME26 | This study |
| PPY759 | W303-172427 | W303 transformed with pAME17, pAME24, and pAME27 | This study |
| PPY760 | W303-172428 | W303 transformed with pAME17, pAME24, and pAME28 | This study |
| PPY761 | W303-172526 | W303 transformed with pAME17, pAME25, and pAME26 | This study |
| PPY762 | W303-172527 | W303 transformed with pAME17, pAME25, and pAME27 | This study |
| PPY763 | W303-172528 | W303 transformed with pAME17, pAME25, and pAME28 | This study |
| PPY764 | W303-182226 | W303 transformed with pAME18, pAME22, and pAME26 | This study |
| PPY765 | W303-182227 | W303 transformed with pAME18, pAME22, and pAME27 | This study |
| PPY766 | W303-182228 | W303 transformed with pAME18, pAME22, and pAME28 | This study |
| PPY767 | W303-182326 | W303 transformed with pAME18, pAME23, and pAME26 | This study |
| PPY768 | W303-182327 | W303 transformed with pAME18, pAME23, and pAME27 | This study |
| PPY797 | W303-182328 | W303 transformed with pAME18, pAME23, and pAME28 | This study |
| PPY798 | W303-182426 | W303 transformed with pAME18, pAME24, and pAME26 | This study |
| PPY799 | W303-182427 | W303 transformed with pAME18, pAME24, and pAME27 | This study |
| PPY800 | W303-182428 | W303 transformed with pAME18, pAME24, and pAME28 | This study |
| PPY801 | W303-182526 | W303 transformed with pAME18, pAME25, and pAME26 | This study |

TABLE 1-continued

Table of Strains

| Strain # | Strain name | Description | Source |
|---|---|---|---|
| PPY802 | W303-182527 | W303 transformed with pAME18, pAME25, and pAME27 | This study |
| PPY769 | W303-182528 | W303 transformed with pAME18, pAME25, and pAME28 | This study |
| PPY803 | W303-192226 | W303 transformed with pAME19, pAME22, and pAME26 | This study |
| PPY804 | W303-192227 | W303 transformed with pAME19, pAME22, and pAME27 | This study |
| PPY805 | W303-192228 | W303 transformed with pAME19, pAME22, and pAME28 | This study |
| PPY806 | W303-192326 | W303 transformed with pAME19, pAME23, and pAME26 | This study |
| PPY807 | W303-192327 | W303 transformed with pAME19, pAME23, and pAME27 | This study |
| PPY808 | W303-192328 | W303 transformed with pAME19, pAME23, and pAME28 | This study |
| PPY809 | W303-192426 | W303 transformed with pAME19, pAME24, and pAME26 | This study |
| PPY770 | W303-192427 | W303 transformed with pAME19, pAME24, and pAME27 | This study |
| PPY771 | W303-192428 | W303 transformed with pAME19, pAME24, and pAME28 | This study |
| PPY772 | W303-192526 | W303 transformed with pAME19, pAME25, and pAME26 | This study |
| PPY773 | W303-192527 | W303 transformed with pAME19, pAME25, and pAME27 | This study |
| PPY774 | W303-192528 | W303 transformed with pAME19, pAME25, and pAME28 | This study |
| PPY775 | W303-202226 | W303 transformed with pAME20, pAME22, and pAME26 | This study |
| PPY776 | W303-202227 | W303 transformed with pAME20, pAME22, and pAME27 | This study |
| PPY777 | W303-202228 | W303 transformed with pAME20, pAME22, and pAME28 | This study |
| PPY778 | W303-202326 | W303 transformed with pAME20, pAME23, and pAME26 | This study |
| PPY779 | W303-202327 | W303 transformed with pAME20, pAME23, and pAME27 | This study |
| PPY780 | W303-202328 | W303 transformed with pAME20, pAME23, and pAME28 | This study |
| PPY781 | W303-202426 | W303 transformed with pAME20, pAME24, and pAME26 | This study |
| PPY782 | W303-202427 | W303 transformed with pAME20, pAME24, and pAME27 | This study |
| PPY783 | W303-202428 | W303 transformed with pAME20, pAME24, and pAME28 | This study |
| PPY784 | W303-202526 | W303 transformed with pAME20, pAME25, and pAME26 | This study |
| PPY785 | W303-202527 | W303 transformed with pAME20, pAME25, and pAME27 | This study |
| PPY786 | W303-202528 | W303 transformed with pAME20, pAME25, and pAME28 | This study |
| PPY810 | W303-032930 | W303 transformed with pAME3, pAME29, and pAME30 | This study |
| PPY751 | W303-2226 | W303 transformed with pAME22, and pAME26 | This study |
| PPY787 | W303A-172226 | W303-Ade2+ transformed with pAME17, pAME22, and pAME26 | This study |
| PPY749 | W303A-57 | W303-Ade2+ transformed with pAME57 | This study |
| PPY788 | W303A-172252 | W303-Ade2+ transformed with pAME17, pAME22, and pAME52 | This study |
| PPY789 | W303A-175426 | W303-Ade2+ transformed with pAME17, pAME54, and pAME26 | This study |
| PPY790 | W303A-552226 | W303-Ade2+ transformed with pAME55, pAME22, and pAME26 | This study |
| PPY793 | W303A-175453 | W303-Ade2+ transformed with pAME17, pAME54, and pAME53 | This study |
| PPY792 | W303A-552253 | W303-Ade2+ transformed with pAME55, pAME22, and pAME53 | This study |
| PPY791 | W303A-555426 | W303-Ade2+ transformed with pAME55, pAME54, and pAME26 | This study |
| PPY750 | W303A-555453 | W303-Ade2+ transformed with pAME55, pAME54, and pAME53 | This study |
| PPY949 | W303A-17 | W303-Ade2+ expressing pAME17 | This study |
| PPY950 | W303A-55 | W303-Ade2+ expressing pAME55 | This study |
| PPY951 | W303A-22 | W303-Ade2+ expressing pAME22 | This study |
| PPY952 | W303A-54 | W303-Ade2+ expressing pAME54 | This study |
| PPY953 | W303A-26 | W303-Ade2+ expressing pAME26 | This study |
| PPY954 | W303A-53 | W303-Ade2+ expressing pAME53 | This study |
| PPY946 | W303A-946 | W303-Ade2+ transformed with pSS68, pESC-Leu2, pESC-His3, and pESC-Trp1 | This study |
| PPY646 | W303A-646 | W303-Ade2+ transformed with pAME17, pAME22PCD, pAME26DHPR, and pSS68 | This study |
| PPY679 | W303A-679 | W303-Ade2+ transformed with pAME17, pAME22, pAME26, and pSS68 | This study |
| PPY947 | W303A-947 | W303 Ade2+ transformed with pAME63, pSS68, pESC-His3, and pESC-Trp1 | This study |
| PPY658 | W303A-658 | W303-Ade2+ transformed with pSS66, pAME22PCD, pAME26DHPR, and pSS68 | This study |
| PPY743 | W303A-743 | W303 Ade2+ transformed with pSS66, pAME22, pAME26, and pSS68 | This study |
| PPY948 | W303A-948 | W303 Ade2+ transformed with pAME63, pSS70, pESC-His3, and pESC-Trp1 | This study |
| PPY649 | W303A-649 | W303-Ade2+ transformed with pSS66, pAME22PCD, pAME26DHPR, and pSS70 | This study |
| PPY741 | W303A-741 | W303-Ade2+ transformed with pSS66, pAME22, pAME26, and pSS70 | This study |
| PPY650 | W303A-650 | W303-Ade2+ transformed with pSS66, pAME22PCD, pAME26DHPR, and pSS71 | This study |
| PPY955 | W303A-955 | W303-Ade2+ transformed with pSS66, pAME22, pAME26, and pSS71 | This study |
| PPY744 | W303A-744 | W303 Ade2+ transformed with pAME56, pAME57, and pAME58 | This study |
| PPY748 | W303A-748 | W303Ade2+ transformed with pAME56, pAME57, and pESC-Ura3 | This study |
| PPY740 | W303A-740 | W303 Ade2+ transformed with pAME56 and pAME57 | This study |
| PPY827 | W303A-64 | W303 Ade2+ transformed with pAME64 | This study |
| PPY828 | W303A-ura | W303 Ade2+ transformed with pESC-Ura3 | This study |
| PPY835 | W303-835 | W303 transformed with pAME22, pAME26, and pSS68 | This study |
| PPY836 | W303-836 | W303 transformed with pAME17, pAME22, pAME26, and pSS68 | This study |

Vector Construction.

Construction of multi-copy vectors expressing the $BH_4$ synthetic pathway. To construct pAME18, 20, 22-26, and 28, genes were amplified from plasmids carrying codon-optimized nucleotide sequences of *M. alpina* GTPCH, *H. sapiens* GTPCH, *M. alpina* PTPS, *S. salar* PTPS, *S. ruber* PTPS, *P. mikurensis* PTPS, *M. alpina* SR, and *T. pseudonana* SR with primers AME143/AME144, AME141/AME139, AME149/AME150, AME147/AME148, AME151/AME152, AME153/AME154, AME165/AME166, or AME165/AME167, respectively, and cloned into pESC-Leu2 at BamHI/HindIII (pAME18, 20), pESC-Trp1 at BamHI/SacII (pAME22-25), or pESC-His3 at BamHI/SacII (pAME26, 28). To construct pAME17, *E. coli* GTPCH was amplified from the *E. coli* DH10B genome with primers AME163/164. The gene product was re-amplified with primers AME135/140 and cloned into pESC-Leu2 at BamHI/HindIII. To construct pAME19, *S. cerevisiae*

GTPCH was amplified from S. cerevisiae W303 genome with primers AME161/162, and re-amplified with primers AME137/142. The gene product was cloned into pESC-Leu2 at BamHI/HindIII. To construct pAME27, S. cerevisiae SR was amplified from S. cerevisiae W303 genome with primers AME168/169, and re-amplified with primers AME180/183. The gene product was cloned into pESC-His3 at BamHI/SacII. To construct pAME3, 29-30, green fluorescent protein (GFP) was amplified from pEGFP with primers AME123/124 and cloned into pESC-Leu2, pESC-Trp1, or pESC-His3, respectively, at BamHI/HindIII (Leu2) or BamHI/SacII (Trp1, His3). Constructs were sequence verified using primers AME104 and AME105.

Construction of single-copy vectors expressing $BH_4$ synthetic pathway. To construct pAME53-55, the region between terminators $T_{ADH1}$ and $T_{CYC1}$ was amplified from pAME26, 22, or 17 using primers AME184/AME185 and cloned into pRS413, pRS414, or pRS415, respectively, at BamHI/HindIII. Constructs were sequence verified using primers MH100 and MH101.

Construction of multi-copy vectors expressing $BH_4$ recycling pathway. To construct pAME22PCD and pAME26DHPR, PCD and DHPR genes were amplified from plasmids carrying the codon optimized genes with primers SS152/SS153 or AME241/AME242, respectively, and cloned into pAME22 or pAME26, respectively, at NotI/SacI. Constructs were sequence verified using primers AME229 and AME104.

Construction of multicopy vectors expressing alkaloid pathway enzymes from inducible-promoters. To construct pSS61, the STR gene was amplified from pSS42 with primers SS159/SS160 and cloned into pESC-Ura3 at BamHI/HindIII. To construct pSS66, the DDC gene was amplified from pSS62 with primers SS157/SS158 and cloned into pAME17 at NotI/SacI. To construct pSS68, the TH gene was amplified from pSS64 with primers SS179/SS180 and cloned into pESC-Ura3 at NotI/SacI. To construct pSS70, the TPH gene was amplified from pSS44 with primers SS207/SS208 and cloned into pESC-Ura3 at BamHI/HindIII. To construct pSS71, the TPH gene was amplified from pSS44 with primers SS177/SS178 and cloned into pSS61 at NotI/SacI. Constructs were sequence verified using primer SS112. To construct pAME63, the DDC gene was amplified from pSS62 with primers SS157/SS158 and cloned into pESC-Leu2 at NotI/SacI. To construct pAME64, the STR gene was amplified from pSS42 with primers SS159/AME406 and cloned into pESC-Ura3 at BamHI/HindIII. Constructs were sequence verified using primers AME229/AME230 (pAME63) or AME104/AME105 (pAME64).

Construction of multicopy vectors expressing alkaloid pathway enzymes from constitutive promoters. To construct pAME56-58, assembly similar to sewing PCR was utilized. Fragments were amplified from template plasmids using primers as follows (fragment-primer/primer/template):

SR-AME373/AME374/pAME26;
$P_{TEF1}$_$P_{HXT7}$-AME365/AME366/pSS102;
PTPS-AME363/AME364/pAME22;
$T_{HXT7}$-AME369/AME370/pSS102
$P_{ADH1g}$-AME371/AME372/pSS43;
$P_{ADH1ng}$-AME371/AME383/pSS43;
GTPCH-AME367/AME368/pAME17;
PCD-AME375/AME376/pAME22PCD;
DHPR-AME377/AME378/pAME26DHPR;
DDC-AME384/AME385/pSS66;
TPH-AME386/AME387/pSS70;
STR-AME388/AME389/pSS61;
vector-
AME394/AME395/pAME26DHPR, pAME22 PCD,pSS67.

After amplification, PCR products were gel purified. To create pAME56-58, fragments were sewn together using primers AME384/AME389 ($P_{TEF1}$_$P_{HXT7}$, $T_{HXT7}$, $P_{ADH1g}$, DDC, TPH, STR), AME363/AME374 ($P_{TEF1}$_$P_{HXT7}$, $T_{HXT7}$, $P_{ADH1g}$, GTPCH, PTPS, SR), and AME375/AME383 ($P_{TEF1}$_$P_{HXT7}$, $T_{HXT7}$, $P_{ADH1ng}$, PCD, DHPR), respectively, using a typical PCR protocol and equimolar amounts of fragments. Resulting products were gel purified and combined with respective vector fragments (from pAME22PCD, pAME26DHPR, pSS67, respectively) via Gibson assembly[1]. Sequencing was obtained using primers AME105/AME229/AME396/AME397/AME369/AME370/AME372.

Table 2 shows plasmids used in Examples 1-2 and Table 2 shows primers and primer sequences.

TABLE 2

Table of Plasmids

| Strain # | Plasmid | Description | Source |
|---|---|---|---|
| PPY34 | pESC-His3 | Yeast shuttle vector with divergent Gal1/Gal10 promoter | Agilent #217451 |
| PPY35 | pESC-Ura3 | Yeast shuttle vector with divergent Gal1/Gal10 promoter | Agilent #217454 |
| PPY36 | pESC-Trp1 | Yeast shuttle vector with divergent Gal1/Gal10 promoter | Agilent #217453 |
| PPY39 | pESC-Leu2 | Yeast shuttle vector with divergent Gal1/Gal10 promoter | Agilent #217452 |
| PPY13 | pRS413 | YC-type (centromeric) shuttle vector | ATCC ® 87518 |
| PPY14 | pRS414 | YC-type (centromeric) shuttle vector | ATCC ® 87519 |
| PPY15 | pRS415 | YC-typE (centromeric) shuttle vector | ATCC ® 87520 |
| PPY154 | pCR2.1_HGTPCH | Codon optimized* GTPCH from H. sapiens | This study |
| PPY156 | pCR2.1_MaGTPCH | Codon optimized* GTPCH from M. alpinas | This study |
| PPY171 | pCR2.1_MaPTS | Codon optimized* PTPS from M. alpinas | This study |
| PPY172 | pCR2.1_SPTS | Codon optimized* PTPS from S. salar | This study |
| PPY173 | pCR2.1_RubPTS | Codon optimized* PTPS from S. ruber | This study |
| PPY174 | pCR2.1_PmPTS | Codon optimized* PTPS from P. mikurensis | This study |
| PPY181 | pCR2.1_MaSR | Codon optimized* SR from M. alpina with N-terminal $His_6$-tag | This study |
| PPY182 | pCR2.1_PseudoSR | Codon optimized* SR from T. pseudonana with N-terminal $His_6$-tag | This study |
| PPY435 | pCR2.1_DHPR | Codon optimized* DHPR from H. sapiens | This study |
| PPY465 | pSS48 | Codon optimized* PCD from H. sapiens | This study |
| PPY539 | pSS62 | Codon optimized* DDC from S. scrofa | This study |
| PPY563 | pSS64 | Codon optimized* Th from M. musculus | This study |
| PPY444 | pSS44 | Codon optimized* TPH from H. sapiens | This study |

TABLE 2-continued

Table of Plasmids

| Strain # | Plasmid | Description | Source |
|---|---|---|---|
| PPY442 | pSS42 | Codon optimized (for E. coli) STR from O. pumila | Commercially synthesized for this study. Sequence from Bernhardt et al. |
| PPY38 | pEGFP | Enhanced green fluorescent protein | F. Storici lab |
| PPY40 | pAME3 | pESC-Leu2-$P_{GAL1}$-eGFP | This study |
| PPY242 | pAME29 | pESC-Trp1-$P_{GAL1}$-eGFP | This study |
| PPY243 | pAME30 | pESC-His3-$P_{GAL1}$-eGFP | This study |
| PPY183 | pAME17 | pESC-Leu2-$P_{GAL1}$-His$_6$-E. coli_GTPCH | This study |
| PPY168 | pAME18 | pESC-Leu2-$P_{GAL1}$-His$_6$-M. alpina_GTPCH | This study |
| PPY184 | pAME19 | pESC-Leu2-$P_{GAL1}$-His$_6$-S. cerevisiae_GTPCH | This study |
| PPY166 | pAME20 | pESC-Leu2-$P_{GAL1}$-His$_6$-H. sapiens_GTPCH | This study |
| PPY186 | pAME22 | pESC-Trp1-$P_{GAL1}$-His$_6$-M. alpina_PTPS | This study |
| PPY187 | pAME23 | pESC-Trp1-$P_{GAL1}$-His$_6$-S. salar_PTPS | This study |
| PPY188 | pAME24 | pESC-Trp1-$P_{GAL1}$-His$_6$-S. ruber_PTPS | This study |
| PPY189 | pAME25 | pESC-Trp1-$P_{GAL1}$-His$_6$-P. mikurensis_PTPS | This study |
| PPY190 | pAME26 | pESC-His3-$P_{GAL1}$-His$_6$-M. alpina_SR | This study |
| PPY241 | pAME27 | pESC-His3-$P_{GAL1}$-His$_6$-S. cerevisiae_SR | This study |
| PPY191 | pAME28 | pESC-His3-$P_{GAL1}$-His$_6$-T. pseudonana_SR | This study |
| PPY670 | pAME53 | pRS413-His3-$P_{GAL1}$-His$_6$-M. alpina_SR | This study |
| PPY667 | pAME54 | pRS414-Trp1-$P_{GAL1}$-His$_6$-M. alpina_PTPS | This study |
| PPY668 | pAME55 | pRS415-Leu2-$P_{GAL1}$-His$_6$-E. coli_GTPCH | This study |
| PPY520 | pAME22PCD | PESC-Trp1-$P_{GAL1}$-His$_6$-M. alpina_PTPS-$P_{GAL10}$-H. sapiens_PCD | This study |
| PPY555 | pAME26DHPR | pESC-His3-$P_{GAL1}$-His$_6$-M. alpina_SR-$P_{GAL10}$-H. sapiens_DHPR | This study |
| PPY538 | pSS61 | pESC-Ura3-$P_{GAL1}$-STR | This study |
| PPY572 | pSS66 | pESC-Leu2-$P_{GAL1}$-His$_6$-E. coli_GTPCH-$P_{GAL10}$-DDC | This study |
| PPY574 | pSS68 | pESC-Ura3-$P_{GAL10}$-TH | This study |
| PPY630 | pSS70 | pESC-Ura3-$P_{GAL1}$-TPH | This study |
| PPY631 | pSS71 | pESC-Ura3-$P_{GAL1}$-STR-$P_{GAL10}$-TPH | This study |
| PPY700 | pAME56 | pESC-Trp1-$P_{HXT7}$-DDC-$P_{TEF1}$-TPH-$P_{ADH1}$-STR | This study |
| PPY704 | pAME57 | pESC-His3-$P_{HXT7}$-PTPS-$P_{TEF1}$-GTPCH-$P_{ADH1}$-SR | This study |
| PPY701 | pAME58 | pESC-Ura3-$P_{HXT7}$-PCD-$P_{TEF1}$-DHPR | This study |
| PPY723 | pAME63 | pESC-Leu2-$P_{GAL10}$-DDC | This study |
| PPY338 | pSS102 | pESC-Ura3-$P_{HXT7}$/$P_{TEF1}$ | This study |
| PPY443 | pSS43 | pESC-Trp1-$P_{TEF1}$/$P_{ADH1}$ | This study |
| PPY573 | pSS67 | pESC-Ura3-$P_{GAL10}$-TH-$P_{GAL1}$NCS | This study |
| PPY822 | pAME64 | pESC-Ura3-$P_{GAL1}$-STR-His$_6$ | This study |

TABLE 3

Table of Primers

| Name | Sequence (5'→3') |
|---|---|
| AME104 | CACTTTAACTAATACTTTCAAC |
| AME105 | TAAATAACGTTCTTAATACTAAC |
| AME123 | CGTCAAGGAGAAAAAACCCCGGATCCATCACGTGCACCATGGTGAGCAAGGGCGAG |
| AME124 | TCTTAGCTAGCCGCGGTACCAAGCTTTTACTTGTACAGCTCGTCC |
| AME128 | CTGGAGAAGGGTAAATTTTTA |
| AME135 | TCTTAGCTAGCCGCGGTACCAAGCTTTTAGTTGTGATGACGCACAGC |
| AME137 | TCTTAGCTAGCCGCGGTACCAAGCTTTTAAATACTTCTTCTTCCTAAAAG |
| AME139 | TCTTAGCTAGCCGCGGTACCAAGCTTTTAAGATCTAATCAAAGTCAAG |
| AME140 | CGTCAAGGAGAAAAAACCCCGGATCCATCACGTGCACCATGCATCACCATCACCATCACCCATCACTCAGTAAAGAAGC |
| AME141 | CGTCAAGGAGAAAAAACCCCGGATCCATCACGTGCACCATGCATCACCATCACCATCACGAGAAAGGTCCAGTTAGAG |
| AME142 | CGTCAAGGAGAAAAAACCCCGGATCCATCACGTGCACCATGCATCACCATCACCATCACCATAACATCCAATTAGTGCAA |

TABLE 3-continued

Table of Primers

| Name | Sequence (5'→3') |
|---|---|
| AME143 | CGTCAAGGAGAAAAAACCCCGGATCCATCACGTGCACCATGCATCACCATCACCATCAC TCCCATACTCCAACCTCTC |
| AME144 | TCTTAGCTAGCCGCGGTACCAAGCTTTTAAACACCTCTTCTTCTAATC |
| AME147 | CGTCAAGGAGAAAAAACCCCGGATCCATCACGTGCACCATGCATCACCATCACCATCAC GCTCAAGCTGATTCCAGAA |
| AME148 | TCTTAGCTAGCCGCGGTACCAAGCTTTTATTCACCTCTGTAGACAAC |
| AME149 | CGTCAAGGAGAAAAAACCCCGGATCCATCACGTGCACCATGCATCACCATCACCATCAC ACCTCCTCAACTCCAGTTA |
| AME150 | TCTTAGCTAGCCGCGGTACCAAGCTTTTATTCACCTCTGTAAACGAC |
| AME151 | CGTCAAGGAGAAAAAACCCCGGATCCATCACGTGCACCATGCATCACCATCACCATCAC TCCACCGTTTACATTACCAG |
| AME152 | TCTTAGCTAGCCGCGGTACCAAGCTTTTATTCACCTCTGTATTCAAC |
| AME153 | CGTCAAGGAGAAAAAACCCCGGATCCATCACGTGCACCATGCATCACCATCACCATCAC TTTGAATTGACTAGAACTTTAAG |
| AME154 | TCTTAGCTAGCCGCGGTACCAAGCTTTTAACCACCTCTATAAGCAC |
| AME161 | CATAACATCCAATTAGTGCAA |
| AME162 | AATACTTCTTCTTCCTAAAAG |
| AME163 | CCATCACTCAGTAAAGAAGC |
| AME164 | GTTGTGATGACGCACAGC |
| AME165 | CGTCAAGGAGAAAAAACCCCGGATCCATCACGTGCACCATGCATCACCATCACCATC |
| AME166 | TCTTAGCTAGCCGCGGTACCAAGCTTTTATTCATCGTAGAAATCAATAT |
| AME167 | TCTTAGCTAGCCGCGGTACCAAGCTTTTAAACATCGAAGTAATCAACA |
| AME168 | GGTAAAGTTATTTTAGTTACAG |
| AME169 | AGGCATAAAGTCCGCCAAG |
| AME180 | TCTTAGCTAGCCGCGGTACCAAGCTTTTAAGGCATAAAGTCCGCCAAG |
| AME183 | CGTCAAGGAGAAAAAACCCCGGATCCATCACGTGCACCATGCATCACCATCACCATCAC GGTAAAGTTATTTTAGTTACAG |
| AME184 | TCGAGGTCGACGGTATCGATAAGCTTGAGCGACCTCATGCTATAC |
| AME185 | GCGGCCGCTCTAGAACTAGTGGATCCCTTCGAGCGTCCCAAAAC |
| AME229 | ACGTATCTACCAACGATTTG |
| AME230 | GTATATGGATATGTATATGGTG |
| AME241 | AATTCAACCCTCACTAAAGGGCGGCCGCATGGCAGCTGCTGCAGC |
| AME242 | GGCGAAGAATTGTTAATTAAGAGCTCTTAGAAATAAGCTGGAGTCAA |
| AME245 | GGCTCCTTTTCCAATCCTCTTGATATCGAAAAACTAGCTGAAAAATGTGATGTGCTAACG ATTGAGATTGAGCATGTTGA |
| AME246 | TCAACATGCTCAATCTCAATCGTTAGCACATCACATTTTTCAGCTAGTTTTTCGATATCA AGAGGATTGGAAAAGGAGCC |
| AME247 | AAGACGGTAATACTAGATGC |
| AME363 | TGTAATCCATCGATACTAGTTTATTCACCTCTGTAAACGAC |
| AME364 | ATTTTAATCAAAAGCGACCATGACCTCCTCAACTCCAG |
| AME365 | GGTCGCTTTTTGATTAAAATTAAAAAAACTTT |
| AME366 | GGTGGCTGTAATTAAAAACTTAGATTAGATT |

TABLE 3-continued

Table of Primers

| Name | Sequence (5'→3') |
|---|---|
| AME367 | AAGTTTTAATTACAGCCACCATGCCATCACTCAGTAAAGA |
| AME368 | TTAATAAAAGTGTTCGCAAATTAGTTGTGATGACGCACAG |
| AME369 | TTTGCGAACACTTTTATTAATTC |
| AME370 | TCTTTAAAGTTTCTTTGTCTCC |
| AME371 | AGACAAAGAAACTTTAAAGAATCCTTTTGTTGTTTCCGGG |
| AME372 | GGTCGGTGTATATGAGATAGTTGATTGT |
| AME373 | CTATCTCATATACACCGACCATGTCATCCAAAGAACATCAT |
| AME374 | CCTATAGTGAGTCGTATTACTTATTCATCGTAGAAATCAATATG |
| AME375 | TGTAATCCATCGATACTAGTTTAAGTCATGGAGACAGCG |
| AME376 | ATTTTAATCAAAAAGCGACCATGGCTGGTAAAGCTCATAG |
| AME377 | AAGTTTTAATTACAGCCACCATGGCAGCTGCTGCAGC |
| AME378 | TTAATAAAAGTGTTCGCAAATTAGAAATAAGCTGGAGTCAA |
| AME383 | CCTATAGTGAGTCGTATTACTGTATATGAGATAGTTGATTGT |
| AME384 | TGTAATCCATCGATACTAGTTTAAGATTTAATTTCAGCTTTAC |
| AME385 | ATTTTAATCAAAAAGCGACCATGAATGCTTCTGATTTTAGAA |
| AME386 | AAGTTTTAATTACAGCCACCATGGAAGAATTGGAAGATGTT |
| AME387 | TTAATAAAAGTGTTCGCAAATTAAGTATCCTTCAAAATTTCAA |
| AME388 | CTATCTCATATACACCGACCATGGGCTCTCCTGAGTTTT |
| AME389 | CCTATAGTGAGTCGTATTACTTAAGATCCAAACGAAGAGAA |
| AME394 | GTAATACGACTCACTA |
| AME395 | ACTAGTATCGATGGATTACAA |
| AME396 | CATTTGCAGCTATTGTAAAATA |
| AME397 | CTCAAGTTTCAGTTTCATTTTT |
| AME406 | TCTTAGCTAGCCGCGGTACCTTAGTGATGGTGATGGTGATGAGATCCAAACGAAGAGAAC |
| AME441 | CACAAGGGTCCATAACAGC |
| AME442 | ACGGTCATAATTACAAGGTTG |
| AME443 | CGATGAAATGGTCACCGTG |
| AME444 | GACAGACCGATCACCGAAT |
| AME445 | CTGGCAAGAAGCTAGATCC |
| AME446 | GTTCTATGATCTGGATATTGTT |
| SS112 | GACAACCTTGATTGGAGA |
| SS152 | GGCGAAGAATTGTTAATTAATTAAGTCATGGAGACAGC |
| SS153 | AATTCAACCCTCACTAAAGGATGGCTGGTAAAGCTC |
| SS157 | TGGCGAAGAATTGTTAATTAATTAAGATTTAATTTCAGCTTTACCTTC |
| SS158 | GAATTCAACCCTCACTAAAGGATGAATGCTTCTGATTTTAGAAG |
| SS159 | CGTCAAGGAGAAAAAACCCCATGGGCTCTCCTGAG |
| SS160 | TCTTAGCTAGCCGCGGTACCTTAAGATCCAAACGAAGAGA |
| SS177 | GGCGAAGAATTGTTAATTAATTAAGTATCCTTCAAAATTTCAATG |

TABLE 3-continued

Table of Primers

| Name | Sequence (5'→3') |
|---|---|
| SS178 | AATTCAACCCTCACTAAAGGATGGAAGAATTGGAAGATGT |
| SS179 | GGCGAAGAATTGTTAATTAATTAAGAAATAGCAGACAATGCT |
| SS180 | AATTCAACCCTCACTAAAGGATGCCAACTCCATCC |
| SS207 | CGTCAAGGAGAAAAAACCCCATGGAAGAATTGGAAGATGT |
| SS208 | TCTTAGCTAGCCGCGGTACCTTAAGTATCCTTCAAAATTTCAATG |
| MH100 | ACGTTGTAAAACGACGGCC |
| MH101 | CTATGACCATGATTACGCC |
| ACT1-F | TTGGATTCCGGTGATGGTGT |
| ACT1-R | CGGCCAAATCGATTCTCAAA |

Below are sequences for various components of the biocatalyst described herein. Underlining within a sequence demonstrates the nucleotides corresponding to a His$_6$ Tag. The sequences below are codon-optimized for yeast. Where a UniProt database code is provided, this is referencing the sequence that was used as the input sequence for the yeast codon-optimization and does not necessarily refer to the specific sequences below.

*Escherichia coli* GTP cyclohydrolase I (UniProtKB-P0A6T5).

SEQ ID NO: 1

ATG<u>CATCACCATCACCATCAC</u>CCATCACTCAGTAAAGAAGCGGCCCTGGTTCATGAAGCGTTAGTTGCGC

GAGGACTGGAAACACCGCTGCGCCCGCCCGTGCATGAAATGGATAACGAAACGCGCAAAAGCCTTATTGC

TGGTCATATGACCGAAATCATGCAGCTGCTGAATCTCGACCTGGCTGATGACAGTTTGATGGAAACGCCG

CATCGCATCGCTAAAATGTATGTCGATGAAATTTTCTCCGGTCTGGATTACGCCAATTTCCCGAAAATCA

CCCTCATTGAAAACAAAATGAAGGTCGATGAAATGGTCACCGTGCGCGATATCACTCTGACCAGCACCTG

TGAACACCATTTTGTTACCATCGATGGCAAAGCGACGGTGGCCTATATCCCGAAAGATTCGGTGATCGGT

CTGTCAAAAATTAACCGCATTGTGCAGTTCTTTGCCCAGCGTCCGCAGGTGCAGGAACGTCTGACGCAGC

AAAATTCTTATTGCGCTACAAACGCTGCTGGGCACCAATAACGTGGCTGTCTCGATCGACGCGGTGCATTA

CTGCGTGAAGGCGCGTGGCATCCGCGATGCAACCAGTGCCACGACAACGACCTCTCTTGGTGGATTGTTC

AAATCCAGTCAGAATACGCGCCACGAGTTTCTGCGCGCTGTGCGTCATCACAACTAA

*Mortierella alpina* GTP cyclohydrolase I (UniProtKB-G3FNL6)

SEQ ID NO: 2

ATG<u>CATCACCATCACCATCAC</u>TCCCATACTCCAACCTCTCCAAAGACCGCTTCCTCTGTTGAATTGGTTC

ATCCAACCGCAAAGCAAGCATTGTTGAACCACGCTTTGACTGGTCATTCCCATTCCTCTGGTAGATCCTA

CTTGAAGTCCGAATCTCCAGAAGGTAGATCCGCTACTCCAATTGATTTCGACGGTTTATCCTTTCCATCC

ATTGGTGCTAGAGATAGAAGAGAAGATACCGAAGAACAAAGAGCTGCTAGAATTGAGAAGATAGCTGGTT

CCGTTAGAACCATTTTGGAGTGTATTGGTGAAGATCCAGATAGAGAAGGTTTGTTGAAGACTCCAGAAAG

ATACGCTAAGGCATTGATGTTCTTCTCCAAAGGTTACGAAGAATCCGTTACTCATTTGATGAATAAGGCA

TTATTTCAAGAAGATCACGACGAAATGGTTATTGTTAAAGATATTGACGTTTTCTCCTTGTGTGAACATC

ATATGGTTCCATTTACTGGTAAGATTCATATTGGTTACATTCCAAAGAACGGTAAGGTTGTTGGTTTGTC

CAAAATTGCTAGATTGGCTGAAATGTTTTCCAGAAGATTGCAAGTTCAAGAAAGATTGACCAAACAAGTT

GCTATGGCTTTGCAAGAATTGTTAGATCCATTGGGTGTTGCTGTTGTTATGGAAGCATCTCATTTCTGTA

TGGTTATGAGAGGTGTTCAAAAGCCAGGTTCTCAAACCATTACCTCCTCTATGTTTGGTTGTTTTAGAGA

TCAAGGTAAAACCAGAGAAGAGTTCTTGTCCTTGATTAGAAGAAGAGGTGTTTAA

*Saccharomyces cerevisiae* GTP cyclohydrolase I (UniProtKB-P51601)

SEQ ID NO: 3

ATG<u>CATCACCATCACCATCAC</u>CATAACATCCAATTAGTGCAAGAGATAGAAAGACATGAAACCCGTTAA

ACATTAGACCTACCTCTCCATACACTTTAAACCCTCCTGTCGAGAGAGATGGGTTTTCTTGGCCAAGTGT

GGGTACAAGACAACGTGCAGAGGAAACTGAAGAGGAGGAAAAGGAACGAATTCAACGCATTTCAGGCGCT

ATCAAGACAATTTTGACCGAACTGGGTGAAGATGTCAACAGAGAAGGTCTACTAGATACTCCACAAAGAT

ACGCTAAAGCCATGCTTTATTTCACTAAAGGTTACCAAACGAACATTATGGACGATGTCATTAAGAATGC

TGTCTTTGAAGAAGATCATGATGAAATGGTTATTGTTCGTGATATTGAAATTTACTCGTTATGTGAACAT

CATTTGGTGCCATTTTTCGGCAAGGTTCATATCGGGTATATACCAAATAAAAAAGTCATCGGGTTAAGTA

AGTTGGCCAGATTGGCAGAAATGTATGCGAGAAGGCTCCAAGTTCAAGAAAGACTTACAAAGCAAATTGC

AATGGCCCTAAGTGATATTCTAAAACCATTAGGTGTAGCCGTTGTTATGGAAGCTTCTCATATGTGCATG

GTTTCAAGAGGCATTCAAAAAACGGGATCTTCTACGGTAACTTCTTGTATGCTTGGAGGGTTTAGGGCTC

ATAAAACAAGAAGAGTTTTTAACTCTTTTAGGAAGAAGAAGTATTTAA

*Homo sapiens* GTP cyclohydrolase I (UniProtKB-P30793-1)

SEQ ID NO: 4

ATG<u>CATCACCATCACCATCAC</u>GAGAAAGGTCCAGTTAGAGCTCCAGCAGAGAAGCCAAGAGGTGCTAGAT

GTTCTAACGGATTTCCAGAAAGAGATCCTCCAAGACCAGGTCCTTCTAGACCAGCTGAGAAACCACCTAG

ACCAGAAGCTAAATCTGCTCAACCAGCTGACGGTTGGAAAGGTGAAAGACCAAGATCTGAAGAGGACAAC

GAATTGAATCTACCAAATCTAGCTGCCGCTTATTCATCTATCTTGTCTTCCTTGGGAGAGAATCCACAAA

GACAAGGTCTATTGAAGACTCCTTGGAGAGCTGCCTCTGCTATGCAATTCTTTACTAAAGGTTATCAAGA

AACTATTTCTGACGTTTTGAACGACGCAATCTTCGACGAGGATCACGACGAGATGGTTATTGTCAAAGAT

ATTGATATGTTCTCTATGTGTGAACACCACTTGGTTCCATTTGTTGGTAAAGTTCACATTGGTTATTTGC

CTAATAAGCAAGTTTTGGGTTTGTCTAAATTGGCTAGAATTGTTGAAATCTATTCTAGAAGATTGCAAGT

TCAAGAAAGATTGACTAAACAAATTGCTGTTGCTATTACTGAAGCATTGAGACCAGCAGGTGTTGGTGTT

GTCGTTGAAGCTACTCACATGTGTATGGTTATGAGAGGTGTTCAGAAGATGAACTCTAAGACTGTTACTT

CTACTATGTTGGGTGTCTTTAGAGAAGATCCAAAGACTAGAGAAGAGTTCTTGACTTTGATTAGATCTTA

A

*Mortierella alpina* 6-pyruvoyl tetrahydrobiopterin synthase (UniProtKB-G3FNL7)

SEQ ID NO: 5

ATG<u>CATCACCATCACCATCAC</u>ACCTCCTCAACTCCAGTTAGAACTGCTTACGTTACCAGAATTGAACATT

TCTCCGCTGCTCATAGATTGAATTCCGTTCATTTGTCTCCTGCTGAAAACGTTAAGTTGTTCGGTAAGTG

TAATCATACTTCCGGTCACGGTCATAATTACAAGGTTGAAGTTACCATTAAAGGTCAAATTAATCCACAA

TCCGGTATGGTTATTAACATTACCGATTTGAAGAAGACCTTGCAAGTTGCTGTTATGGACCCTTGTGATC

ATAGAAATTTGGATATTGATGTTCCATACTTCGAATCCAGACCATCCACCACTGAAAACTTGGCTGTCTT

CTTGTGGGAAAACATTAAGTCCCATTTGCCACCATCCGATGCTTACGATTTGTACGAAATTAAGTTGCAC

GAAACCGATAAGAACGTTGTCGTTTACAGAGGTGAATAA

*Salmo salar* 6-pyruvoyl tetrahydrobiopterin synthase (UniProtKB-B5XE18)

SEQ ID NO: 6

ATG<u>CATCACCATCACCATCAC</u>GCTCAAGCTGATTCCAGAAACGAAGTTGCTGAAAGAATTGGTTACATTA

CCAGAGTTCAATCCTTCTCCGCTTGTCATAGATTGCATTCCCCAACCTTGTCCGATGAAGTCAACAAGAG

AATCTTCGGTAAGTGTAACAATCCAAACGGTCACGGTCATAACTACAAGGTTGAAGTCACCGTCAGAGGT

AAGATTGATAGACATACTGGTATGGTCATGAACATTACCGATTTGAAGCAACATATTGAAGAAGTCATTA

TGATTCCATTGGATCATAAGAATTTGGATAAGGACGTTCCATACTTTGCTAACGTTGTCTCTACTACCGA

AAACGTTGCTGTCTACATTTGGGATAACATGGTTAAGCAATTGCCAGCTAACTTGTTGTACGAAGTTAAG

ATTCACGAAACCGATAAGAACATTGTTGTCTACAGAGGTGAATAA

-continued

*Salinibacter ruber* 6-carboxy-5,6,7,8-tetrahydropterin synthase (UniProtKB- Q2RYU6)
SEQ ID NO: 7

ATG<u>CATCACCATCACCATCAC</u>TCCACCGTTTACATTACCAGAAAGGTTCATTTCAACGCTGCTCATAGAT

TGCATAATCCAAATAAGTCCGATGCTTGGAACGAAGATACCTACGGTAAGGATAACAATCCAAACTGGCA

TGGTCATAACTACGAATTGGAAGTCACCGTTGCTGGTGAACCAGATCCAGAAACCGGTTACGTTGTCGAT

TTGGGTGTCTTGAAGGATATTTTGCATGATAGAGTTTTGGATAAGGTTGATCATAAGAACTTGAACTTGG

AAGTCGATTTCATGGATGGTGTTATTCCTTCCTCTGAAAACTTCGCTATTGCTATTTGGAATGAAATTGA

AGATGCTTTGCCAAACGGTGAATTGCATTGTGTCAGATTGTACGAAACTCCAAGAAACTTCGTTGAATAC

AGAGGTGAATAA

*Phycisphaera mikurensis* Putative 6-pyruvoyl tetrahydrobiopterin synthase
(UniProtKB-I0IIJ5)
SEQ ID NO: 8

ATG<u>CATCACCATCACCATCAC</u>TTTGAATTGACTAGAACTTTAAGATTTTGTCCATCTGGTGATCCAGGTG

CTCCAAGAGATAACGCTCATGCTGCTTGGCCACCACCAAGAGGTTTAGCAGGTGTATTATCTTTAGATTT

GACTATTGCTGGTAGACCAGATCCAGGTACTGGTGTTTTATTGAACGTTAAAGATTTAGATGCAGCTTTT

GCTGCCGCTGCATTACCAAGATTCAGAGCAGCTGCAGGTGCTGAACCAGCAGGTTTATTGAGAGGTGTTG

CTCAAGCATTAGCTCCTACTTTACCATTTCCATTGTTAAGATTGAGATTATCTGCATCTGCTTCAGCTTC

TACTGAATTGAGACCAGCTGATATGTCTAGAGTTATTTTGAGACAAAGATTCTCTTTCTCTGCTGCTCAT

AGATTACAAGCTGATGCTTTGTCTGAAGAGGAAAATAGAACATTGTTTGGTAAGTGTAATAGACCATCTT

TTCATGGTCATAATTACGAATTAGAAGTTGCTGCAGCCGCTGCTATTGCTCCAGATGGTAGATCTTTAGA

ACCAGCTGCATTAGATGCTGCTGTTAGAACTAGAGTCATTGATACTTTAGATCATAGAAATTTGAATACT

GATGTTGCTGCTTTTGCTACTAGAAATCCAACTGTTGAACATATTGCTCAAACTTGTTGGGATTTGTTAG

CTGGTGGTTTACCAGAAGGTGCAGAATTACAAGAAGTTGTAGTTTGGGAAACTGATAGAACATCTTGTGC

TTATAGAGGTGGTTAA

*Mortierella alpina* Sepiapterin reductase (UniProtKB-G3FNL8)
SEQ ID NO: 9

ATG<u>CATCACCATCACCATCAC</u>TCATCCAAAGAACATCATTTGGTTATTATTAACGGTGTTAATAGAGGTT

TTGGTCATTCCGTTGCATTGGATTACATAAGACATTCAGGTGCTCATGCTGTTTCCTTTGTTTTGGTTGG

TAGAACTCAACATTCCTTGGAACAAGTTTTGACTGAATTGCATGAAGCTGCATCTCATGCTGGTGTTGTC

TTCAAGGGTGTCGTTGTCTCCGAAGTTGATTTGGCTCATTTGAACTCTTTGGATTCTAATTTGGCTAGAA

TACAATCTGCTGCAGCTGATTTGAGAGACGAAGCTGCACAATCTACCAGAACTATTACTAAGTCTGTTTT

GTTTAATAACGCTGGTTCATTGGGTGATTTGTCCAAGACTGTTAAGGAATTTACCTGGCAAGAAGCTAGA

TCCTACTTGGATTTCAACGTCGTTTCCTTAGTTGGTTTGTGTTCCATGTTCTTGAAGGATACCTTGGAAG

CATTTCCAAAGGAACAATATCCAGATCATAGAACTGTTGTCGTTTCCATTTCTTCCTTGTTAGCTGTTCA

AGCATTCCCAAATTGGGGTTTGTACGCTGCAGGTAAGGCAGCTAGAGATAGATTGTTAGGTGTTATTGCT

TTGGAAGAAGCAGCTAATAACGTTAAGACCTTGAATTACGCTCCAGGTCCATTGGATAACGAAATGCAAG

CTGATGTTAGAAGAACCTTGGGTGATAAAGAACAATTGAAGATTTACGATGATATGCATAAGTCTGGTTC

CTTGGTTAAGATGGAAGATTCCTCTAGAAAAGTTGATTCATTTGTTAAAGGCTGATACCTTCACCTCCGGT

GGTCATATTGATTTCTACGATGAATAA

*Saccharomyces cerevisiae* Putative cytoplasmic short-chain dehydrogenase/reductase
(UniProtKB-P40579)
SEQ ID NO: 10

ATG<u>CATCACCATCACCATCAC</u>GGTAAAGTTATTTTAGTTACAGGTGTTTCCAGAGGTATCGGTAAGTCCA

TCGTGGATGTTCTTTTCAGTTTGGACAAGGACACGGTTGTTTACGGTGTAGCCAGGTCTGAGGCACCCTT

GAAGAAGTTGAAAGAGAAGTATGGCGACAGGTTTTTTTACGTTGTCGGTGATATTACCGAGGATTCCGTG

TTGAAGCAGTTGGTTAACGCTGCTGTTAAGGGCCACGGCAAGATCGACTCCTTGGTTGCCAACGCTGGTG

TCCTAGAGCCCGTGCAAAATGTCAACGAGATTGATGTCAACGCTTGGAAGAAGCTGTATGACATCAACTT

CTTCAGCATTGTTTCCTTGGTTGGCATTGCGTTACCTGAATTGAAGAAGACCAACGGTAACGTGGTATTC

GTCAGTTCGGACGCCTGTAACATGTACTTCAGCAGTTGGGGAGCTTACGGTTCTTCAAAAGCCGCTCTGA

ACCACTTCGCCATGACTCTGGCCAACGAGGAAAGGCAAGTGAAAGCCATTGCCGTCGCCCCAGGTATTGT

GGACACAGATATGCAAGTTAACATTAGGGAGAACGTGGGGCCTTCCTCCATGAGTGCAGAGCAATTGAAG

ATGTTTAGAGGTTTAAAGGAGAATAACCAGTTGCTGGATAGCTCTGTGCCAGCTACAGTTTATGCCAAAT

GGCCCTTCATGGTATTCCTGACGGTGTTAATGGACAGTACTTGAGCTATAATGACCCTGCCTTGGCGGA

CTTTATGCCTTAA

*Thalassiosira pseudonana* Sepiapterin reductase (UniProtKB-B8BVR3)
SEQ ID NO: 11

ATGCATCACCATCACCATCACCAAACAAGGAAAACGATGAAACCTCCATTGTTGTCGATATTCATGAAA

TGGATTTGTCCGATTTGGATATTTTGGCTGTTAACATGAAGTTGTTGTTTGAATTCTACACCAAGGTTAC

CAAGTACAATCAATGTTGGTTGTTCAACAATGCTGGTTCCTTGGGTCCATTGGGTCCAACCTTGTCCTTG

TGTAACGGTGATCCATTGAGATTAATGCAAGATTTGAAGAAAGCTGTTGATTTGAACGTTACCTCCGCTA

CCTGGATTTCCTCACAATTCGTTTCCACCTTTGGTTCCTCTCATAAGGACGATACTCCACCATTGGTTAG

AATTGTTAACATTTCTTCCTTGTGTGCTATTGAACCATTCCAAACTATGGCTGTTTACTGTATGGGTAAG

GCTGCAAGAGATATGTACCATTTGGTTTTGGCTAAAGAACATAAGGATTCCGATACTATGAAAGTTTTGA

ACTACGCTCCAGGTCCTTGTGATACTGAAATGACTGATGTTTTGGCTGGTTCTGCTGTTTTGGATTGGGA

TTTGCATCAATATTACGCTACATCCAAGAGAGATCAAAAGTTGGTTGATCCTTTGGATTCTGCTAAGAAA

TTGATTGAATTGTTAGAAAAGGATGAATTCACCACAGGTTCCCATGTTGATTACTTCGATGTTTAA

*Homo sapiens* Pterin-4-alpha-carbinolamine dehydratase (UniProtKB-P61457)
SEQ ID NO: 12

ATGGCTGGTAAAGCTCATAGATTGTCTGCTGAAGAAAGAGATCAATTGTTGCCAAACTTGAGAGCTGTTG

GTTGGAACGAATTGGAAGGTAGAGATGCTATTTTCAAGCAATTCCATTTCAAAGATTTCAATAGAGCCTT

CGGTTTCATGACTAGAGTTGCCTTGCAAGCTGAAAAGTTAGATCATCATCCAGAATGGTTCAACGTCTAC

AATAAGGTCCATATTACCTTGTCCACTCATGAATGTGCTGGTTTGTCTGAAAGAGATATTAACTTGGCAT

CCTTCATTGAACAAGTCGCTGTCTCCATGACTTAA

*Homo sapiens* Dihydropteridine reductase (UniProtKB-P09417-1)
SEQ ID NO: 13

ATGGCAGCTGCTGCAGCCGCTGGTGAAGCTAGAAGAGTTTTGGTTTACGGTGGTAGAGGTGCTTTGGGTT

CTAGATGTGTCCAAGCATTCAGAGCTAGAAATTGGTGGGTTGCTTCTGTTGATGTCGTTGAAAACGAAGA

AGCATCTGCTTCTATTATTGTTAAAATGACTGATTCTTTTACTGAACAAGCTGATCAAGTTACTGCTGAA

GTTGGTAAATTGTTAGGTGAAGAGAAAGTTGATGCTATTTTGTGTGTTGCTGGTGGTTGGGCTGGTGGTA

ACGCTAAATCTAAATCTTTGTTTAAGAATTGTGATTTGATGTGGAAACAATCTATTTGGACTTCTACTAT

TTCTTCTCATTTGGCTACTAAACATTTGAAAGAAGGTGGTTTGTTAACTTTGGCAGGTGCTAAAGCTGCT

TTGGATGGTACTCCAGGTATGATTGGTTACGGTATGGCTAAAGGTGCAGTTCATCAATTGTGTCAATCTT

TGGCTGGTAAGAACTCTGGTATGCCACCTGGTGCAGCTGCTATTGCTGTTTTGCCAGTTACTTTGGATAC

ACCAATGAATAGAAAATCTATGCCAGAAGCTGATTTCTCTTCTTGGACTCCATTGGAATTCTTGGTTGAA

ACTTTTCATGATTGGATTACTGGAAAGAATAGACCATCTTCTGGTTCTTTGATTCAAGTTGTTACTACTG

AAGGTAGAACTGAATTGACTCCAGCTTATTTCTAA

*Mus musculus* Tyrosine 3-monooxygenase (UniProtKB-P24529)
SEQ ID NO: 14

ATGCCAACTCCATCCGCTTCCTCCCCACAACCAAAGGGTTTCAGACGCGCTGTGTCTGAACAAGATACTA

AGCAAGCTGAAGCTGTTACTTCCCCAAGATTCATCGGTAGAAGACAATCTTTGATTGAAGATGCTAGAAA

```
GGAAAGAGAAGCTGCAGCTGCAGCCGCTGCAGCCGCTGTTGCTTCTGCTGAACCAGGTAATCCATTGGAA

GCTGTTGTCTTCGAAGAAAGAGATGGTAATGCTGTTTTGAATTTGTTGTTCTCTTTGAGAGGTACTAAGC

CATCTTCCTTGTCTAGAGCTCTAAAGGTATTCGAAACTTTCGAAGCTAAGATTCATCATTTGGAAACTAG

ACCTGCACAAAGACCATTGGCTGGTTCCCCACATTTGGAATACTTCGTTAGATTTGAAGTTCCATCCGGT

GATTTGGCTGCTTTGTTGTCTTCCGTTAGAAGAGTTTCTGATGATGTTAGATCCGCTAGAGAAGATAAGG

TTCCTTGGTTTCCAAGAAAGGTTTCTGAATTGGATAAGTGTCATCATTTGGTTACTAAGTTTGATCCAGA

TTTGGATTTGGATCATCCAGGTTTCTCCGATCAAGCATACAGACAAAGAAGAAAGTTGATTGCTGAAATT

GCTTTCCAATACAAGCAAGGTGAACCAATTCCACATGTTGAATACACTAAGGAAGAAATTGCTACTTGGA

AGGAAGTTTACGCTACTTTGAAGGGTTTGTACGCTACTCATGCTTGTAGAGAACATTTGGAAGCATTTCA

ATTGTTGGAAAGATACTGTGGTTACAGAGAAGATTCTATTCCACAATTGGAAGATGTTTCTCATTTCTTG

AAGGAAAGAACTGGTTTCCAATTGAGACCAGTTGCTGGTTTGTTGTCCGCTAGAGATTTCTTGGCTTCCT

TGGCTTTCAGAGTTTTCCAATGTACTCAATACATTAGACATGCTTCCTCCCCAATGCATTCTCCAGAACC

AGATTGTTGTCATGAATTGTTGGGTCATGTTCCAATGTTGGCTGATAGAACTTTCGCTCAATTCTCTCAA

GATATTGGTTTGGCTTCTTTGGGTGCTTCTGATGAAGAAATTGAAAAGTTGTCCACTGTTTACTGGTTTA

CTGTTGAATTTGGTTTGTGTAAGCAAAATGGTGAATTGAAGGCTTACGGTGCCGGATTGTTGTCCTCTTA

CGGTGAATTGTTGCATTCTTTGTCTGAAGAACCAGAAGTTAGAGCTTTCGATCCAGATACTGCTGCTGTT

CAACCATACCAAGATCAAACTTACCAACCAGTTTACTTCGTTTCTGAATCTTTCTCTGATGCTAAGGATA

AGTTGAGAAATTACGCTTCTAGAATCCAAAGACCATTCTCTGTTAAGTTTGATCCATACACTTTGGCTAT

TGATGTCTTGGATTCTCCACATACTATTAGAAGATCTTTGGAAGGTGTTCAAGATGAATTGCATACTTTG

ACTCAAGCATTGTCTGCTATTTCTTAA

Homo sapiens Tryptophan-5-hydroxylase 2 isoform 1 AA145-460 (UniProtKB-Q8IWU9-
1)
                                                                      SEQ ID NO: 15
ATGGAAGAATTGGAAGATGTTCCTTGGTTCCCAAGAAAGATTTCCGAATTGGATAAGTGTTCCCATAGAG

TTTTGATGTATGGTTCCGAATTGGATGCTGATCATCCAGGTTTCAAGGATAATGTTTACAGACAAAGAAG

AAAGTACTTCGTTGATGTTGCTATGGGTTACAAGTACGGTCAACCAATTCCAAGAGTTGAATACACTGAA

GAAGAAACTAAGACTTGGGGCGTTGTGTTCAGAGAATTGTCCAAGTTGTACCCAACTCATGCTTGTAGAG

AATACTTGAAGAATTTCCCATTGTTGACTAAGTACTGTGGTTACAGAGAAGATAATGTTCCACAATTGGA

AGATGTTTCCATGTTCTTGAAGGAAAGATCCGGTTTCACTGTTAGACCAGTTGCTGGTTACTTGTCCCCA

AGAGATTTCTTGGCTGGTTTGGCTTACAGAGTCTTCCATTGTACTCAATACATTAGACATGGTTCCGATC

CATTGTACACTCCAGAACCAGATACTTGTCATGAATTGTTGGGTCATGTTCCATTGTTGGCTGATCCAAA

GTTCGCTCAATTCTCCCAAGAAATTGGTTTGGCTTCCTTGGGTGCTTCCGATGAAGATGTTCAAAAGTTG

GCTACTTGTTACTTCTTCACTATTGAATTCGGTTTGTGTAAGCAAGAAGGTCAATTGAGAGCTTACGGTG

CTGGTTTGTTATCCTCTATTGGTGAATTGAAGCACGCTTTGTCCGATAAGGCTTGTGTTAAGGCTTTCGA

CCCAAAGACTACTTGTTTGCAAGAATGTTTGATTACTACTTTCCAAGAAGCATACTTCGTTTCCGAATCC

TTCGAAGAAGCTAAGGAGAAGATGAGAGATTTCGCTAAGTCCATTACTAGACCATTCTCCGTTTACTTCA

ATCCATACACTCAATCCATTGAAATTTTGAAGGATACTTAA

Sus scrofa Aromatic-L-amino-acid decarboxylase (UniProtKB-P80041)
                                                                      SEQ ID NO: 16
ATGAATGCTTCTGATTTTAGAAGGAGAGGTAAAGAAATGGTTGACTACATGGCTGATTACTTGGAAGGTA

TTGAAGGTAGACAAGTTTACCCAGATGTTCAACCAGGTTACTTGAGACCATTGATTCCAGCTACTGCTCC

ACAAGAACCAGATACTTTTGAAGATATTTTGCAAGATGTTGAGAAGATTATTATGCCAGGTGTCACACAT

TGGCACTCGCCATACTTCTTTGCTTACTTCCCAACTGCTTCCTCCTACCCAGCTATGTTGGCTGATATGT
```

```
TGTGTGGTGCTATTGGTTGTATTGGTTTCTCCTGGGCTGCTTCCCCAGCTTGTACTGAATTGGAAACTGT

TATGATGGATTGGTTGGGTAAAATGTTGCAATTGCCAGAAGCCTTCTTGGCTGGTGAAGCTGGTGAAGGT

GGTGGTGTTATTCAAGGTTCCGCTTCCGAAGCTACTTTGGTTGCTTTGTTGGCTGCTAGAACTAAAGTTA

CTAGAAGATTGCAAGCTGCTTCTCCAGGTTTGACTCAAGGTGCTGTTTTGGAGAAGTTGGTTGCTTACGC

CTCCGACCAAGCTCATTCCTCCGTTGAAAGAGCTGGTTTGATTGGTGGTGTTAAATTGAAAGCTATTCCA

TCCGATGGTAAATTTGCTATGAGAGCTTCCGCTTTGCAAGAAGCCTTGGAAAGAGATAAAGCTGCTGGTT

TGATTCCATTCTTCGTTGTTGCTACTTTGGGTACTACTTCCTGTTGTTCCTTTGATAATTTGTTGGAAGT

TGGTCCAATTTGTCATGAAGAAGATATTTGGTTGCATGTTGATGCTGCTTACGCTGGTTCCGCTTTCATT

TGTCCAGAATTTAGACATTTGTTGAATGGTGTTGAATTTGCTGATTCCTTTAATTTCAATCCACATAAAT

GGTTGTTGGTTAATTTTGATTGTTCCGCTATGTGGGTTAAAAGAAGAACTGATTTGACTGGTGCTTTTAA

ATTGGACCCAGTTTACTTGAAACATTCCCATCAAGGTTCCGGTTTGATTACTGATTACAGACATTGGCAA

TTGCCATTGGGTAGAAGATTTAGATCCTTGAAAATGTGGTTTGTCTTCAGAATGTACGGTGTTAAAGGTT

TGCAAGCCTACATTAGAAAGCATGTTCAATTGTCCCATGAATTTGAAGCCTTTGTTTTGCAAGATCCAAG

ATTTGAAGTTTGTGCTGAAGTTACTTTGGGTTTGGTTTGTTTTAGATTGAAAGGTTCCGATGGTTTGAAT

GAGGCTTTGTTGGAAAGAATTAATTCCGCTAGAAAGATTCATTTGGTTCCATGTAGATTGAGAGGTCAAT

TTGTTTTGAGATTTGCTATTTGTTCCAGAAAAGTTGAATCCGGTCATGTTAGATTGGCTTGGGAACATAT

TAGAGGTTTGGCTGCTGAATTGTTGGCTGCTGAAGAAGGTAAAGCTGAAATTAAATCTTAA
```

Ophiorrhiza pumila Strictosidine synthase AA26-350, His$_6$ only included in pAME64
(UniProtKB-Q94LW9)[7]
SEQ ID NO: 17

```
ATGGGCTCTCCTGAGTTTTTCGAATTTATTGAAGCACCGTCTTATGGTCCAAATGCGTATGCGTTCGACA

GCGACGGCGAGTTGTATGCGAGCGTGGAAGACGGTCGTATTATCAAGTACGACAAGCCTTCTAACAAATT

CCTGACTCATGCTGTTGCCAGCCCGATCTGGAACAATGCCCTGTGTGAGAATAATACCAACCAAGACCTG

AAGCCGCTGTGCGGTCGCGTCTACGACTTTGGTTTTCATTATGAAACGCAGCGCCTGTACATTGCAGATT

GCTACTTCGGCTTGGGCTTTGTTGGTCCGGACGGCGGTCACGCGATTCAACTGGCAACCTCCGGTGATGG

CGTTGAGTTCAAGTGGCTGTACGCGTTGGCGATCGACCAACAGGCAGGCTTCGTCTACGTGACGGACGTT

TCTACTAAGTACGATGATCGTGGTGTTCAGGACATTATTCGCATTAATGATACCACGGGTCGCCTGATTA

AGTATGACCCTTCGACCGAAGAGGTGACCGTGCTGATGAAAGGCCTGAATATTCCGGGCGGTACCGAGGT

TAGCAAAGACGGTAGCTTTGTGCTGGTTGGTGAGTTCGCGTCGCATCGTATCCTGAAGTACTGGCTGAAG

GGTCCGAAGGCCAATACCAGCGAGTTTCTGCTGAAGGTGCGCGGTCCAGGTAATATCAAACGTACCAAAG

ATGGTGATTTCTGGGTTGCGTCCAGCGATAACAACGGCATCACGGTGACGCCACGTGGTATCCGCTTCGA

TGAGTTTGGCAACATTCTGGAGGTCGTTGCTATTCCGCTGCCGTATAAAGGTGAACATATCGAGCAGGTC

CAAGAACACGACGGCGCCCTGTTCGTGGGTAGCCTGTTTCATGAGTTCGTCGGCATCCTGCATAACTATA

AGAGCAGCGTTGACCATCATCAGGAAAAGAACTCGGGTGGTCTGAACGCGAGCTTCAAGGAGTTCTCTTC

GTTTGGATCTCATCACCATCACCATCACTAG
```

Reagents. Tetrahydrobiopterin, dihydrobiopterin, and biopterin were purchased from Cayman Chemical (81880, 81882, and 10007662). Dopamine and vanillin were purchased from Alfa Aesar (A11136 and A11169). L-DOPA and serotonin were purchased from TCI America (D0600 and S0370). Secologanin and tryptophan were purchased from Sigma-Aldrich (50741-5MG-F and T0254). 5-chlorotryptamine was purchased from Ark Pharm, Inc. (AK-32281).

Microbial synthesis of tetrahydrobiopterin. Overnight cultures of strains PPY750, 752-793 and 797-810 in synthetic complete media with 2% glucose lacking histidine, tryptophan, and leucine (SD (HWL⁻)) were used to inoculate 5 mL of synthetic complete media with 2% galactose lacking histidine, tryptophan, and leucine (SCgal (HWL⁻)) to $OD_{600}$=0.1 and incubated for 136 hours at 30° C. (250 rpm). Overnight culture of strain PPY749 in synthetic complete media with 2% glucose lacking histidine (SD (H⁻)) was used to inoculate 5 mL of synthetic complete media with 2% galactose lacking histidine (SCgal (H⁻)) to $OD_{600}$=0.1 and incubated for 136 hours at 30° C. (250 rpm). Overnight culture of strain PPY751 in synthetic complete media with 2% glucose lacking histidine and tryptophan (SD (HW⁻)) was used to inoculate 5 mL of synthetic complete media with 2% galactose lacking histidine and tryptophan (SCgal (HW⁻)) to $OD_{600}$=0.1 and incubated for 136 hours at 30° C. (250 rpm). After incubation, cultures were centrifuged for 5 min at 3230×g, the supernatant was filtered, vanillin was added as an internal standard and samples were analyzed via LC/MS. For quantification of biopterin in L-DOPA, dopamine, and serotonin-producing strains, 5-chlorotryptamine was used as an internal standard.

Microbial synthesis of L-DOPA, dopamine, serotonin, and hydroxystrictosidine. Overnight cultures of strains PPY646, 649-650, 658, 679, 741, 743, 946-948, and 955 in synthetic complete media with 2% glucose lacking histidine, tryptophan, leucine, and uracil (SD (HWLU⁻)) were used to inoculate 5 mL of synthetic complete media with 2% galactose lacking histidine, tryptophan, leucine, and uracil (SCgal (HWLU⁻)) to $OD_{600}$=0.1. Overnight cultures of strains PPY744 and 748 in SD (HWU⁻) were used to inoculate 5 mL of fresh SD (HWU⁻) to $OD_{600}$=0.1. Overnight culture of strain PPY740 in SD (HW⁻) was used to inoculate 5 mL of fresh SD (HW⁻) to $OD_{600}$=0.1. For hydroxystrictosidine production (strains PPY649, 650, 740, 741, 744, 748, and 955), secologanin (solution in water) was added at the time of inoculation to a final concentration of 0.4 mM (150 mg/L). After inoculation, all strains were incubated for 136 hours at 30° C. (250 rpm). The cultures were then centrifuged for 5 min at 3230×g, the supernatant was filtered, 5-chlorotryptamine (L-DOPA, dopamine, serotonin) or vanillin (hydroxystrictosidine) was added as an internal standard, and the samples were analyzed via LC/MS.

Biopterin quantification. LC/MS analysis was completed using an Agilent 1100/1260 series system equipped with a 1260 ALS autosampler and a 6120 Single Quadrupole LC/MS with a Poroshell 120 SB-Aq 3.0×100 mm×2.7 μM column and an electrospray ion source. LC conditions: Solvent A—150 mM acetic acid with 0.1% formic acid and Solvent B—methanol with 0.1% formic acid. Gradient: 4 min ramp from 95%:5%:0.2 (A:B: flow rate in mL/min) to 70%:30%:0.2, 6 min ramp to 40%:60%:0.2, 2 min ramp to 2%:98%:0.2, 2 min ramp to 2%:98%:0.5, 4 min at 2%:98%:0.5, 1 min ramp to 95%:5%:0.5, 7 min at 95%:5%:0.5, and 1.5 min post time. MS acquisition (positive ion mode) included 25% scan from m/z 100-600, 25% scan from m/z 230-260, 25% scan from m/z 145-165, and 25% Selected Ion Monitoring (SIM) for $BH_4$ (m/z 242.1), dihydrobiopterin (m/z 240.1), biopterin (m/z 238.1), and vanillin (m/z 153.1). Quantitation was performed by obtaining the area under the peak in the extracted ion chromatogram (EIC) for the desired m/z value from the SIM signal. For biopterin quantification in L-DOPA-, dopamine-, and serotonin-producing strains, 5-chlorotryptamine (m/z 195.1) was used as an internal standard instead of vanillin. Area was converted to concentration using a standard curves produced from commercially available biopterin. Retention times were determined using commercially available standards.

Quantification of L-DOPA, dopamine and serotonin. LC/MS system and solvent composition was the same as the one used in the analysis of biopterin. LC gradient: 8 min ramp from 95%:5%:0.05 to 70%:30%:0.05, 6 min ramp to 40%:60%:0.05, 1 min ramp to 40%:60%:0.1, 9 min ramp to 2%:98%:0.1, 1 min at 2%:98%:0.1, 5 min ramp to 2%:98%: 0.3, 0.1 min ramp to 2%:98%:0.5, 3.9 min at 2%:98%:0.5, 1 min ramp to 95%:5%:0.5, 7 min at 95%:5%:0.5, and 3.5 min post time. MS acquisition (positive ion mode) included 33% scan from m/z 100-600, 33% scan from m/z 120-240, and 33% SIM for DOPA (m/z 198.2), dopamine (m/z 154.2), hydroxytryptophan (m/z 221.2), serotonin (m/z 177.2), and 5-chlorotryptamine (m/z 195.1). Quantitation was performed by obtaining the area under the peak in the EIC for the desired m/z value from the SIM signal. Area was converted to concentration using standard curves produced from commercially available L-DOPA, dopamine and serotonin dissolved in media taken from a culture of strain PPY810 grown under the same conditions as production samples. Traces used for the L-DOPA standard curve were background subtracted using just media. Retention times were determined using commercially available standards.

Analysis of hydroxystrictosidine. High resolution mass spectrometry (HRMS) and tandem mass spectrometry (MS/MS) analysis of hydroxystrictosidine was performed at the Mass Spectrometry Facility at Georgia Tech. MS/MS was done using a Waters Quattro LC Mass Spectrometer with a Gemini 2×150 mm 5 μm C18 column from Phenomenex. LC conditions: Solvent A: 95%:5% water:acetonitrile; Solvent B: 5%:95% water:acetonitrile. Gradient: 7 min at 100%:0% (A:B), 37 min ramp to 0%:100%, 8 min at 0%:100%, 1 min ramp to 100%:0%, and 7 min at 100%:0%. Flow rate was 0.2 mL/min. HRMS was done using a Thermo LTQ Orbitrap XL equipped with a Nano ACQUITY UPLC with a BEH130 300 μm×100 mm 1.7 μm C8 column from Waters. Solvent A: 10 mM ammonium acetate in water; Solvent B: acetonitrile. Gradient: 5 min at 95%:5% (A:B), 40 min ramp to 70%:30%, 5 min at 70%:30%, 2 min ramp to 5%:95%, 3 min at 5%:95%, 1 min ramp to 95%:5%, and 4 min at 95%:5%. Flow rate was 8 μL/min. Multiple Reaction Monitoring (MRM) was done on the Waters Quattro LC Mass Spectrometer using the same column and LC gradient using Solvent A—95%:5%:0.1% water:acetonitrile:formic acid and Solvent B—5%:95%:0.1%. MRM parameters: hydroxystrictosidine—transition 547.60→530.00, cone voltage 20V, collision energy 35 eV; transition 547.60→298.00, cone voltage 20V, collision energy 35 eV; vanillin-transition 152.80→92.80, cone voltage 25V, collision energy 15 eV; transition 152.80→124.80, cone voltage 25V, collision energy 15 eV; camptothecin—transition 349.10→305.00, cone voltage 45V, collision energy 35 eV; transition 349.10→220.00, cone voltage 45V, collision energy 40 eV. Reported hydroxystrictosidine counts obtained using 547.60→530.00 transition.

Hydroxystrictosidine isomer ratios. For the chemical reactions, secologanin and serotonin were mixed to a final concentration of 0.4 mM each in pH=3 or pH=7 phosphate buffer (135 mM NaCl, 2.7 mM KCl, 4.3 mM $Na_2HPO_4$, 1.4 mM $KH_2PO_4$). Solutions were mixed and incubated for 136 hours at 30° C. (250 rpm). After incubation, solutions were analyzed using LC/MS. For lysate experiments, an overnight culture of PPY827 was used to inoculate SCgal (U⁻) to $OD_{600}$=0.1. The culture was incubated for 24 hours at 30° C. (250 rpm). After incubation, the culture was centrifuged at 3230×g for 5 min, the supernatant was removed, and pellet was resuspended in 1.5 mL phosphate buffer. The pellet was lysed by sonication using a Misonix Sonicator 3000 at 5.0 output level for 20 sec, 20 sec rest, for a total 6 pulses. The lysate was centrifuged and supernatant collected. The pH of the lysate was adjusted to either pH=3 or pH=7 and secologanin and serotonin were added to a final concentration of 0.4 mM each. After mixing, the lysates were incubated for 136 hours at 30° C. (250 rpm), after which the lysates were analyzed using LC/MS. For in vivo intact cell experiments, overnight cultures of strains PPY827 and PPY828 in SD (U⁻) were used to inoculate 5 mL of SCgal (U⁻) or SCgal (U⁻) buffered with 25 mM $K_2HPO_4$ (pH=7) to $OD_{600}$=0.1. Secologanin and serotonin were added to a final concentration of 0.4 mM each and cultures were incubated for 136 hours at 30° C. (250 rpm). After incubation, all cultures were centrifuged for 5 min at 3230×g, the supernatant was filtered, and analyzed via LC/MS. The column compartment was kept constant at 28° C. LC/MS analysis was completed on the Agilent system described above. Gradient: 0.25 min ramp from 95%:5% (A:B) to 70%:30%, 4.75 min ramp to 68%:32%, 2 min ramp to 30%:70%, 1 min at 30%:70%, 0.50 min ramp to 95%:5%, and 5.5 min at 95%:5%. Flow rate was 0.4 mL/min. MS acquisition (positive ion mode) included 30% scan from m/z 100-600 and 70% SIM for ions related to alkaloid formation (dopamine—m/z 154; tryptamine—m/z 161; serotonin—m/z 177; tyrosine—m/z 182; L-DOPA—m/z 198; tryptophan—m/z 205; 5-hydroxytryptophan—m/z 221; strictosidine—m/z 531; hydroxystrictosidine—m/z 547).

Yeast cell lysis for intracellular biopterin determination. After 136 h of microbial production, cultures were centrifuged at 3230 g for 5 min. The supernatant was removed and filtered with a 0.2 µm filter. The pellet was frozen at −80° C., thawed, washed with 1 mL water, and resuspended in 250 µL water. 250 µL 0.2M NaOH was mixed in and the cells remained at room temperature for 10 minutes. The lysate was centrifuged and filtered. Both supernatant and lysate were analyzed using liquid chromatography/mass spectrometry (LC-MS).

Statistical analysis. Two-tailed, paired T-tests were performed in Microsoft Excel.

Determining SR open reading frame from *T. pseudonana*. As only a portion of the amino acid sequence is known for the predicted SR from *T. pseudonana*, we searched upstream and downstream of the sequence in the genome to obtain a complete open reading frame.

Amino acid limiting experiments. Overnight cultures of strain PPY649 and PPY646 in synthetic media containing 2% glucose and lacking histidine, leucine, uracil, and tryptophan (SD (HWUL-)) was used to inoculate 5 mL of synthetic media containing 2% galactose and lacking histidine, leucine, uracil, and tryptophan (SCgal (HWUL⁻)) to $OD_{600}$=0.1. Tryptophan was added to strain PPY649 (final concentrations 0-640 mg/L) and tyrosine was added to strain PPY646 (final concentrations 30-960 mg/L). Cultures were incubated for 136 hours at 30° C. (250 rpm). After incubation, cultures were centrifuged for 5 min at 3230 g. Supernatant was removed, filtered and analyzed via LC-MS analysis. 5-chlorotryptamine was used as an internal standard.

Determination of GTPCH, PTPS, and SR mRNA levels. Overnight cultures of strain PPY949-950 in synthetic complete media with 2% glucose lacking leucine (SD (L⁻)) was used to inoculate 5 mL of synthetic complete media with 2% galactose lacking leucine (SCgal (L⁻)) to $OD_{600}$=0.1 and incubated overnight at 30° C. (250 rpm). Overnight cultures of strain PPY951-952 in synthetic complete media with 2% glucose lacking tryptophan (SD (W⁻)) was used to inoculate 5 mL of synthetic complete media with 2% galactose lacking tryptophan (SCgal (W⁻)) to $OD_{600}$=0.1 and incubated overnight at 30° C. (250 rpm). Overnight cultures of strain PPY953-954 in synthetic complete media with 2% glucose lacking histidine (SD (H⁻)) was used to inoculate 5 mL of synthetic complete media with 2% galactose lacking histidine (SCgal (H⁻)) to $OD_{600}$=0.1 and incubated overnight at 30° C. (250 rpm). Total RNA for all cultures was extracted using a RNeasy Mini Kit (Qiagen) following the manufacturer's protocol for isolation from yeast using $3 \times 10^7$ cells per culture. RNA quantity was measured using a NanoDrop Lite. 1 µg of total RNA was taken from each strain and converted into cDNA using QuantiTect® reverse transcription kit (Qiagen) using manufacturer's instructions. Relative expression levels of GFP were quantified using QuantiTect® SYBR Green PCR kit (Qiagen) using manufacturer's instructions for LightCyclers 1.x and 2.0 with 150 ng cDNA per reaction. Duplicate reactions were set up for each strain. Quantification was completed using a StepOnePlus Real-time PCR system (Applied Biosystems) with primers AME443/AME444 (GTPCH), AME441/AME442 (PTPS), AME445/AME446 (SR), and ACT-F/ACT-R. Cycling conditions: 15 min activation at 95° C. followed by 40 cycles of 15 sec 95° C., 15 sec 57° C., and 15 sec 72° C. ACT1, a gene that encodes actin, was used to normalize the amount of the mRNA for the gene of interest in all samples.

REFERENCES FOR METHODS

1. Gibson, D. G., Young, L., Chuang, R-Y., Venter, J. C., Hutchison III, C. A. & Smith, H. O. Enzymatic assembly of DNA molecules up to several hundred kilobases. *Nat. Methods* 6, 343-345 (2009).
2. Peralta-Yahya, P., Carter, B. T., Lin, H., Tao, H. & Cornish, V. W High-Throughput Selection for Cellulase Catalysts Using Chemical Complementation *J. Am. Chem. Soc.* 130 (51), 17446-17452 (2008).
3. Arnold K., Bordoli L., Kopp J. & Schwede T. The SWISS-MODEL Workspace: A web-based environment for protein structure homology modelling. *Bioinformatics* 22, 195-201 (2006).
4. Kiefer F., Arnold K., Kunzli M., Bordoli L. & Schwede T. The SWISS-MODEL Repository and associated resources. *Nucleic Acids Res.* 37, D387-D392 (2009).
5. Peitsch, M. C. Protein modeling by E-mail *Nature Biotechnol.* 13, 658-660 (1995).
6. Kanehisa, M. Goto, S. KEGG:Kyoto encyclopedia of genes and genomes Nucleic Acids Res. 28, 27-30 (2000).
7. Bernhardt, P., Usera, A. R., and O'Connor, S. E. Biocatalytic asymmetric formation of tetrahydro-beta-carbolines. *Tetrahedron Lett.* 51, 4400-4402 (2010).

Example 4: A Method of Producing BH4 in an Engineered Yeast Cell $BH_4$ can be synthesized by a $BH_4$ synthesis pathway 1500 comprising GTP cyclohydrase (GTPCH), pyruvol tetrahydrobiopterin synthase (PTPS), and sepiapterin reductase (SR). A yeast cell can be engineered to express said $BH_4$ synthesis pathway. Said engineered yeast cell can be incubated a carbohydrate for an amount of time to produce $BH_4$. One skilled in the art will recognize the appropriate analysis measures to determine the incubation parameters for suitable BH4 production. The carbohydrate can be glucose or galactose (FIG. 29). Products of the endogenous yeast carbohydrate metabolic pathway are then used by (or coupled to) the engineered BH4 pathway to produce BH4 in the engineered yeast cell.

Example 5: A Method of Producing Serotonin in an Engineered Yeast Cell

A yeast cell can be engineered to express a biocatalyst 2100. The biocatalyst 2100 is comprised of a BH4 synthesis pathway 1500 (1500 comprising GTP cyclohydrase (GTPCH), pyruvol tetrahydrobiopterin synthase (PTPS), and sepiapterin reductase (SR)) and an enzymatic pathway 1000 comprised of tryptophan hydroxylase and aromatic-l-amino acid decarboxylase. Said engineered yeast cell is incubated with a carbohydrate for an amount of time to produce serotonin (FIG. 30). One skilled in the art will recognize the appropriate analysis measures to determine the incubation parameters for suitable serotonin production. The carbohydrate can be glucose or galactose. Products of the endogenous yeast carbohydrate metabolic pathway are then used by (or coupled to) the biocatalyst 2100 to produce serotonin in the engineered yeast cell.

Example 6: A Method of Producing Dopamine in an Engineered Yeast Cell

A yeast cell can be engineered to express a biocatalyst 2100. The biocatalyst 2100 is comprised of a BH4 synthesis pathway 1500 (1500 comprising GTP cyclohydrase (GTPCH), pyruvol tetrahydrobiopterin synthase (PTPS), and sepiapterin reductase (SR)) and an enzymatic pathway 1000 comprised of tyrosine hydroxylase and aromatic-l-amino acid decarboxylase. Said engineered yeast cell is incubated with a carbohydrate for an amount of time to produce dopamine (FIG. 31). One skilled in the art will recognize the appropriate analysis measures to determine the incubation parameters for suitable serotonin production. The carbohydrate can be glucose or galactose. Products of the endogenous yeast carbohydrate metabolic pathway are then used by (or coupled to) the biocatalyst 2100 to produce dopamine in the engineered yeast cell. This method can be used to produce L-DOPA if aromatic-l-amino acid is omitted from the enzymatic pathway 1000.

Example 7: A Method of Producing Hydroxystrictosidine in an Engineered Yeast Cell A yeast cell can be engineered to express a biocatalyst 2100. The biocatalyst 2100 is comprised of a BH4 synthesis pathway 1500 (1500 comprising GTP cyclohydrase (GTPCH), pyruvol tetrahydrobiopterin synthase (PTPS), and sepiapterin reductase (SR)) and an enzymatic pathway 1000 comprised of tyrosine hydroxylase, aromatic-l-amino acid decarboxylase, and strictosidine synthase. Said engineered yeast cell is incubated with a carbohydrate for an amount of time to produce dopamine (FIG. 32). One skilled in the art will recognize the appropriate analysis measures to determine the incubation parameters for suitable hydroxystrictosidine production. The carbohydrate can be glucose or galactose. Products of the endogenous yeast carbohydrate metabolic pathway are then used by (or coupled to) the biocatalyst 2100 to produce hydroxystrictosidine in the engineered yeast cell.

Example 8: Overview of the Microbial Synthesis of L-DOPA, Dopamine, Serotonin and 10-Hydroxystrictosidine (FIG. 33)

Arrows represent presence of the enzyme. nd=not detectable. Amount produced is represented by the mean±standard deviation for samples run in triplicate. GTPCH: GTP cyclohydrolase; PTPS: pyruvoyl tetrahydropterin synthase; SR: sepiapterin reductase; PCD: pterin-4a-carbinolamine dehydratase; DHPR: dihydropteridine reductase; TPH: tryptophan hydroxylase; TH: tyrosine hydroxylase; DDC: aromatic-L-amino-acid decarboxylase; STR: strictosidine synthase.

We claim:

1. A biocatalyst comprising:
    a tetrahydrobiopterin source, wherein the tetrahydrobiopterin source is a tetrahydrobiopterin synthesis pathway comprising:
        a GTP cyclohydrase, wherein the GTP cyclohydrolase is encoded by a nucleotide sequence comprising SEQ ID NO: 1, SEQ ID NO: 2, SEQ ID NO: 3, or SEQ ID NO: 4;
        a pyruvoyl tetrahydropterin synthase, wherein the pyruvoyl tetrahydropterin synthase is encoded by a nucleotide sequence comprising SEQ ID NO: 5, SEQ ID NO: 6, SEQ ID NO: 7, or SEQ ID NO: 8; and
        a sepiapterin reductase, wherein the sepiapterin reductase is encoded by a nucleotide sequence comprising SEQ ID NO: 9, SEQ ID NO: 10, or SEQ ID NO: 11; and
    a pterin-dependent enzymatic pathway, wherein the pterin-dependent enzymatic pathway comprises tryptophan hydroxylase and aromatic-l-amino acid decarboxylase wherein the aromatic-1-amino acid decarboxylase is encoded by a nucleotide sequence comprising SEQ ID NO:17.

2. The biocatalyst of claim 1, further comprising a synthase.

3. The biocatalyst of claim 2, wherein the synthase is a terpene alkaloid synthase, strictosidine synthase, or a deacetylisoipecoside synthase.

4. The biocatalyst of claim 1, further comprising a tetrahydrobiopterin recycling pathway, the tetrahydrobiopterin recycling pathway comprising:
    a pterin-4a-carbinolamine dehydratase; and
    a dihydropterin reductase.

5. An engineered cell comprising:
    a biocatalyst, the biocatalyst comprising:
        a tetrahydrobiopterin source, wherein the tetrahydrobiopterin source is a tetrahydrobiopterin synthesis pathway comprising:
            a GTP cyclohydrase, wherein the GTP cyclohydrolase is encoded by a nucleotide sequence comprising SEQ ID NO: 1, SEQ ID NO: 2, SEQ ID NO: 3, or SEQ ID NO: 4;
            a pyruvoyl tetrahydropterin synthase, wherein the pyruvoyl tetrahydropterin synthase is encoded by a nucleotide sequence comprising SEQ ID NO: 5, SEQ ID NO: 6, SEQ ID NO: 7, or SEQ ID NO: 8; and a sepiapterin reductase, wherein the sepiapterin reductase is encoded by a nucleotide sequence comprising SEQ ID NO: 9, SEQ ID NO: 10, or SEQ ID NO: 11; and a pterin-dependent enzymatic pathway, wherein the pterin-dependent enzymatic pathway comprises tryptophan hydroxylase and aromatic-1-amino acid decarboxylase wherein the aromatic-1-amino acid decarboxylase is encoded by a nucleotide sequence comprising SEQ ID NO:17.

6. The engineered cell of claim 5, further comprising a synthase.

7. The engineered cell of claim 6, wherein the synthase is a terpene alkaloid synthase or a strictosidine synthase.

8. The engineered cell of claim 5, further comprising a tetrahydrobiopterin recycling pathway, the tetrahydrobiopterin recycling pathway comprising:

a pterin-4a-carbinolamine dehydratase; and a dihydropterin reductase.

9. The biocatalyst of claim 1, wherein the amino acid mono-oxygenase is encoded by a nucleotide sequence comprising SEQ ID NO: 15.

10. The engineered cell of claim 5, wherein the amino acid mono-oxygenase is encoded by a nucleotide sequence comprising SEQ ID NO: 15.

11. A biocatalyst comprising:

a tetrahydrobiopterin source;

a pterin-dependent enzymatic pathway, wherein the pterin-dependent enzymatic pathway comprises tryptophan hydroxylase encoded by a nucleotide sequence comprising SEQ ID NO: 15 and aromatic-1-amino acid decarboxylase; and a tetrahydrobiopterin recycling pathway, wherein the tetrahydrobiopterin recycling pathway comprises a pterin-4a-carbinolamine dehydratase and a dihydropterin reductase.

12. The biocatalyst of claim 11, wherein the aromatic-1-amino acid decarboxylase is encoded by a nucleotide sequence comprising SEQ ID NO: 17.

13. The biocatalyst of claim 11, wherein the pterin-4a-carbinolamine dehydratase is encoded by a nucleotide sequence comprising SEQ ID NO: 12 and the dihydropterin reductase is encoded by a nucleotide sequence comprising SEQ ID NO: 13.

14. The biocatalyst of claim 11, wherein the tetrahydrobiopterin source is a tetrahydrobiopterin synthesis pathway comprising:

a GTP cyclohydrase encoded by a nucleotide sequence comprising SEQ ID NO: 1;

a pyruvoyl tetrahydropterin synthase encoded by a nucleotide sequence comprising SEQ ID NO: 5; and a sepiapterin reductase encoded by a nucleotide sequence comprising SEQ ID NO: 9.

* * * * *

SEQUENCE LISTING

```
<160> NUMBER OF SEQ ID NOS: 17

<210> SEQ ID NO 1
<211> LENGTH: 687
<212> TYPE: DNA
<213> ORGANISM: Artificial Sequence
<220> FEATURE:
<223> OTHER INFORMATION: GTP cyclohydrolase I

<400> SEQUENCE: 1
atgcatcacc atcaccatca cccatcactc agtaaagaag cggccctggt tcatgaagcg      60
ttagttgcgc gaggactgga aacaccgctg cgcccgcccg tgcatgaaat ggataacgaa     120
acgcgcaaaa gccttattgc tggtcatatg accgaaatca tgcagctgct gaatctcgac     180
ctggctgatg acagtttgat ggaaacgccg catcgcatcg ctaaaatgta tgtcgatgaa     240
attttctccg gtctggatta cgccaatttc ccgaaaatca ccctcattga aaacaaaatg     300
aaggtcgatg aaatggtcac cgtgcgcgat atcactctga ccagcacctg tgaacaccat     360
tttgttacca tcgatggcaa agcgacggtg gcctatatcc cgaaagattc ggtgatcggt     420
ctgtcaaaaa ttaaccgcat tgtgcagttc tttgcccagc gtccgcaggt gcaggaacgt     480
ctgacgcagc aaattcttat tgcgctacaa acgctgctgg gcaccaataa cgtggctgtc     540
tcgatcgacg cggtgcatta ctgcgtgaag gcgcgtggca tccgcgatgc aaccagtgcc     600
acgacaacga cctctcttgg tggattgttc aaatccagtc agaatacgcg ccacgagttt     660
ctgcgcgctg tgcgtcatca caactaa                                         687

<210> SEQ ID NO 2
```

<211> LENGTH: 825
<212> TYPE: DNA
<213> ORGANISM: Artificial Sequence
<220> FEATURE:
<223> OTHER INFORMATION: GTP cyclohydrolase I

<400> SEQUENCE: 2

```
atgcatcacc atcaccatca ctcccatact ccaacctctc caaagaccgc ttcctctgtt    60
gaattggttc atccaaccgc aaagcaagca ttgttgaacc acgctttgac tggtcattcc   120
cattcctctg gtagatccta cttgaagtcc gaatctccag aaggtagatc cgctactcca   180
attgatttcg acggtttatc ctttccatcc attggtgcta gagatagaag agaagatacc   240
gaagaacaaa gagctgctag aattgagaag atagctggtt ccgttagaac cattttggag   300
tgtattggtg aagatccaga tagagaaggt tgttgaaga ctccagaaag atacgctaag   360
gcattgatgt tcttctccaa aggttacgaa gaatccgtta ctcatttgat gaataaggca   420
ttatttcaag aagatcacga cgaaatggtt attgttaaag atattgacgt tttctccttg   480
tgtgaacatc atatggttcc atttactggt aagattcata ttggttacat tccaaagaac   540
ggtaaggttg ttggttttgtc caaaattgct agattggctg aaatgttttc cagaagattg   600
caagttcaag aaagattgac caaacaagtt gctatggctt tgcaagaatt gttagatcca   660
ttgggtgttg ctgttgttat ggaagcatct catttctgta tggttatgag aggtgttcaa   720
aagccaggtt ctcaaaccat tacctcctct atgtttggtt gttttagaga tcaaggtaaa   780
accagagaag agttcttgtc cttgattaga agaagaggtg tttaa              825
```

<210> SEQ ID NO 3
<211> LENGTH: 750
<212> TYPE: DNA
<213> ORGANISM: Artificial Sequence
<220> FEATURE:
<223> OTHER INFORMATION: GTP cyclohydrolase I

<400> SEQUENCE: 3

```
atgcatcacc atcaccatca ccataacatc caattagtgc aagagataga aagacatgaa    60
accccgttaa acattagacc tacctctcca tacacttttaa accctcctgt cgagagagat   120
gggttttctt ggccaagtgt gggtacaaga caacgtgcag aggaaactga agaggaggaa   180
aaggaacgaa ttcaacgcat ttcaggcgct atcaagacaa ttttgaccga actgggtgaa   240
gatgtcaaca gagaaggtct actagatact ccacaaagat acgctaaagc catgctttat   300
ttcactaaag gttaccaaac gaacattatg gacgatgtca ttaagaatgc tgtctttgaa   360
gaagatcatg atgaaatggt tattgttcgt gatattgaaa tttactcgtt atgtgaacat   420
catttggtgc catttttcgg caaggttcat atcgggtata taccaaataa aaaagtcatc   480
gggttaagta agttggccag attggcagaa atgtatgcga gaaggctcca agttcaagaa   540
agacttacaa agcaaattgc aatggcccta agtgatattc taaaaccatt aggtgtagcc   600
gttgttatgg aagcttctca tatgtgcatg gtttcaagag gcattcaaaa aacgggatct   660
tctacggtaa cttcttgtat gcttggaggg tttagggctc ataaaacaag agaagagttt   720
ttaactcttt taggaagaag aagtatttaa                                     750
```

<210> SEQ ID NO 4
<211> LENGTH: 771
<212> TYPE: DNA
<213> ORGANISM: Artificial Sequence
<220> FEATURE:
<223> OTHER INFORMATION: GTP cyclohydrolase I

<400> SEQUENCE: 4

```
atgcatcacc atcaccatca cgagaaaggt ccagttagag ctccagcaga gaagccaaga    60
ggtgctagat gttctaacgg atttccagaa agagatcctc caagaccagg tccttctaga   120
ccagctgaga aaccacctag accagaagct aaatctgctc aaccagctga cggttggaaa   180
ggtgaaagac caagatctga gaggacaac gaattgaatc taccaaatct agctgccgct   240
tattcatcta tcttgtcttc cttgggagag aatccacaaa gacaaggtct attgaagact   300
ccttggagag ctgcctctgc tatgcaattc tttactaaag gttatcaaga aactatttct   360
gacgttttga acgacgcaat cttcgacgag atcacgacg agatggttat tgtcaaagat   420
attgatatgt tctctatgtg tgaacaccac ttggttccat tgttggtaa agttcacatt   480
ggttatttgc taataagca gttttgggt ttgtctaaat tggctagaat tgttgaaatc   540
tattctagaa gattgcaagt tcaagaaaga ttgactaaac aaattgctgt tgctattact   600
gaagcattga ccagcagg tgttggtgtt gtcgttgaag ctactcacat gtgtatggtt   660
atgagaggtg ttcagaagat gaactctaag actgttactt ctactatgtt gggtgtcttt   720
agagaagatc caaagactag agaagagttc ttgactttga ttagatctta a          771
```

<210> SEQ ID NO 5
<211> LENGTH: 459
<212> TYPE: DNA
<213> ORGANISM: Artificial Sequence
<220> FEATURE:
<223> OTHER INFORMATION: 6-pyruvoyl tetrahydrobiopterin synthase

<400> SEQUENCE: 5

```
atgcatcacc atcaccatca cacctcctca actccagtta gaactgctta cgttaccaga    60
attgaacatt tctccgctgc tcatagattg aattccgttc atttgtctcc tgctgaaaac   120
gttaagttgt tcggtaagtg taatcatact tccggtcacg gtcataatta caaggttgaa   180
gttaccatta aaggtcaaat taatccacaa tccggtatgg ttattaacat taccgatttg   240
aagaagacct tgcaagttgc tgttatggac ccttgtgatc atagaaattt ggatattgat   300
gttccatact tcgaatccag accatccacc actgaaaaact tggctgtctt cttgtgggaa   360
aacattaagt cccatttgcc accatccgat gcttacgatt tgtacgaaat taagttgcac   420
gaaaccgata gaacgttgt cgtttacaga ggtgaataa                          459
```

<210> SEQ ID NO 6
<211> LENGTH: 465
<212> TYPE: DNA
<213> ORGANISM: Artificial Sequence
<220> FEATURE:
<223> OTHER INFORMATION: 6-pyruvoyl tetrahydrobiopterin synthase

<400> SEQUENCE: 6

```
atgcatcacc atcaccatca cgctcaagct gattccagaa acgaagttgc tgaaagaatt    60
ggttacatta ccagagttca atccttctcc gcttgtcata gattgcattc cccaaccttg   120
tccgatgaag tcaacaagag aatcttcggt aagtgtaaca atccaaacgg tcacggtcat   180
aactacaagg ttgaagtcac cgtcagaggt aagattgata gacatactgg tatggtcatg   240
aacattaccg atttgaagca acatattgaa gaagtcatta tgattccatt ggatcataag   300
aatttggata ggacgttcc atactttgct aacgttgtct ctactaccga aaacgttgct   360
gtctacattt gggataacat ggttaagcaa ttgccagcta acttgttgta cgaagttaag   420
```
attcacgaaa ccgataagaa cattgttgtc tacagaggtg aataa    465

<210> SEQ ID NO 7
<211> LENGTH: 432
<212> TYPE: DNA
<213> ORGANISM: Artificial Sequence
<220> FEATURE:
<223> OTHER INFORMATION: 6-carboxy-5,6,7,8-tetrahydropterin synthase

<400> SEQUENCE: 7
atgcatcacc atcaccatca ctccaccgtt tacattacca gaaaggttca tttcaacgct    60
gctcatagat tgcataatcc aaataagtcc gatgcttgga acgaagatac ctacggtaag   120
gataacaatc caaactggca tggtcataac tacgaattgg aagtcaccgt tgctggtgaa   180
ccagatccag aaaccggtta cgttgtcgat ttgggtgtct tgaaggatat tttgcatgat   240
agagttttgg ataaggttga tcataagaac ttgaacttgg aagtcgattt catggatggt   300
gttattcctt cctctgaaaa cttcgctatt gctatttgga atgaaattga agatgctttg   360
ccaaacggtg aattgcattg tgtcagattg tacgaaactc aagaaactt cgttgaatac    420
agaggtgaat aa    432

<210> SEQ ID NO 8
<211> LENGTH: 786
<212> TYPE: DNA
<213> ORGANISM: Artificial Sequence
<220> FEATURE:
<223> OTHER INFORMATION: Putative 6-pyruvoyl tetrahydrobiopterin
      synthase

<400> SEQUENCE: 8
atgcatcacc atcaccatca ctttgaattg actagaactt taagattttg tccatctggt    60
gatccaggtg ctccaagaga taacgctcat gctgcttggc caccaccaag aggtttagca   120
ggtgtattat ctttagattt gactattgct ggtagaccag atccaggtac tggtgtttta   180
ttgaacgtta agatttagag tgcagctttt gctgccgctg cattaccaag attcagagca   240
gctgcaggtg ctgaaccagc aggtttattg agaggtgttg ctcaagcatt agctcctact   300
ttaccatttc cattgttaag attgagatta tctgcatctg cttcagcttc tactgaattg   360
agaccagctg atatgtctag agttattttg agacaaagat tctctttctc tgctgctcat   420
agattacaag ctgatgcttt gtctgaagag gaaaatagaa cattgtttgg taagtgtaat   480
agaccatctt ttcatggtca taattacgaa ttagaagttg ctgcagccgc tgctattgct   540
ccagatggta gatctttaga accagctgca ttagatgctg ctgttagaac tagagtcatt   600
gatactttag atcatagaaa tttgaatact gatgttgctg cttttgctac tagaaatcca   660
actgttgaac atattgctca aacttgttgg gatttgttag ctggtggttt accagaaggt   720
gcagaattac aagaagttgt agtttgggaa actgatgaaa catcttgtgc ttatagaggt   780
ggttaa    786

<210> SEQ ID NO 9
<211> LENGTH: 867
<212> TYPE: DNA
<213> ORGANISM: Artificial Sequence
<220> FEATURE:
<223> OTHER INFORMATION: Sepiapterin reductase

<400> SEQUENCE: 9
atgcatcacc atcaccatca ctcatccaaa gaacatcatt tggttattat taacggtgtt    60

```
aatagaggtt ttggtcattc cgttgcattg gattacataa gacattcagg tgctcatgct      120
gtttcctttg ttttggttgg tagaactcaa cattccttgg aacaagtttt gactgaattg      180
catgaagctg catctcatgc tggtgttgtc ttcaagggtg tcgttgtctc cgaagttgat      240
ttggctcatt tgaactcttt ggattctaat ttggctagaa tacaatctgc tgcagctgat      300
ttgagagacg aagctgcaca atctaccaga actattacta agtctgtttt gtttaataac      360
gctggttcat tgggtgattt gtccaagact gttaaggaat ttacctggca agaagctaga      420
tcctacttgg atttcaacgt cgtttcctta gttggtttgt gttccatgtt cttgaaggat      480
accttggaag catttccaaa ggaacaatat ccagatcata gaactgttgt cgtttccatt      540
tcttccttgt tagctgttca agcattccca aattggggtt tgtacgctgc aggtaaggca      600
gctagagata gattgttagg tgttattgct ttggaagaag cagctaataa cgttaagacc      660
ttgaattacg ctccaggtcc attggataac gaaatgcaag ctgatgttag aagaaccttg      720
ggtgataaag aacaattgaa gatttacgat gatatgcata agtctggttc cttggttaag      780
atggaagatt cctctagaaa gttgattcat ttgttaaagg ctgataccct cacctccggt      840
ggtcatattg atttctacga tgaataa                                          867

<210> SEQ ID NO 10
<211> LENGTH: 783
<212> TYPE: DNA
<213> ORGANISM: Artificial Sequence
<220> FEATURE:
<223> OTHER INFORMATION: Putative cytoplasmic short-chain
      dehydrogenase/reductase

<400> SEQUENCE: 10
atgcatcacc atcaccatca cggtaaagtt atttttagtta caggtgtttc cagaggtatc       60
ggtaagtcca tcgtggatgt tcttttcagt ttggacaagg acacggttgt ttacggtgta      120
gccaggtctg aggcacccct tgaagaagtt aaagagaagt atggcgacag gtttttttac      180
gttgtcggtg atattaccga ggattccgtg ttgaagcagt tggttaacgc tgctgttaag      240
ggccacggca agatcgactc cttggttgcc aacgctggtg tcctagagcc cgtgcaaaat      300
gtcaacgaga ttgatgtcaa cgcttggaag aagctgtatg acatcaactt cttcagcatt      360
gtttccttgg ttggcattgc gttacctgaa ttgaagaaga ccaacggtaa cgtggtattc      420
gtcagttcgg acgcctgtaa catgtacttc agcagttggg gagcttacgg ttcttcaaaa      480
gccgctctga accacttcgc catgactctg gccaacgagg aaaggcaagt gaaagccatt      540
gccgtcgccc aggtattgt ggacacagat atgcaagtta acattaggga acgtgggg        600 ccttcctcca tgagtgcaga gcaattgaag atgtttagag gtttaaagga gaataaccag      660
ttgctggata gctctgtgcc agctacagtt tatgcccaaat tggcccttca tggtattcct      720
gacggtgtta atggacagta cttgagctat aatgaccctg ccttggcgga ctttatgcct      780
taa                                                                   783

<210> SEQ ID NO 11
<211> LENGTH: 696
<212> TYPE: DNA
<213> ORGANISM: Artificial Sequence
<220> FEATURE:
<223> OTHER INFORMATION: Sepiapterin reductase

<400> SEQUENCE: 11
atgcatcacc atcaccatca ccaaaacaag gaaaacgatg aaacctccat tgttgtcgat       60
```

```
attcatgaaa tggatttgtc cgatttggat attttggctg ttaacatgaa gttgttgttt    120
gaattctaca ccaaggttac caagtacaat caatgttggt tgttcaacaa tgctggttcc    180
ttgggtccat tgggtccaac cttgtccttg tgtaacggtg atccattgag attaatgcaa    240
gatttgaaga aagctgttga tttgaacgtt acctccgcta cctggatttc ctcacaattc    300
gtttccacct ttggttcctc tcataaggac gatactccac cattggttag aattgttaac    360
atttcttcct tgtgtgctat tgaaccattc caaactatgg ctgtttactg tatgggtaag    420
gctgcaagag atatgtacca tttggttttg gctaaagaac ataaggattc cgatactatg    480
aaagttttga actacgctcc aggtccttgt gatactgaaa tgactgatgt tttggctggt    540
tctgctgttt tggattggga tttgcatcaa tattacgcta catccaagag agatcaaaag    600
ttggttgatc ctttggattc tgctaagaaa ttgattgaat tgttagaaaa ggatgaattc    660
accacaggtt cccatgttga ttacttcgat gtttaa                              696

<210> SEQ ID NO 12
<211> LENGTH: 315
<212> TYPE: DNA
<213> ORGANISM: Artificial Sequence
<220> FEATURE:
<223> OTHER INFORMATION: Pterin-4-alpha-carbinolamine dehydratase

<400> SEQUENCE: 12
atggctggta aagctcatag attgtctgct gaagaaagag atcaattgtt gccaaacttg     60
agagctgttg ttggaacga attggaaggt agagatgcta ttttcaagca attccatttc    120
aaagatttca atagagcctt cggtttcatg actagagttg ccttgcaagc tgaaaagtta    180
gatcatcatc cagaatggtt caacgtctac aataaggtcc atattacctt gtccactcat    240
gaatgtgctg gttgtctga aagagatatt aacttggcat ccttcattga acaagtcgct    300
gtctccatga cttaa                                                     315

<210> SEQ ID NO 13
<211> LENGTH: 735
<212> TYPE: DNA
<213> ORGANISM: Artificial Sequence
<220> FEATURE:
<223> OTHER INFORMATION: Dihydropteridine reductase

<400> SEQUENCE: 13
atggcagctg ctgcagccgc tggtgaagct agaagagttt tggtttacgg tggtagaggt     60
gctttgggtt ctagatgtgt ccaagcattc agagctagaa attggtgggt tgcttctgtt    120
gatgtcgttg aaaacgaaga agcatctgct tctattattg ttaaaatgac tgattctttt    180
actgaacaag ctgatcaagt tactgctgaa gttggtaaat tgttaggtga agagaaagtt    240
gatgctattt tgtgtgttgc tggtggttgg ctggtggta acgctaaatc taaatctttg    300
tttaagaatt gtgatttgat gtggaaacaa tctatttgga cttctactat tcttctcat    360 ttggctacta acatttgaa agaaggtggt ttgttaactt tggcaggtgc taaagctgct    420
ttggatggta ctccaggtat gattggttac ggtatggcta aggtgcagt tcatcaattg    480 tgtcaatctt tggctggtaa gaactctggt atgccacctg gtcagctgc tattgctgtt    540 ttgccagtta cttttggatac accaatgaat agaaaatcta tgccagaagc tgatttctct    600
tcttggactc cattggaatt cttggttgaa actttcatg attggattac tggaaagaat    660
agaccatctt ctgttctttt gattcaagtt gttactactg aaggtagaac tgaattgact    720
ccagcttatt tctaa                                                     735
```

<210> SEQ ID NO 14
<211> LENGTH: 1497
<212> TYPE: DNA
<213> ORGANISM: Artificial Sequence
<220> FEATURE:
<223> OTHER INFORMATION: Tyrosine 3-monooxygenase

<400> SEQUENCE: 14

```
atgccaactc catccgcttc ctccccacaa ccaaagggtt tcagacgcgc tgtgtctgaa      60
caagatacta agcaagctga agctgttact tccccaagat tcatcggtag aagacaatct     120
ttgattgaag atgctagaaa ggaaagagaa gctgcagctg cagccgctgc agccgctgtt     180
gcttctgctg aaccaggtaa tccattggaa gctgttgtct tcgaagaaag agatggtaat     240
gctgttttga atttgttgtt ctctttgaga ggtactaagc catcttcctt gtctagagct     300
ctaaaggtat tcgaaacttt cgaagctaag attcatcatt ggaaactaga acctgcacaa     360
agaccattgg ctggttcccc acatttggaa tacttcgtta gatttgaagt tccatccggt     420
gatttggctg ctttgttgtc ttccgttaga agagtttctg atgatgttag atccgctaga     480
gaagataagg ttccttggtt ccaagaaagg gtttctgaat tggataagtg tcatcatttg     540
gttactaagt ttgatccaga tttggatttg gatcatccag gtttctccga tcaagcatac     600
agacaaagaa gaaagttgat tgctgaaatt gctttccaat acaagcaagg tgaaccaatt     660
ccacatgttg aatacactaa ggaagaaatt gctacttgga aggaagttta cgctactttg     720
aagggtttgt acgctactca tgcttgtaga gaacatttgg aagcatttca attgttggaa     780
agatactgtg gttacagaga agattctatt ccacaattgg aagatgtttc tcatttcttg     840
aaggaaagaa ctggttttcca attgagacca gttgctggtt tgttgtccgc tagagatttc     900
ttggcttcct ggcttttcag agtttttccaa tgtactcaat acattagaca tgcttcctcc     960
ccaatgcatt ctccagaacc agattgttgt catgaattgt tgggtcatgt tccaatgttg    1020
gctgatagaa ctttcgctca attctctcaa gatattggtt tggcttcttt gggtgcttct    1080
gatgaagaaa ttgaaaagtt gtccactgtt tactggttta ctgttgaatt tggtttgtgt    1140
aagcaaaatg gtgaattgaa ggcttacggt gccggattgt tgtcctctta cggtgaattg    1200
ttgcattctt tgtctgaaga accagaagtt agagctttcg atccagatac tgctgctgtt    1260
caaccatacc aagatcaaac ttaccaacca gtttacttcg tttctgaatc tttctctgat    1320
gctaaggata gttgagaaa ttacgcttct agaatccaaa gaccattctc tgttaagttt    1380
gatccataca ctttggctat tgatgtcttg gattctccac atactattag aagatctttg    1440
gaaggtgttc aagatgaatt gcatactttg actcaagcat tgtctgctat ttcttaa       1497
```

<210> SEQ ID NO 15
<211> LENGTH: 951
<212> TYPE: DNA
<213> ORGANISM: Artificial Sequence
<220> FEATURE:
<223> OTHER INFORMATION: Tryptophan-5-hydroxylase 2 isoform 1 AA145-460

<400> SEQUENCE: 15

```
atggaagaat tggaagatgt tccttggttc ccaagaaaga tttccgaatt ggataagtgt      60
tcccatagag ttttgatgta tggttccgaa ttggatgctg atcatccagg tttcaaggat     120
aatgtttaca gacaaagaag aaagtacttc gttgatgttg ctatgggtta caagtacggt     180
caaccaattc caagagttga atacactgaa gaagaaacta gacttgggg cgttgtgttc     240
```

| | | |
|---|---|---|
| agagaattgt ccaagttgta cccaactcat gcttgtagag aatacttgaa gaatttccca | 300 | |
| ttgttgacta agtactgtgg ttacagagaa gataatgttc cacaattgga agatgtttcc | 360 | |
| atgttcttga aggaaagatc cggtttcact gttagaccag ttgctggtta cttgtcccca | 420 | |
| agagatttct tggctggttt ggcttacaga gtcttccatt gtactcaata cattagacat | 480 | |
| ggttccgatc cattgtacac tccagaacca gatacttgtc atgaattgtt gggtcatgtt | 540 | |
| ccattgttgg ctgatccaaa gttcgctcaa ttctcccaag aaattggttt ggcttccttg | 600 | |
| ggtgcttccg atgaagatgt tcaaaagttg gctacttgtt acttcttcac tattgaattc | 660 | |
| ggtttgtgta agcaagaagg tcaattgaga gcttacggtg ctggttttgt tatcctctatt | 720 | |
| ggtgaattga agcacgcttt gtccgataag gcttgtgtta aggctttcga cccaaagact | 780 | |
| acttgtttgc aagaatgttt gattactact ttccaagaag catacttcgt ttccgaatcc | 840 | |
| ttcgaagaag ctaaggagaa gatgagagat ttcgctaagt ccattactag accattctcc | 900 | |
| gtttacttca atccatacac tcaatccatt gaaattttga aggatactta a | 951 | |

<210> SEQ ID NO 16
<211> LENGTH: 1461
<212> TYPE: DNA
<213> ORGANISM: Artificial Sequence
<220> FEATURE:
<223> OTHER INFORMATION: Aromatic-L-amino-acid decarboxylase

<400> SEQUENCE: 16

| | | |
|---|---|---|
| atgaatgctt ctgattttag aaggagaggt aaagaaatgg ttgactacat ggctgattac | 60 | |
| ttggaaggta ttgaaggtag acaagtttac ccagatgttc aaccaggtta cttgagacca | 120 | |
| ttgattccag ctactgctcc acaagaacca gatactttg aagatatttt gcaagatgtt | 180 | |
| gagaagatta ttatgccagg tgtcacacat tggcactcgc catacttctt tgcttacttc | 240 | |
| ccaactgctt cctcctaccc agctatgttg gctgatatgt tgtgtggtgc tattggttgt | 300 | |
| attggtttct cctgggctgc ttccccagct tgtactgaat tggaaactgt tatgatggat | 360 | |
| tggttgggta aaatgttgca attgccagaa gccttcttgg ctggtgaagc tggtgaaggt | 420 | |
| ggtggtgtta ttcaaggttc cgcttccgaa gctactttgg ttgctttgtt ggctgctaga | 480 | |
| actaaagtta ctagaagatt gcaagctgct tctccaggtt tgactcaagg tgctgttttg | 540 | |
| gagaagttgg ttgcttacgc ctccgaccaa gctcattcct ccgttgaaag agctggtttg | 600 | |
| attggtggtg ttaaattgaa agctattcca tccgatggta aatttgctat gagagcttcc | 660 | |
| gctttgcaag aagccttgga aagagataaa gctgctggtt tgattccatt cttcgttgtt | 720 | |
| gctactttgg gtactacttc ctgttgttcc tttgataatt tgttggaagt tggtccaatt | 780 | |
| tgtcatgaag aagatatttg gttgcatgtt gatgctgctt acgctggttc cgcttttcatt | 840 | |
| tgtccagaat ttagacattt gttgaatggt gttgaatttg ctgattcctt taatttcaat | 900 | |
| ccacataaat ggttgttggt taattttgat tgttccgcta tgtgggttaa agaagaact | 960 | |
| gatttgactg gtgcttttaa attggaccca gtttacttga acattccca tcaaggttcc | 1020 | |
| ggtttgatta ctgattacag acattggcaa ttgccattgg gtagaagatt tagatccttg | 1080 | |
| aaaatgtggt ttgtcttcag aatgtacggt gttaaaggtt tgcaagccta cattagaaag | 1140 | |
| catgttcaat gtcccatga atttgaagcc tttgttttgc aagatccaag atttgaagtt | 1200 | |
| tgtgctgaag ttacttggg tttggttgt tttagattga aggttccga tggtttgaat | 1260 | |
| gaggctttgt tggaaagaat taattccgct agaaagattc atttggttcc atgtagattg | 1320 | |
| agaggtcaat tgttttgag atttgctatt tgttccagaa aagttgaatc cggtcatgtt | 1380 | |

```
agattggctt gggaacatat tagaggtttg gctgctgaat tgttggctgc tgaagaaggt    1440
aaagctgaaa ttaaatctta a                                              1461
```

<210> SEQ ID NO 17
<211> LENGTH: 1011
<212> TYPE: DNA
<213> ORGANISM: Artificial Sequence
<220> FEATURE:
<223> OTHER INFORMATION: Strictosidine synthase AA26-350, His6 only
      included in pAME64

<400> SEQUENCE: 17

```
atgggctctc ctgagttttt cgaatttatt gaagcaccgt cttatggtcc aaatgcgtat      60
gcgttcgaca gcgacggcga gttgtatgcg agcgtggaag acggtcgtat tatcaagtac     120
gacaagcctt ctaacaaatt cctgactcat gctgttgcca gcccgatctg gaacaatgcc     180
ctgtgtgaga ataataccaa ccaagacctg aagccgctgt gcggtcgcgt ctacgacttt     240
ggttttcatt atgaaacgca gcgcctgtac attgcagatt gctacttcgg cttgggcttt     300
gttggtccgg acggcggtca cgcgattcaa ctggcaacct ccggtgatgg cgttgagttc     360
aagtggctgt acgcgttggc gatcgaccaa caggcaggct tcgtctacgt gacggacgtt     420
tctactaagt acgatgatcg tggtgttcag gacattattc gcattaatga taccacgggt     480
cgcctgatta gtatgaccc ttcgaccgaa gaggtgaccg tgctgatgaa aggcctgaat      540
attccgggcg gtaccgaggt tagcaaagac ggtagctttg tgctggttgg tgagttcgcg     600
tcgcatcgta tcctgaagta ctggctgaag ggtccgaagg ccaataccag cgagtttctg     660
ctgaaggtgc gcggtccagg taatatcaaa cgtaccaaag atggtgattt ctgggttgcg     720
tccagcgata caacggcat cacggtgacg ccacgtggta tccgcttcga tgagtttggc      780
aacattctgg aggtcgttgc tattccgctg ccgtataaag gtgaacatat cgagcaggtc     840
caagaacacg acggcgccct gttcgtgggt agcctgtttc atgagttcgt cggcatcctg     900
cataactata agagcagcgt tgaccatcat caggaaaaga actcgggtgg tctgaacgcg     960
agcttcaagg agttctcttc gtttggatct catcaccatc accatcacta g             1011
```